(12) United States Patent
Thomas

(10) Patent No.: US 9,279,811 B2
(45) Date of Patent: Mar. 8, 2016

(54) METHODS AND KITS THAT IDENTIFY TUMORS RESPONSIVE TO SRC INHIBITORS

(71) Applicant: George V. Thomas, Lake Oswego, OR (US)

(72) Inventor: George V. Thomas, Lake Oswego, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

(21) Appl. No.: 14/090,860

(22) Filed: Nov. 26, 2013

(65) Prior Publication Data
US 2014/0088113 A1    Mar. 27, 2014

Related U.S. Application Data

(63) Continuation of application No. PCT/US2012/040046, filed on May 30, 2012.

(60) Provisional application No. 61/491,758, filed on May 31, 2011.

(51) Int. Cl.
G01N 33/574 (2006.01)
C12Q 1/68 (2006.01)

(52) U.S. Cl.
CPC ............ *G01N 33/574* (2013.01); *C12Q 1/6886* (2013.01); *G01N 33/57407* (2013.01); *G01N 33/57438* (2013.01); *C12Q 2600/106* (2013.01); *C12Q 2600/158* (2013.01); *G01N 2333/4703* (2013.01); *G01N 2333/91205* (2013.01); *G01N 2333/91215* (2013.01); *G01N 2333/988* (2013.01)

(58) Field of Classification Search
CPC ........... C12Q 1/6886; C12Q 2600/158; G01N 2333/4703; G01N 33/574
See application file for complete search history.

(56) References Cited

U.S. PATENT DOCUMENTS

| 2002/0048794 | A1* | 4/2002 | Poellinger et al. | 435/69.1 |
| 2003/0170660 | A1* | 9/2003 | Sondergaard et al. | 435/6 |
| 2003/0215899 | A1* | 11/2003 | Meng et al. | 435/21 |
| 2008/0038269 | A1* | 2/2008 | Susan | 424/139.1 |

OTHER PUBLICATIONS

Chou et al. (Genes and Cancer, 1(3): 225-238, 2010).*
Nam et al. (Cancer Res, 65: 9185-9189, 2005).*

* cited by examiner

*Primary Examiner* — Brad Duffy
*Assistant Examiner* — Nelson B Moseley, II
(74) *Attorney, Agent, or Firm* — Jeffrey M. Jackson

(57) ABSTRACT

Disclosed herein are methods of predicting whether or not a subject will benefit from treatment with a Src inhibitor on the basis of the expression of one or more of Von Hippel Lindau (VHL), Src, PTP1B, pFAK, HIF-1α, and/or CA-IX in a tumor sample from the subject.

8 Claims, 21 Drawing Sheets

Figure 2C1
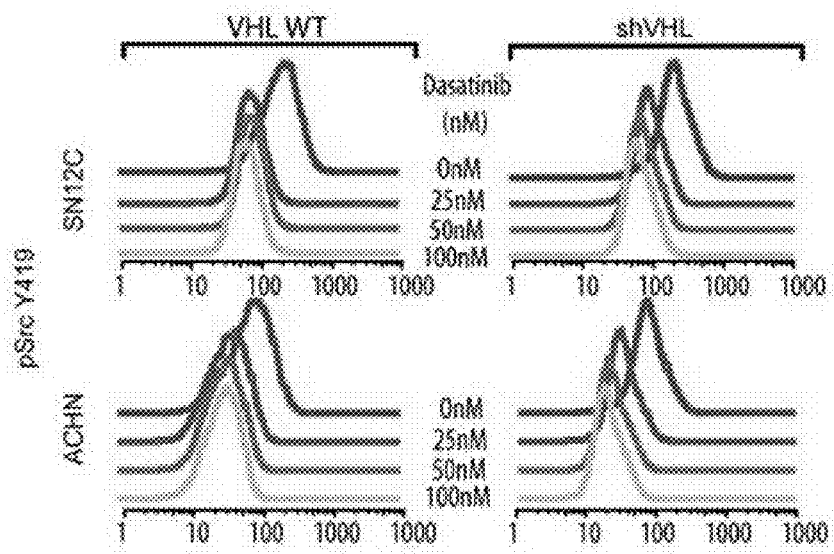
Figure 2C2
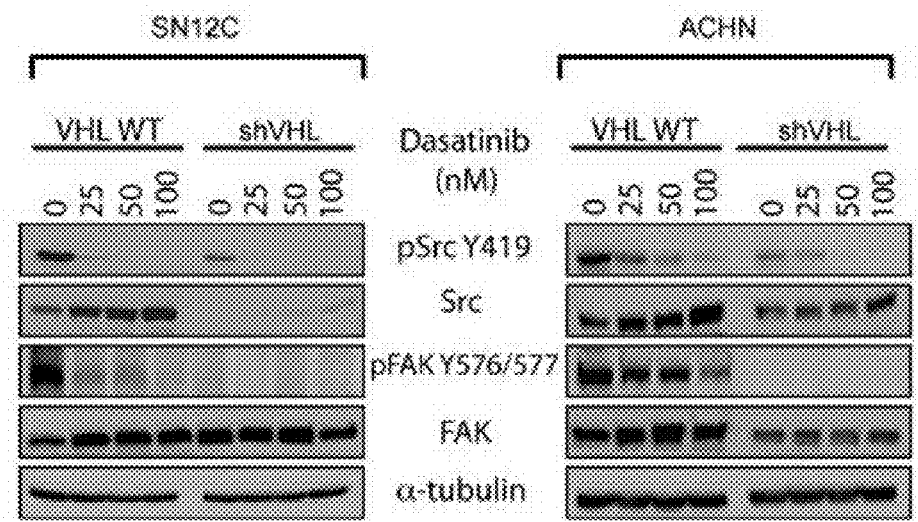

Caki-1

786-0

METHODS AND KITS THAT IDENTIFY TUMORS RESPONSIVE TO SRC INHIBITORS

PRIORITY CLAIM

This application claims priority to U.S. Provisional Application No. 61/491,758, filed 31 May 2011 and PCT/US12/40046, both of which are hereby incorporated by reference in their entireties.

ACKNOWLEDGEMENT OF GOVERNMENT SUPPORT

This invention was made with United States government support pursuant to Grant Numbers DK37274, CA151564, 1KL2 RR024141 01, RR024140, R01CA149253-01 and P30 CA069533 13S5 awarded by the National Institutes of Health. The United States Government has certain rights in this invention.

FIELD

This disclosure relates to the field of tumor biomarkers and in particular, to methods of identifying subjects with cancer for treatment with inhibitors of Src kinase.

BACKGROUND

Cancer is the second leading cause of death in the United States. There is an acute need for cancer biomarkers that can be detected from clinically relevant samples and used for determining treatment regimes applicable to malignant diseases. Renal cell carcinoma (RCC) is the most lethal genitourinary cancer, accounting for approximately 209,000 new cancer occurrences and 102,000 deaths per year worldwide (Gupta et al, Cancer Treat Rev 34, 193 (2008); incorporated by reference herein.) Cure rates in RCC are modest since more than a quarter of patients have metastatic disease at presentation and patients treated surgically for localized cancers frequently relapse with metastatic disease (see Janzen et al, *Urol Clin North Am* 30, 843 (2003) and Lam et al, Curr Urol Rep 6, 7 (2005), both of which are incorporated by reference herein.)

RCC is histologically heterogeneous. While approximately 75% of RCC are clear cell carcinomas, other RCC cell types include papillary, chromophobe, sarcomatoid, collecting duct and medullary carcinomas (Bonsib, *Clin J Am Soc Nephrol* 4, 1998 (2009); incorporated by reference herein.) Inactivation of the VHL tumor suppressor gene is the most prevalent driver mutation, accounting for approximately 60% of all RCC tumors, occurring primarily in the clear cell subtype (Dalgliesh et al, *Nature* 463, 360 (2010) and Kim and Kaelin, J Clin Oncol 22, 4991 (2004); both of which are incorporated by reference herein.) Drugs that target VEGF and mTOR show clinical activity in unselected patients with metastatic RCC, though these responses are often variable and short-lived (Thomas et al, Nat Med 12, 122 (2006) and Rini and Atkins, *Lancet Oncol* 10, 992 (2009); both of which are incorporated by reference herein.)

Despite the fact that VHL-positive cancers account for approximately 40% of RCC, these patients suffer from a lack of biologically rational treatment options due to a paucity of identified molecular drivers. Furthermore, patients with papillary RCC and other "non-clear cell" RCC are often excluded from many registration trials (Motzer et al, J Clin Oncol 20, 2376 (2002) and Ronnen et al, Cancer 107, 2617 (2006); both of which are incorporated by reference herein), indicating that identification of predictive biomarkers that stratify patients for rational treatment strategies are needed.

The profound ability of the Bcr-Abl inhibitor imatinib to successfully treat CML supports such an approach and has led to the development of targeted therapies for other cancers (Demetri et al, N Engl J Med 347, 472 (2002); Druker et al, N Engl J Med 344, 1038 (2001) and Flaherty et al, N Engl J Med 363, 809 (2010); all of which are incorporated by reference herein.) But whereas targeted therapies are most effective in treating homogenous cancers driven by a single activating oncogene, they are much less effective in treating molecularly heterogeneous cancers such as RCC. Indeed, recent quantitative phosphoproteomic studies have revealed cancer to be a disease driven by aberrant networks rather than discrete signaling pathways (Huang et al, Proc Natl Acad Sci USA 104, 12867 (2007) and Stommel et al, *Science* 318, 287 (2007); both of which are incorporated by reference herein.) This observation is exemplified by Src kinase, which despite its pivotal role in tumor growth, angiogenesis and metastasis, is rarely mutated in cancer.

SUMMARY

Metastatic renal cell carcinoma (RCC) is a molecularly heterogeneous disease that is intrinsically resistant to chemotherapy and radiotherapy. While VEGF and mTOR targeted therapies have shown clinical activity, their effects are variable and short-lived, underscoring the need for improved treatment strategies for RCC.

Further, biomarkers that are predictive of Src kinase activity and that therefore predict that a Src kinase inhibitor will be useful in treatment of cancer are needed.

Disclosed herein is a personalized medicine approach that stratifies cancer patients (such as RCC patients) based on the use of a HIF regulated VHL-PTP1B-Src signaling axis in patients with VHL-positive cancer.

The disclosed test stratifies cancer patients using biomarker profiling for expression one or more of VHL, Src, CA-IX, phosphorylated FAK, PTP1B, HIF-1α and/or HIF-2α. thereby identifying patients that are more likely to respond to Src inhibitors. Thus, disclosed herein are methods for identifying subjects with a cancer such as a RCC that would benefit from treatment with an agent that inhibits Src kinase.

The disclosed methods include detecting expression of one or more of Von Hippel Lindau (VHL), Src, PTP1B, pFAK, HIF-1α, and/or CA-IX in a sample obtained from a subject and comparing the expression of the gene product(s) to a threshold level of expression, wherein the threshold level of expression has been predetermined to signify that the subject will benefit from treatment with a Src inhibitor.

Expression of VHL, Src, PTP1B, and pFAK that exceeds the threshold level of expression in the sample is an indication that the tumor would be sensitive to an agent that inhibits Src kinase. Expression can be measured alone or in combination any other marker. In particular examples, the cancer is renal cell carcinoma or transitional cell carcinoma of the bladder.

Expression of HIF-1α and CA-IX that is below the threshold level of expression in the sample is an indication that the tumor would be sensitive to an agent that inhibits Src kinase. Expression of HIF-1α and/or CA-IX may be determined alone or in combination with tests for VHL, Src, PTP1B and/or pFAK or any other marker.

The Src inhibitor may be any agent that antagonizes the activity and/or expression of Src such as a small molecule, an inhibitory RNA, or an antibody that specifically binds Src in such a way to inhibit its activity. In specific examples, the inhibitor of src is a small molecule inhibitor of src, such as one or more of saracatinib (AZD0530), dasatinib (BMS-354825), AP23846, UCS15A, bosutinib (SKI-606), and KX2-391 (KXO1).

Methods of treating a subject with cancer are also disclosed. These methods include performing one of the disclosed tests upon a sample of a tumor from the subject and, based on the result of the test, administering to the subject an effective amount of a Src inhibitor.

DESCRIPTION OF THE DRAWINGS

FIG. 1A: Lysates from parallel cultures of serum-stimulated SN12C and SN12C-shVHL cells were labeled with iTRAQ 8-plex reagent and phosphotyrosine containing peptides were subjected to immobilized metal affinity chromatography tandem MS analysis. Quantitative phosphorylation profiles were generated for 22 phosphorylation sites on the indicated proteins. Mean ratios to SN12C control were log transformed and partitioned according to similarity of phosphorylation status by unsupervised, hierarchical clustering using Cluster 3.0 and visualized with TreeView. The heatmap is pseudo-colored to indicate direction and magnitude of mean ratios relative to SN12C control cells. SF, serum free; FBS, fetal bovine serum). See also Table 1 and Methods.

FIG. 1B: Src was immunoprecipitated from SN12C and SN12C shVHL cells and Src kinase activity was measured in the absence or presence of 50 nM dasatinib as described in methods. Data are presented as the mean CPM±S.D. from three independent studies assayed in duplicate. (Lower panel) Corresponding western blot shows control (no primary antibody) or Src immunoprecipitates and relative Src expression in SN12C and SN12C-shVHL cells. The amount of Src was quantified with Image J and presented numerically as the fold-change.

FIG. 1C: Immunohistochemistry for Src from samples from 3 representative RCC patients with strong (left and center panels) or weak expression (right panel). Arrowheads indicate membranous localization. Scale bar, 20 μm.

FIG. 1D: Kaplan-Meier survival analysis of clear cell RCC patients with tumors expressing weak or strong Src immunohistochemical staining (n=117, p=0.0367).

FIGS. 2A-2E show that the small molecule Src inhibitor dasatinib induces growth arrest in VHL-WT RCC cells FIG. 2A: $5 \times 10^4$ VHL-WT (VHL+) SN12C and ACHN or shVHL cells were treated with vehicle, 25, 50 or 100 nM dasatinib 24 hours after seeding. Effect of dasatinib on cell growth was monitored by cell count at indicated time points (n=3). Data are presented as the mean±S.D.

FIG. 2B: Subconfluent SN12C and ACHN VHL-WT (VHL+) or shVHL cells were treated with the indicated doses of dasatinib for 48 hours and labeled with 10 μM BrdU for 30 minutes prior to harvesting. Cells were dual-stained with FITC-BrdU antibody and PI and analyzed by flow cytometry.

FIG. 2C: Sub-confluent SN12C and ACHN VHL-WT (VHL⁺) or shVHL cells were treated with vehicle, 25, 50 or 100 nM dasatinib. Inhibitory effect of dasatinib on Src kinase activity was assessed by flow cytometry using anti-pY419 Src (FIG. 2C1). Levels of total and phospho-specific forms of Src and FAK were determined by immunoblotting (FIG. 2C2). Tubulin used as loading control.

FIG. 2D: Nude mice bearing SN12C and SN12C shVHL xenografts were treated daily with vehicle or 10 mg/kg of dasatinib by oral gavage. Fold increase in tumor volume is plotted against days following tumor injection. Xenografts were analyzed by immunoblot for levels of pSrc Y419 and total Src. α-tubulin, loading control. Data are presented as the mean±S.E.M. of six mice in each group.

FIG. 2E: Xenograft tumors from FIG. 2D were analyzed for cell proliferation and apoptosis by immunohistochemistry against Ki-67 and cleaved-caspase-3, respectively and subjected to quantitative image analysis. Data are presented as the mean±S.E.M. (n=11-21).

FIG. 3A: SN12C, SN12C-shSrc, or SN12-shSrc cells expressing shRNA-resistant Src (Rescue) were treated with vehicle, 25, 50 or 100 nM dasatinib for 96 hours and then cell growth was analyzed by cell count. Data are presented as the mean±S.D. (n=3). Src expression or knockdown was verified by immunoblot with antibodies against total and pY419 Src. α-tubulin, loading control.

FIGS. 3B and 3C: SN12C cells (Control) or SN12C cells stably expressing (FIG. 3B) dasatinib-resistant Src (Src T338I), or (FIG. 3C) v-Src, were treated with vehicle alone or with 25 or 50 nM dasatinib for 96 hours and then cell growth was analyzed by cell count. Data are presented as the mean±S.D. (n=3). The levels of total Src and pY419 Src were assessed by immunoblot. α-tubulin and β-actin, loading controls.

FIG. 3D: SCID mice bearing SN12C and SN12C v-Src xenografts were treated daily with vehicle or 10 mg/kg of dasatinib by oral gavage. Percent (%) increase in tumor volume is plotted against days following tumor injection. Data are presented as the mean±S.E.M. (n=24).

FIGS. 4A-4G show that HIF-α and PTP1B are involved in dasatinib-induced growth inhibition.

FIG. 4A: SN12C and ACHN cells stably expressing mutant HIF-1α (P564A) or HIF-2α (P405A;P531A) were treated with vehicle, 25, 50 or 100 nM dasatinib for 96 hours and then cell growth was analyzed by cell count. Data are presented as the mean±S.D. (n=3, **p<0.01). Overexpression of the mutant forms of HIF-α were validated by immunoblot. α-tubulin, loading control.

FIG. 4B: SN12C and ACHN cells stably expressing mutant HIF-1α (P564A) or HIF-2α (P405A;P531A) were treated with vehicle, 25, 50 or 100 nM dasatinib for 48 hours and then analyzed for BrdU incorporation by flow cytometry as described in Methods.

FIG. 4C: SN12C and ACHN cells stably expressing constitutively stable HIF-1α P564A (SN12C HIF-1α) or HIF-2α P405A; P531A (SN12C HIF-2α) were treated with vehicle alone or with, 25, 50 or 100 nM dasatinib for 18 hours. Levels of total Src and FAK as well as pSrc Y419 and pFAK Y576/577 were determined by immunoblot. α-tubulin, loading control.

FIG. 4D: Lysates from the SN12C and ACHN mutant HIF-α overexpressing lines, shVHL cells and the parental cell lines were examined for expression of total and/or phospho-specific forms of Src, FAK, ERK1/2, STAT3, CSK and PTP1B by immunoblot. α-tubulin, loading control.

FIG. 4E: The levels of PTP1B mRNA were measured by real-time PCR in SN12C and ACHN HIF-α overexpressing and shVHL cell lines. Levels of PTP1B mRNA in the parental cell lines were normalized to 1. Data are presented as the mean±S.D. (n=3).

FIG. 4F: SN12C cells expressing an shRNA targeting PTP1B (shPTP1B) were analyzed by immunoblot for expression levels of total and/or phospho-specific forms of PTP1B, Src, FAK, STAT3, ERK1/2 and α-tubulin.

FIG. 4G: SN12C or shPTP1B cells were treated with vehicle, 25, 50 or 100 nM dasatinib and cell growth was assessed by cell count. Data are presented as the mean±S.D. (n=3).

FIG. 5A: Quantitative assessment of VHL, PTP1B, Src and HIF-2α expression by immunostaining of RCC TMA. Representative staining images from a patient with strong VHL protein expression (top panel) and from a patient with weak VHL expression (bottom panel) are shown. Corresponding markup images of the color deconvolution algorithm with intensity ranges are shown. For HIF-2α, the nuclear immunostaining algorithm was applied. Scale bar is 50 μm.

FIG. 5B: Spearman Rho correlation coefficients among the biomarkers are listed in the boxes. Red indicates positive correlation and blue indicates negative correlation. P values for these correlations are represented as follows: *p<0.05; p<0.001; *p<0.0001 (n=131).

FIG. 5C: Comparison between Src and VHL protein expression in the RCC tissue microarray FIG. 5D: Scatter plot of the VHL and Src scores generated from automated image analysis intensity algorithm. The vertical lines represent 5th percentile and median VHL scores, corresponding to thresholds for negative and weak expression, respectively. The horizontal line represents the median for the Src score, where levels below are considered weak expression and levels above are considered strong expression. The upper right (shaded) quadrant depicts the molecular phenotype of tumors with both strong VHL and strong Src expression.

FIG. 7A is a bar graph depicting the data from the experiment described above.

FIG. 7B is an image of the immunoblot.

FIG. 13A: Changes in levels of PTP1B and HIF1α in SN12C and ACHN cells were monitored by immunoblot following exposure to hypoxia (1% oxygen) for the indicated times. α-tubulin, loading control.

FIG. 13B: Xenograft tumors from SN12C and SN12C shVHL cells were immunostained with pimonidazole (Hypoxyprobe) and PTP1B. Corresponding markup images of the color deconvolution algorithm with intensity ranges are shown. Scale bar is 100 μm.

SEQUENCE LISTING

Figure 1A:
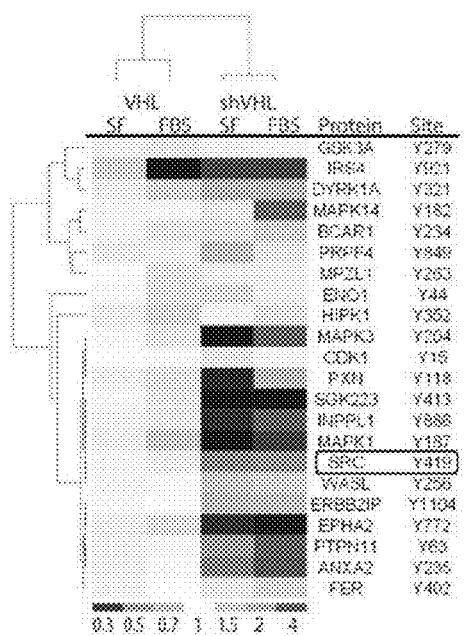
FIGS. 1A-1D show that Src is expressed in RCC and is associated with poor outcome.

SEQ ID NO: 1 is a nucleotide sequence representing a coding sequence of VHL.
SEQ ID NO: 2 is a nucleotide sequence representing a coding sequence of PTP1B.
SEQ ID NO: 3 is a nucleotide sequence representing a coding sequence of HIF-1α.
SEQ ID NO: 4 is a nucleotide sequence representing a coding sequence of FAK.
SEQ ID NO: 5 is a nucleotide sequence representing a coding sequence of CA-IX.
SEQ ID NO: 6 is a nucleotide sequence representing a coding sequence of Src.
SEQ ID NO: 7 is a protein sequence representing VHL.
SEQ ID NO: 8 is a protein sequence representing PTP1B.
SEQ ID NO: 9 is a protein sequence representing HIF-1α.
SEQ ID NO: 10 is a protein sequence representing FAK.
SEQ ID NO: 11 is a protein sequence representing CA-IX.
SEQ ID NO: 12 is a protein sequence representing Src.

DETAILED DESCRIPTION

I. Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), 5 The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes."

In addition, the materials, methods, and examples are illustrative only and not intended to be limiting. In order to facilitate review of the various embodiments of the disclosure, the following explanations of specific terms are provided:

Aberrant activity of a tyrosine kinase: Inappropriate or uncontrolled activation of a tyrosine kinase, such as Src, for example by over-expression, upstream activation (for example, by upstream activation of a protein that affect a tyrosine kinase), and/or mutation (for example a truncation, deletion, insertion and/translocation which increases the activity, such as but not limited to, kinase activity of a tyrosine kinase), which can lead to uncontrolled cell growth, for example in cancer, such as renal cell carcinoma (RCC). In some examples, aberrant activity of a tyrosine kinase is a higher rate of kinase activity than the unmutated tyrosine kinase. In some examples, aberrant activity of a tyrosine kinase is a lower rate of kinase activity than the unmutated tyrosine kinase. Other examples of aberrant activity of a tyrosine kinase include, but are not limited to, mislocalization of the tyrosine kinase, for example mislocalization in an organelle of a cell or mislocalization at the cell membrane relative to the unmutated tyrosine kinase.

Administration: To provide or give a subject an agent, such as a composition that targets/inhibits Src kinase, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Amplifying a nucleic acid molecule: To increase the number of copies of a nucleic acid molecule, such as a gene or fragment of a gene, for example a region of a gene that encodes a tumor biomarker, such as a RCC tumor biomarker. The resulting products are called amplification products.

An example of in vitro amplification is the polymerase chain reaction (PCR). Other examples of in vitro amplification techniques include quantitative real-time PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

A commonly used method for real-time quantitative polymerase chain reaction involves the use of a double stranded DNA dye (such as SYBR Green I® dye). For example, as the amount of PCR product increases, more SYBR Green I dye binds to DNA, resulting in a steady increase in fluorescence. SYBR Green binds to double stranded DNA, but not to single stranded DNA. In addition, SYBR Green fluoresces strongly at a wavelength of 497 nm when it is bound to double stranded DNA, but does not fluoresce when it is not bound to double stranded DNA. As a result, the intensity of fluorescence at 497 nm may be correlated with the amount of amplification product present at any time during the reaction. The rate of amplification may in turn be correlated with the amount of template sequence present in the initial sample. Generally, Ct values are calculated similarly to those calculated using the TaqMan® system. Because the probe is absent, amplification of the proper sequence may be checked by any of a number of techniques. One such technique involves running the amplification products on an agarose or other gel appropriate for resolving nucleic acid fragments and comparing the amplification products from the quantitative real time PCR reaction with control DNA fragments of known size.

Another commonly used method is real-time quantitative TaqMan® PCR (Applied Biosystems). This type of PCR has reduced the variability traditionally associated with quantitative PCR, thus allowing the routine and reliable quantification of PCR products to produce sensitive, accurate, and reproducible measurements of levels of gene expression. the PCR step can use any of a number of thermostable DNA-dependent DNA polymerases, it typically employs a Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used.

Two oligonucleotide primers are used to generate an amplicon typical of a PCR reaction. A third oligonucleotide, or probe, is designed to detect nucleotide sequence located between the two PCR primers. The probe is nonextendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

Examples of fluorescent labels that may be used in quantitative PCR include but need not be limited to: HEX, TET, 6-FAM, JOE, Cy3, Cy5, ROX TAMRA, and Texas Red. Examples of quenchers that may be used in quantitative PCR include, but need not be limited to TAMRA (which may be used as a quencher with HEX, TET, or 6-FAM), BHQ1, BHQ2, or DABCYL. TAQMAN® RT-PCR can be performed using commercially available equipment, such as, for example, ABI PRISM 7700® Sequence Detection System™ (Perkin-Elmer-Applied Biosystems, Foster City, Calif., USA), or Lightcycler (Roche Molecular Biochemicals, Mannheim, Germany).

In one embodiment, the 5' nuclease procedure is run on a real-time quantitative PCR device such as the ABI PRISM 7700® Sequence Detection System. The system includes of thermocycler, laser, charge-coupled device (CCD), camera and computer. The system amplifies samples in a 96-well format on a thermocycler. During amplification, laser-induced fluorescent signal is collected in real time through fiber optic cables for all 96 wells, and detected at the CCD. The system includes software for running the instrument and for analyzing the data.

In some examples, 5'-nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR can be performed using an internal standard. The ideal internal standard is expressed at a constant level among different tissues, and is unaffected by the experimental treatment. RNAs most frequently used to normalize patterns of gene expression are the mRNA products of housekeeping genes.

Antibody: A polypeptide including at least a light chain or heavy chain immunoglobulin variable region which specifically recognizes and binds an epitope of an antigen (such as a molecule associated with sensitivity to a src inhibitor) or a fragment thereof. Antibodies are composed of a heavy and a light chain, each of which has a variable region, termed the variable heavy (VH) region and the variable light (VL) region. Together, the VH region and the VL region are responsible for binding the antigen recognized by the antibody. In some examples, antibodies of the present disclosure include those that are specific for Src, VHL, HIF-1α, HIF-2α, PTP1B, and CA-IX.

The term antibody includes intact immunoglobulins, as well the variants and portions thereof, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies, heteroconjugate antibodies (such as, bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Anti-proliferative activity: An activity of a molecule, for example a small molecule, an inhibitory RNA, and the like, which reduces proliferation of at least one cell type, but which may reduce the proliferation (either in absolute terms or in rate terms) of multiple different cell types (e.g., different cell lines, different species, etc.). In specific embodiments, the anti-proliferative activity of small molecule, such as inhibitor of Src kinase will be apparent against renal cells obtained from a subject diagnosed with RCC, such as VHL+RCC.

Antisense compound: Refers to an oligomeric compound that is at least partially complementary to the region of a target nucleic acid molecule (such as a Src gene product) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression. Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound. In particular examples, the antisense compound is an antisense oligonucleotide, siRNA or ribozyme.

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis.

In certain example arrays, one or more molecules (such as an antibody or peptide) will occur on the array a plurality of times (such as twice), for instance to provide internal controls. The number of addressable locations on the array can vary, for example from at least one, to at least 2, to at least 3, at least 4, at least 5, at least 6, at least 10, at least 20, at least 30, at least 50, at least 75, at least 100, at least 150, at least 200, at least 300, at least 500, least 550, at least 600, at least 800, at least 1000, at least 10,000, or more. In some examples, arrays include positive and/or negative controls, such as probes that bind housekeeping genes. In particular examples, an array includes nucleic acid molecules, such as oligonucleotide sequences that are at least 15 nucleotides in length, such as about 15-40 nucleotides in length. In particular examples, an array includes oligonucleotide probes or primers which can be used to detect nucleotides that encode tumor biomarker sequences (including RCC biomarkers). In an example, the array is a commercially available array such as Human Genome GeneChip® arrays from Affymetrix (Santa Clara, Calif.).

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays may be computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins. In some examples, an array contains antibodies to tumor biomarkers, such as the disclosed RCC biomarkers.

Tissue microarrays include a plurality of sections of normal and/or diseased tissue (such as RCC tissue with or without associated normal adjacent tissue) on a single microscope slide. A tissue microarray allows for the analysis of expression of one or more markers on a large number of tumors in a single experiment.

Binding or stable binding: An association between two substances or molecules, such as the association of an antibody with a peptide, nucleic acid to another nucleic acid, or the association of a protein with another protein or nucleic acid molecule. Binding can be detected by any procedure known to one skilled in the art, such as by physical or functional properties of the target:oligonucleotide complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt. In another example, the method involves detecting a signal, such as a detectable label, present on one or both nucleic acid molecules (or antibody or protein as appropriate).

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

Biological signaling pathway: A systems of proteins, such as tyrosine kinases, and other molecules that act in an orchestrated fashion to mediate the response of a cell toward internal and external signals. In some examples, biological signaling pathways include tyrosine kinase proteins, such as Src, which can propagate signals in the pathway by selectively phosphorylating downstream substrates. In some examples, a biological signaling pathway is dysregulated and functions improperly, which can lead to aberrant signaling and in some instances hyper-proliferation of the cells with the aberrant signaling. In some examples, dysregulation of a biological signaling pathway can result in a malignancy, such as cancer, for example RCC, such as VHL+RCC. A Src biological signaling pathway is a signaling pathway, in which Src plays a role, for example by phosphorylation of downstream targets.

Biomarker: Molecular, biological or physical attributes that characterize a physiological or cellular state and that can be objectively measured to detect or define disease progression or predict or quantify therapeutic responses. A biomarker is a characteristic that is objectively measured and evaluated as an indicator of normal biologic processes, pathogenic processes, or pharmacologic responses to a therapeutic intervention. A biomarker may be any molecular structure produced by a cell or organism. A biomarker may be expressed inside any cell or tissue; accessible on the surface of a tissue or cell; structurally inherent to a cell or tissue such as a structural component, secreted by a cell or tissue, produced by the breakdown of a cell or tissue through processes such as necrosis, apoptosis or the like; or any combination of these. A biomarker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination.

A biomarker may be represented by the sequence of a nucleic acid from which it can be derived or any other chemical structure. Examples of such nucleic acids include miRNA, tRNA, siRNA, mRNA, cDNA, or genomic DNA sequences including any complimentary sequences thereof.

One example of a biomarker is a gene product, such as a protein or RNA molecule encoded by a particular DNA sequence. In one example, a biomarker is a protein or nucleic acid sequence of a corresponding gene that is an indicator that a tumor such as a renal cell carcinoma is sensitive to treatment with a Src kinase inhibitor such as VHL, src, HIF-1α, HIF-2α, PTP1B, or CA-IX.

Cancer: A disease or condition in which abnormal cells divide without control and are able to invade other tissues. Cancer cells spread to other body parts through the blood and lymphatic systems. Cancer is a term for many diseases; there are more than 100 different types of cancer in humans. Most cancers are named after the organ in which they originate. For instance, a cancer that begins in the colon is called a colon cancer. However, the characteristics of a cancer, especially with regard to the sensitivity of the cancer to therapeutic compounds, are not limited to the organ in which the cancer originates.

Cancer is a malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc.

"Metastatic disease" or "metastasis" refers to cancer cells that have left the original tumor site and migrate to other parts of the body for example via the bloodstream or lymph system. The "pathology" of cancer includes all phenomena that compromise the wellbeing of the subject. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

Carbonic anhydrase 9 (CA-IX): Carbonic anhydrases (CAs) are a large family of zinc metalloenzymes that catalyze the reversible hydration of carbon dioxide. They participate in a variety of biological processes, including respiration, calcification, acid/base balance, bone resorption, and the formation of aqueous humor, cerebrospinal fluid, saliva, and gastric acid. They show extensive diversity in tissue distribution and in their subcellular localization. CA IX is a transmembrane protein and the only tumor associated carbonic anhydrase isoenzyme known. It is expressed in all clear-cell renal cell carcinoma, but is not detected in normal kidney or most other normal tissues. It may be involved in cell proliferation and transformation.

cDNA (complementary DNA): A piece of DNA lacking internal, non-coding segments (introns) and regulatory sequences which determine transcription. cDNA can be synthesized by reverse transcription from messenger RNA extracted from cells.

Chemotherapeutic agent or Chemotherapy: Any chemical agent with therapeutic usefulness in the treatment of diseases characterized by abnormal cell growth. Such diseases include tumors, neoplasms, and cancer as well as diseases characterized by hyperplastic growth. In one embodiment, a chemotherapeutic agent is an agent of use in treating cancer, such as RCC, such as small molecule inhibitor of Src kinase. In one example, a chemotherapeutic agent is a radioactive compound. One of skill in the art can readily identify a chemotherapeutic agent of use (see for example, Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy.

Regimens used in treating RCC include the following (all publications in this section are hereby incorporated by reference herein):

High-dose IL-2 and subcutaneous low dose IL-2 (Yang J C et al, *J Clin Oncol* 21, 3127-3132 (2003);) interferon alpha-2A (Negrier S et al, *New Engl J Med* 338, 1278-1278 (1998);) fluorouracil+gemcitabine (Rini B I et al, *J Clin Oncol* 18, 2419-2426 (2000); sorafenib (Escudier B et al, *Proc Am Soc Clin Oncol* 23, 16S Part 1 380S, abs LBA4510 (2005);) sunitinib (Motzer R J et al, *Proc Am Soc Clin Oncol* 23 16S Part 1 380S, abs 4508 (2005).) Combination chemotherapy is the administration of more than one agent to treat cancer.

Contacting: Placement in direct physical association, including both a solid and liquid form. Contacting can occur in vitro with isolated cells or tissue or in vivo by administering to a subject.

Determining a level of expression of a biomarker: Quantitatively determining expression of a nucleic acid or protein biomarker by routine methods known in the art.

Diagnostic: Identifying the presence or nature of a pathologic condition, such as, but not limited to cancer, such as RCC, for example VHL+RCC. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (for example severity) of a pathologic condition, such as RCC, for example VHL+RCC.

Downregulated or inactivation: When used in reference to the expression of a nucleic acid molecule, such as a gene, refers to any process which results in a decrease in production of a gene product. A gene product can be RNA (such as mRNA, rRNA, tRNA, and structural RNA) or protein. Therefore, gene downregulation or deactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability. Gene downregulation includes any detectable decrease in the production of a gene product. In certain examples, production of a gene product decreases by at least 2-fold, for example at least 3-fold or at least 4-fold, as compared to a control (such an amount of gene expression in a normal cell). In one example, a control is a relative amount of gene expression or protein expression in a biological sample taken from a subject who does not have cancer, such as RCC.

Effective amount: An amount of agent, such as nucleic acid vaccine or other agent that is sufficient to generate a desired response, such as reduce or eliminate a sign or symptom of a condition or disease, such as cancer, for example RCC. When administered to a subject, a dosage will generally be used that will achieve target tissue concentrations (for example, in lymphocytes) that has been shown to achieve in vitro inhibition of viral replication. In some examples, an "effective amount" is one that treats (including prophylaxis) one or more symptoms and/or underlying causes of any of a disorder or disease, for example cancer, such as RCC. In one example, an effective amount is a therapeutically effective amount. In one example, an effective amount is an amount that prevents one or more signs or symptoms of a particular disease or condition from developing, such as one or more signs or symptoms associated with such as cancer, for example RCC.

Focal adhesion kinase (FAK): A cytoplasmic protein tyrosine kinase which is involved in calcium-induced regulation of ion channels and activation of the map kinase signaling pathway. The encoded protein may represent a signaling intermediate between neuropeptide-activated receptors or neurotransmitters that increase calcium flux and the downstream signals that regulate neuronal activity. The encoded protein undergoes rapid tyrosine phosphorylation and activation in response to increases in the intracellular calcium concentration, nicotinic acetylcholine receptor activation, membrane depolarization, or protein kinase C activation. This protein has been shown to bind CRK-associated substrate, nephrocystin, GTPase regulator associated with FAK, and the SH2 domain of GRB2. The encoded protein is a member of the FAK subfamily of protein tyrosine kinases but lacks significant sequence similarity to kinases from other subfamilies.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (detects sequences that share at least 90% identity)
 Hybridization: 5×SSC at 65° C. for 16 hours
 Wash twice: 2×SSC at room temperature (RT) for 15 minutes each
 Wash twice: 0.5×SSC at 65° C. for 20 minutes each
High Stringency (detects sequences that share at least 80% identity)
 Hybridization: 5×–6×SSC at 65° C.-70° C. for 16-20 hours
 Wash twice: 2×SSC at RT for 5-20 minutes each
 Wash twice: 1×SSC at 55° C.-70° C. for 30 minutes each
Low Stringency (detects sequences that share at least 50% identity)
 Hybridization: 6×SSC at RT to 55° C. for 16-20 hours
 Wash at least twice: 2×–3×SSC at RT to 55° C. for 20-5 30 minutes each.

Hypoxia-inducible factors (HIFs): Transcription factors that respond to changes in available oxygen in the cellular environment, specifically, to decreases in oxygen, or hypoxia. Examples of HIFs include Hypoxia inducible factor 1, alpha (HIF-1α) and Hypoxia inducible factor 2, alpha (HIF-2α).

Immunohistochemistry: A technique used to identify a specific molecule in different types of tissue, including cancer tissue. Tissues in a tissue section (such as a paraffin, fixed, unfixed, or frozen section) on a microscope slide are treated with an antibody that binds to the specific molecule. The antibodies are conjugated to a label that renders tissues that bound to the label visible under a microscope. Examples of labels that may be used in immunohistochemistry include fluorescent dyes, radioisotopes, metals (such as colloidal gold,) and enzymes that produce a local color change upon interaction with a substrate. Multiple molecules may be assessed in the same tissue using differentially labeled antibodies—for example, by using a first antibody specific for a first molecule conjugated to a label that fluoresces at a particular wavelength and a second antibody specific for a second molecule conjugated to a label that fluoresces at a different wavelength than the one conjugated to the first molecule.

Inhibitor: Any chemical compound, nucleic acid molecule, peptide such as an antibody, specific for a gene product that can reduce activity of a gene product or directly interfere with expression of a protein, such as Src. An inhibitor can inhibit the activity of a protein that is encoded by a gene either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein. Furthermore, an inhibitor of the disclosure can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization.

Inhibit: To reduce to a measurable extent, for example, to reduce enzymatic activity. In some examples, the kinase activity of a Src kinase is inhibited, for example using a small molecule inhibitor of Src or an siRNA that inhibits the expression of Src.

Inhibiting or treating a disease: Inhibiting the full development of a disease or condition, for example, in a subject who is at risk for a disease such cancer, for example RCC, such as VHL+RCC. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other clinical or physiological parameters associated with a particular disease. A "prophylactic" treatment is a treatment administered to a subject who does not exhibit signs of a disease or exhibits only early signs for the purpose of decreasing the risk of developing pathology.

Kinase: An enzyme that catalyzes the transfer of a phosphate group from one molecule to another. Kinases play a role in the regulation of cell proliferation, differentiation, metabolism, migration, and survival. A "tyrosine kinase" transfers phosphate groups to a hydroxyl group of a tyrosine in a polypeptide. In some examples, a kinase is a SRC tyrosine kinase. Receptor protein tyrosine kinases (PTKs) contain a single polypeptide chain with a transmembrane segment. The extracellular end of this segment contains a high affinity ligand-binding domain, while the cytoplasmic end comprises the catalytic core and the regulatory sequences.

Non-receptor tyrosine kinases, such as Src, can be located in the cytoplasm as well as in the nucleus. They exhibit distinct kinase regulation, substrate phosphorylation, and function. A "preferential" inhibition of a kinase refers to decreasing activity of one kinase, such as Src, more than inhibiting the activity of a second kinase, such as a mitogen activated protein kinase (MAPK) or another tyrosine kinase.

Mass spectrometry: A method wherein, a sample is analyzed by generating gas phase ions from the sample, which are then separated according to their mass-to-charge ratio (m/z) and detected. Methods of generating gas phase ions from a sample include electrospray ionization (ESI), matrix-assisted laser desorption-ionization (MALDI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), Fourier-transform ion cyclotron resonance (FT-ICR) analyzers, and combinations thereof (for example, a quadrupole-time-of-flight analyzer, or Q-TOF analyzer). Prior to separation, the sample may be subjected to one or more dimensions of chromatographic separation, for example, one or more dimensions of liquid or size exclusion chromatography or gel-electrophoretic separation.

Pharmaceutically acceptable carriers: The pharmaceutically acceptable carriers of use are conventional. Remington's Pharmaceutical Sciences, by E.W. Martin, Mack Publishing Co., Easton, Pa., 19th Edition, 1995, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phospho-peptide or phospho-protein: A peptide or protein in which one or more phosphate moieties are covalently linked to amino acid residue or amino acid analogs. A peptide can be phosphorylated at multiple or single sites. Sometimes it is desirable for the phospho-peptide to be phosphorylated at one site regardless of the presence of multiple potential phosphorylation sites. In vivo the transfer of a phosphate to a peptide is accomplished by a kinase exhibiting kinase activity, for example a tyrosine kinase, such as Src transfers a phosphate to a tyrosine residue of a substrate peptide or protein.

Polypeptide: Any chain of amino acids, regardless of length or posttranslational modification (such as glycosylation, methylation, ubiquitination, phosphorylation, or the like). In one embodiment, a polypeptide is a Src polypeptide. "Polypeptide" is used interchangeably with peptide or protein, and is used to refer to a polymer of amino acid residues. A "residue" refers to an amino acid or amino acid mimetic incorporated in a polypeptide by an amide bond or amide bond mimetic.

Protein tyrosine phosphatase 1B (PTP1B): The protein encoded by this gene is the founding member of the protein tyrosine phosphatase (PTP) family, which was isolated and identified based on its enzymatic activity and amino acid sequence. PTPs catalyze the hydrolysis of the phosphate monoesters specifically on tyrosine residues. Members of the PTP family share a highly conserved catalytic motif, which is essential for the catalytic activity. PTPs are known to be signaling molecules that regulate a variety of cellular processes including cell growth, differentiation, mitotic cycle, and oncogenic transformation. This PTP has been shown to act as a negative regulator of insulin signaling by dephosphorylating the phosphotryosine residues of insulin receptor kinase. This PTP was also reported to dephosphorylate epidermal growth factor receptor kinase, as well as JAK2 and TYK2 kinases, which implicated the role of this PTP in cell growth control, and cell response to interferon stimulation.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides.

Renal cell carcinoma (RCC): The most common form of kidney cancer arising from the proximal renal tubule. RCC is also known as hypernephroma. Initial treatment is most commonly a radical or partial nephrectomy and remains the mainstay of curative treatment. Where the tumor is confined to the renal parenchyma, the 5-year survival rate is 60-70%, but this is lowered considerably where metastases have spread. RCC is generally resistant to radiation therapy and chemotherapy, although some cases respond to immunotherapy.

RCC is classified into 5 different types:
1. Clear cell type (65% of RCC)
Cell origin: proximal tubule
Cytogenetic abnormalities: chromosome 3p deletions, mutations of VHL gene (tumor suppressor gene)
2. Papillary cell type (Chromophil) (15% of RCC)
Cell origin: proximal tubule
Cytogenetic abnormalities: trisomies of chromosomes 3q, 7, 12, 16, 17, 20; loss of Y chromosome
3. Chromophobe cell type (10% of RCC)
Cell origin: intercalated cell of cortical collecting duct
Cytogenetic abnormalities: monosomies of chromosomes 1, 2, 6, 10, 13, 17, and 21; hypodiploidy
4. Oncocytoma (5% of RCC)
Cell origin: Intercalated cell of cortical collecting duct
Cytogenetic abnormalities: loss of chromosomes 1 and Y
5. Unclassified cell type (5% of RCC): Sarcomas, collecting duct tumors, etc.

Sample: A sample, such as a biological sample, is a sample obtained from a plant or animal subject. As used herein, biological samples include all clinical samples useful for detection of the sensitivity of a subject to inhibitors of Src kinase, including, but not limited to, cells, tissues, and bodily fluids, including tissues that are, for example, unfixed, frozen, fixed in formalin and/or embedded in paraffin. In particular embodiments, the biological sample is obtained from a subject, such as in the form of blood or a fraction thereof such as leukocytes, lymphocytes, and/or mononuclear cells. In one example, a sample includes a tissue biopsy obtained from a subject with a tumor, such as RCC.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls.

in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost 5 of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a protein.

When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Short interfering RNA (siRNA): A double stranded nucleic acid molecule capable of RNA interference or "RNAi." (See, for example, Bass Nature 411: 428-429, 2001; Elbashir et al., Nature 411: 494-498, 2001; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914.) As used herein, siRNA molecules need not be limited to those molecules containing only RNA, but further encompasses chemically modified nucleotides and non-nucleotides having RNAi capacity or activity. In an example, a siRNA molecule is one that reduces or interferes with the biological activity of Src.

Small molecule: A molecule, typically with a molecular weight less than about 1000 Daltons, or in some embodiments, less than about 500 Daltons, wherein the molecule is capable of modulating, to some measurable extent, an activity of a target molecule such as inhibiting the activity of a kinase, such as the Src kinase.

Specific Binding Agent: An agent that binds substantially or preferentially only to a defined target such as a protein, enzyme, polysaccharide, oligonucleotide, DNA, RNA, recombinant vector or a small molecule. In an example, a "specific binding agent" is capable of binding to at least one of the disclosed RCC biomarkers. In other examples, the specific binding agent is capable of binding to a downstream factor regulated by at least one of the disclosed RCC biomarkers. Thus, a nucleic acid-specific binding agent binds substantially only to the defined nucleic acid, such as RNA, or to a specific region within the nucleic acid. For example, a "specific binding agent" includes an antisense compound (such as an antisense oligonucleotide, siRNA, miRNA, shRNA or ribozyme) that binds substantially to a specified RNA.

A protein-specific binding agent binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide, as well as immunologically effective portions ("fragments") thereof.

The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Src: A proto-oncogenic tyrosine kinase that belongs to a family of nonreceptor tyrosine kinases called Src family kinases Subject: A living multicellular vertebrate organism, a category that includes, for example, mammals and birds. A "mammal" includes both human and non-human mammals, such as mice. In some examples, a subject is a patient, such as a patient diagnosed with RCC, such as a patient diagnosed with Von Hippie Lindau positive 5 VHL+RCC. Thus, the terms patient or subject can be used to refer to one diagnosed with RCC, such as VHL+RCC.

Substrate: A molecule that is acted upon by an enzyme, such as Src. A substrate binds with the enzyme's active site, and an enzyme-substrate complex is formed. In some examples, the enzyme catalyses the incorporation of an atom or other molecule into the substrate, for example a kinase can incorporate a phosphate into the substrate, such as a peptide, thus forming a phospho-substrate.

Target sequence: A sequence of nucleotides located in a particular region in the human genome that corresponds to a desired sequence, such as a tumor biomarker sequence, including a RCC biomarker sequence. The target can be for instance a coding sequence; it can also be the non-coding strand that corresponds to a coding sequence.

Threshold level of expression: Any level of expression of a biomarker that signals a diagnostic, prognostic, or therapeutic outcome. A threshold level of expression of VHL, Src, pFAK, PTP1B, CA-IX, HIF-1α, or HIF-2α that signifies that a subject may benefit from treatment with a src inhibitor may be readily calculated by one of skill in the art in light of this disclosure for any method of assessing the expression of VHL, Src, pFAK, PTP1B, CA-IX, HIF-1α, or HIF-2α.

Tissue: A plurality of functionally related cells. A tissue can be a suspension, a semi-solid, or solid. Tissue includes cells collected from a subject such as the kidneys or a portion thereof.

Tumor: All neoplastic cell growth and proliferation, whether malignant or benign, and all pre-cancerous and cancerous cells and tissues.

Upregulated or activation: When used in reference to the expression of a nucleic acid molecule, such as a gene, refers to any process which results in an increase in production of a gene product. A gene product can be RNA (such as mRNA, rRNA, tRNA, and structural RNA) or protein. Therefore, gene upregulation or activation includes processes that increase transcription of a gene or translation of mRNA.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level.

Examples of processes that increase translation include those that increase translational initiation, those that increase translational elongation and those that increase mRNA stability. Gene upregulation includes any detectable increase in the production of a gene product. In certain examples, production of a gene product increases by at least 2-fold, for example at least 3-fold or at least 4-fold, as compared to a control (such an amount of gene expression in a normal cell or a reference value). In one example, a control is a relative amount of gene expression in a biological sample, such as a tissue biopsy obtained from a subject that does not have RCC or a reference value.

Von Hippel—Lindau tumor suppressor (VHL): A protein that in humans is encoded by the VHL gene. Mutations of the VHL gene are associated with Von Hippel—Lindau disease. The protein encoded by this gene is a component of the protein complex that includes elongin B, elongin C, and cullin-2, and possesses ubiquitin ligase E3 activity. This complex is involved in the ubiquitination and degradation of a hypoxia-inducible-factor (HIF), which is a transcription factor that plays a central role in the regulation of gene expression by oxygen.

While targeted therapies have been remarkably successful in treating cancer driven by the activation of a single oncogene, these drugs are much less effective in molecularly heterogeneous cancers driven by a multitude of dysregulated signaling networks. Successful treatment therefore likely requires a personalized medicine approach based on robust predictive biomarkers that can stratify patients toward appropriate targeted therapies. Here, a quantitative phosphoproteomic screen was used to identify Src as a potential pharmacologic target in VHL+metastatic RCC.

II. Description of Several Embodiments

A. Methods of Diagnosis

Disclosed herein are methods of predicting if a subject with cancer, such as RCC, and in particular RCC expressing Von Hippel Lindau protein (VHL$^+$ RCC), would benefit from treatment with an inhibitor of Src. As disclosed herein, the molecular signature for RCC tumor sensitive to treatment with a Src inhibitor is the overexpression of VHL, Src, PTP1B, and/or phosphorylated FAK and/or the underexpression of HIF-1α, HIF-2α, and/or CA-IX relative to a threshold level of expression predetermined for each biomarker for the particular method of assessing the expression of the biomarker.

Thus, in particular examples, the methods include detecting expression of the cancer biomarkers VHL, Src, and CA-IX in a sample obtained from a subject, such as a tumor sample, and comparing the expression to a threshold level of expression.

As disclosed herein, overexpression of PTP1B relative to a threshold level of expression also correlates with Src inhibitor sensitivity in VHL$^+$ RCC. Therefore, PTP1B expression can be used to determine or augment a determination of Src inhibitor sensitivity. Thus, in some examples, the expression of PTP1B is detected and compared to a threshold level of expression. Overexpression of PTP1B relative to the threshold indicates Src inhibitor sensitive cancer.

As disclosed herein, underexpression of HIF such as HIF-1α and/or HIF-2α relative to a threshold level of expression signifies Src inhibitor sensitivity in VHL$^+$ RCC. Therefore, HIF expression can be used to determine or augment a determination of Src inhibitor sensitivity. Thus, in some examples, the expression of HIF is detected and compared to a threshold level of expression. Underexpression of HIF relative to a threshold level of expression indicates Src inhibitor sensitive cancer.

As disclosed herein, underexpression of CA-IX relative to a threshold level of expression signifies Src inhibitor sensitivity in VHL+ RCC. Therefore, CA-IX expression can be used to determine or augment a determination of Src inhibitor sensitivity. Thus, in some examples, the expression of CA-IX is detected and compared to a control. Underexpression of CA-IX relative to the threshold indicates a cancer that is sensitive to a Src inhibitor.

In some examples, expression level of at least VHL and Src is determined. In some embodiments, the expression level of at least VHL, Src and one of PTP1B, HIF or CA-IX is determined. In some embodiments, the expression level of at least VHL, Src, PTP1B, HIF and CA-IX are determined. In some embodiments the expression level of VHL, Src and a combination of PTP1B, HIF and CA-IX are determined. In still further examples, the expression level of at least VHL, Src, and CA-IX are determined.

In some examples, the phosphorylation activity of Src is determined by detecting the phosphorylation of a downstream target of Src and comparing it to a threshold level of activity. Phosphroylation of the Src substrate that exceeds the threshold level of activity indicates that the tumor will be sensitive to Src. In some examples, FAK is the substrate of Src and the amount or phospho-FAK (pFAK) is compared to a threshold level of activity, such as a control with a predetermined level of phosphorylation activity characteristic of Src-resistant tumors. In this example, an amount of pFAK in the sample that exceeds amount of pFAK in the control indicates that the sample is sensitive to Src inhibitors.

A level of expression of the cancer biomarkers above as well as housekeeping genes can be assessed using any suitable method known in the art. For example, detection of gene expression can be accomplished by detecting nucleic acid molecules (such as RNA) using nucleic acid amplification methods (such as RT-PCR) or array analysis. Detection of gene expression can also be accomplished using immunoassays that detect proteins (such as ELISA, Western blot, or immunohistochemistry assay). Additional methods of detecting gene expression are well known in the art and are described in greater detail below.

In some embodiments, the expression of the disclosed biomarker is detected in a sample of a tumor obtained from a subject. Tumor samples may include cancer cells. Tumor samples may also include normal tissue adjacent to the tumor. This normal tissue may serve as an internal negative control, especially in the case of assays that detect expression of a biomarker in the context of tissue structure, including immunohistochemistry, in situ hybridization, or microdissection followed by nucleic acid amplification. It will appreciated that any method of obtaining tissue from a subject can be utilized, and that the selection of the method used will depend upon various factors such as the type of tissue, age of the subject, or procedures available to the practitioner. For example, the tissue sample can be obtained by a variety of procedures including, but not limited to, surgical excision, aspiration, or biopsy.

A threshold level of expression is a quantified level of expression of a particular gene or set of genes. An expression level of a gene or set of genes (alone or in combination) in a sample that exceeds or falls below the threshold level of expression is predictive of a particular disease state or outcome. In but one example (simplified for ease of explanation) expression of Src and VHL exceeding a threshold level of expression is predictive that the tumor will be sensitive to a Src inhibitor.

The nature and numerical value (if any) of the threshold level of expression will vary based on the method chosen to determine the expression the gene or gene set used in the prediction. In light of this disclosure, any person of skill in the art would be capable of determining the threshold level of expression in a patient sample that would be predictive of sensitivity to a Src inhibitor using any method of measuring specific RNA or protein expression now known in the art or yet to be disclosed.

The concept of a threshold level of expression should not be limited to a single value or result. Rather, the concept of a threshold level of expression encompasses multiple threshold expression levels that could signify, for example, a high, medium, or low probability of, for example, sensitivity to Src inhibitors. Alternatively, there could be a low threshold of expression wherein expression of Src and VHL in the sample below the threshold indicates that the tumor is likely to be resistant to a Src inhibitor and a separate high threshold of expression wherein Src and VHL expression in the sample above the threshold indicates that the tumor is likely to be sensitive to a Src inhibitor. Src and/or VHL expression in the sample that falls between the two threshold values may be inconclusive as to whether the tumor is or is not sensitive to a Src inhibitor.

To obtain a threshold value of biomarker expression that indicates that a tumor is sensitive to a Src inhibitor for a particular method of measuring biomarker expression, (for example RTPCR, ELISA, ISH, or IHC) one would determine biomarker expression in a set of tumors and sorting those tumors on the basis of their sensitivity to Src using the particular method.

One method of obtaining a threshold level of expression is to select a number of tumor samples at random and measure the expression of the particular biomarker in all of those tumor samples. The threshold level of expression may be the $1^{st}$, $5^{th}$, $10^{th}$, $20^{th}$, or $50^{th}$ percentile of the distribution of expression of the marker in all the tumors. In some examples, 50 tumors are selected. In others, 100, 200, 500, 1000 or more tumor samples are selected.

In some examples, the threshold level of expression will be the level of expression that provides the maximal ability to predict whether or not the tumor will be sensitive to Src. and will maximize both the selectivity and sensitivity of the test. The predictive power a threshold level of expression may be evaluated by any of a number of statistical methods known in the art. One of skill in the art will understand which statistical method to select on the basis of the method of determining biomarker expression and the data obtained.

Receiver Operating Characteristic curves, or "ROC" curves, may be calculated by plotting the value of a variable versus its relative frequency in each of two populations. Using the distribution, a threshold is selected. The area under the ROC curve is a measure of the probability that the expression correctly indicates the diagnosis. If the distribution of biomarker expression between the two cohorts overlaps, then biomarker expression values from subjects falling into the area of overlap then the subject providing the sample cannot be diagnosed. See, e.g., Hanley et al, *Radiology* 143, 29-36 (1982). In that case, a low threshold of expression and a high threshold of expression may be selected.

An odds ratio measures effect size and describes the amount of association or non-independence between two groups. An odds ratio is the ratio of the odds that biomarker expression above the threshold will occur in tumors known to be sensitive to Src inhibitors over the odds that biomarker expression above the threshold will occur in tumors known to be resistant to Src. An odds ratio of 1 indicates that biomarker expression above the threshold is equally likely in both cohorts. An odds ratio greater or less than 1 indicates that expression of the marker is more likely to occur in one cohort or the other.

A hazard ratio may be calculated by estimate of relative risk. Relative risk is the chance that a particular event will take place. For example: a relative risk may be calculated from the ratio of the probability that a tumor with an expression of the biomarker that exceeds the threshold level of expression is sensitive to a Src inhibitor over the probability that a tumor with an expression of the biomarker below the threshold level of expression is resistant to a Src inhibitor. In the case of a hazard ratio, a value of 1 indicates that the relative risk is equal in both the first and second groups and that the assay has little or no predictive value; a value greater or less than 1 indicates that the risk is greater in one group or another, depending on the inputs into the calculation.

Multiple threshold levels of expression may be selected by so-called "tertile," "quartile," or "quintile" analyses. In these methods, multiple groups can be considered together as a single population, and are divided into 3 or more bins having equal numbers of individuals. The boundary between two of these "bins" may be considered threshold levels of expression indicating a particular level of risk that the subject has or will have a poor prognosis. A risk may be assigned based on which "bin" a test subject falls into.

The threshold level of expression may also differ based on the purpose of the test. For a test to determine whether or not a tumor is or is not sensitive to a Src inhibitor, two types of tumors may be tested: one cohort of tumors known to be sensitive to Src inhibitors and another known not to be sensitive to Src inhibitors. Biomarker expression is determined by the same method in both cohorts, and the threshold level of expression to differentiate the cohorts is determined by one or more of the methods described above.

One type of threshold level of expression is the amount or valuation of expression relative to one or more controls or standards. Expression may be above or below a control that is known to be equivalent to the threshold level of expression. Alternatively, the threshold level of expression may be given in the—fold amount of expression relative to a negative control. If biomarker expression that exceeds the threshold level of expression signifies sensitivity to a Src inhibitor, the threshold level of expression may be set at 1.1×, 1.5×, 2×, 3×, 5×, 10×, 20×, 50× or more than the level of expression in a normal control. Alternatively, if expression of the biomarker below a threshold level of expression signifies sensitivity to a Src inhibitor, the threshold level of expression may be set at 0.9×, 0.75×, 0.5×, 0.1×, 0.01×, 0.001× or less than the expression of a normal control. The control may be any suitable control against which to compare expression of a gene in a sample. In some examples, the control sample is non-tumor tissue. In some examples, the non-tumor tissue is obtained from the same subject, such as non-tumor tissue that is adjacent to the tumor. In other examples, the non-tumor tissue is obtained from a healthy control subject. In other examples, a set of controls that are equivalent to known expression levels are evaluated to formulate a standard curve. Expression in the sample is then quantified on the basis of that standard curve and then compared to the threshold level of expression.

B. Detecting Expression of Cancer Biomarkers

As described below, expression of the disclosed RCC biomarkers can be detected using any one of a number of methods well known in the art. For example, it is contemplated herein that RCC biomarkers can be detected by measuring expression of mRNA, cDNA, protein or a combination thereof.

i. Methods for Detection of mRNA or cDNA

Gene expression can be evaluated by detecting mRNA encoding the gene of interest. Thus, the disclosed methods can include evaluating mRNA encoding VHL and Src. In some embodiments, the mRNA of additional markers, such as mRNA encoding PTP1B, HIF and/or CA-IX is detected. In some examples, the mRNA is quantified. RNA can be isolated from a sample of a tumor (for example, RCC) from a subject, a sample of adjacent non-tumor tissue from the subject, a sample of tumor-free tissue from a normal (healthy) subject, a blood sample, or combinations thereof, using methods well known to one skilled in the art, including commercially available kits. General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Biotechniques 6:56-60 (1988), and De Andres et al., Biotechniques 18:5 42-44 (1995). In one example, RNA isolation can be performed using purification kit, buffer set and protease from commercial manufacturers, such as QIAGEN® (Valencia, Calif.), according to the manufacturer's instructions. For example, total RNA from cells (such as those obtained from a subject) can be isolated using QIAGEN® RNeasy mini columns. Other commercially available RNA isolation kits include MASTERPURE® Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from tumor or other biological sample can be isolated, for example, by cesium chloride density gradient centrifugation.

Methods of gene expression profiling include methods based on hybridization analysis of polynucleotides, methods based on sequencing of polynucleotides, and proteomics-based methods. In some examples, mRNA expression in a sample is quantified using Northern blotting or in situ hybridization (Parker & Barnes, Methods in Molecular Biology 106:247-283, 1999); RNAse protection assays (Hod, *Biotechniques* 13, 852-854, (1992)); and PCR-based methods, such as reverse transcription polymerase chain reaction (RT-PCR) (Weis et al, *Trends in Genetics* 8, 263-264, (1992)). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, in normal and tumor tissues, with or without drug treatment, to characterize patterns of gene expression, to discriminate between closely related mRNAs, and to analyze RNA structure.

Methods for quantifying mRNA are well known in the art. In some examples, the method utilizes nucleic amplification such as RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp® RNA PCR kit (Perkin Elmer, Calif.), following the manufacturer's instructions. The derived cDNA can then be used as a template in the subsequent PCR reaction.

In some examples, gene expression is identified or confirmed using the microarray technique. Thus, the expression profile can be measured in either fresh or paraffin-embedded tumor tissue, using microarray technology. In this method, RCC biomarker nucleic acid sequences of interest (including cDNAs and oligonucleotides) are plated, or arrayed, on a microchip substrate. The arrayed sequences are then hybridized with isolated nucleic acids (such as cDNA or mRNA) from cells or tissues of interest. Just as in the RT-PCR method, the source of mRNA typically is total RNA isolated from human tumors, and optionally from corresponding noncancerous tissue and normal tissues or cell lines.

In particular embodiments provided herein, arrays can be used to evaluate RCC biomarker expression, for example to diagnose a patient with cancer (for example, RCC). When describing an array that consists essentially of probes or primers specific for the genes listed in Table 1, such an array includes probes or primers specific for these RCC biomarkers, and can further include control probes (for example to confirm the incubation conditions are sufficient). In some examples, the array may consist essentially of probes or primers specific for VHL, Src, PTP1B, HIF 5 and/or CA-IX, and can further include control probes. In other examples, the array may include fewer, such as 1, 2, 3, or 4 fewer RCC biomarkers. Exemplary control probes include GAPDH, β-actin, and 18S RNA. In one example, an array is a multi-well plate (e.g., 98 or 364 well plate).

In one example, the array includes, consists essentially of, or consists of probes or primers (such as an oligonucleotide or antibody) that can recognize VHL, Src, PTP1B, HIF and/or CA-IX. The oligonucleotide probes or primers can further include one or more detectable labels, to permit detection of hybridization signals between the probe and target sequence (such as one of the RCC biomarkers disclosed herein).

In situ hybridization (ISH) is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of RCC biomarkers.

Sample cells or tissues are treated to increase their permeability to allow a probe, such as an RCC biomarker-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a non-cancerous kidney sample. Since the sequences of the RCC biomarkers of interest are known, probes can be designed accordingly such that the probes specifically bind the gene of interest.

In situ PCR is the PCR-based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

In some embodiments of the detection methods, the expression of one or more "housekeeping" genes or "internal controls" can also be evaluated. These terms include any constitutively or globally expressed gene (or protein, as discussed below) whose presence enables an assessment of RCC biomarker gene (or protein) levels. Such an assessment includes a determination of the overall constitutive level of gene transcription and a control for variations in RNA (or protein) recovery.

ii. Detecting Cancer Biomarker Proteins

In some examples, expression levels of VHL, Src, PTP1B, HIF and/or CA-IX is analyzed. Suitable biological samples include samples containing protein obtained from a tumor (such as RCC sample) of a subject, from non-tumor tissue of the subject, from a blood sample from the subject, and/or protein obtained from one or more samples of cancer-free tissue samples or subjects.

Antibodies specific for the disclosed proteins (for example, VHL, Src, PTP1B, HIF and/or CA-IX) can be used for detection and quantification of RCC biomarker proteins by one of a number of immunoassay methods that are well known in the art, such as those presented in Harlow and Lane (Antibodies, A Laboratory Manual, CSHL, New York, 1988). Methods of constructing such antibodies are known in the art. In addition, such antibodies may be commercially available. Any standard immunoassay format (such as ELISA, Western blot, or RIA assay) can be used to measure protein levels. Thus, in one example, polypeptide levels of two or more of VHL, Src, PTP1B, HIF and/or CA-IX in a tumor (for example, RCC) can readily be evaluated using these methods. Immunohistochemical techniques can also be utilized for RCC biomarker detection and quantification. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantifying RCC biomarker proteins, a biological sample of the subject that includes cellular proteins can be used. Quantification of proteins (for example, VHL, Src, PTP1B, HIF and/or CA-IX) can be achieved by immunoassay. The amount of RCC biomarker proteins can be assessed in the tumor and optionally in the adjacent non-tumor tissue or in tissue from cancer-free subjects. The amounts of RCC biomarker protein in the tumor can be compared to levels of the protein found in cells from a cancer-free subject, tissue or other control (such as a standard value or reference value). A significant increase or decrease in the amount can be evaluated using statistical methods known in the art.

Quantitative spectroscopic methods, such as SELDI, can be used to analyze RCC biomarker protein expression in a sample (such as tumor tissue, non-cancerous tissue, and tissue from a cancer-free subject). In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). Such methods are well known in the art (for example see U.S. Pat. Nos. 5,719,060; 6,897,072; and 6,881,586). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as RCC biomarker proteins. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent methods of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as RCC biomarker proteins) can be desorbed and analyzed by any of several methods, for example using mass spectrometry. When the analyte is ionized in the process of desorption, such as in laser desorption/ionization mass spectrometry, the detector can be an ion detector. Mass spectrometers can determine the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection methods can be implemented in series to fully interrogate the analyte components and function associated with retained molecules at each location in the array.

In a particular example, the chromatographic surface includes antibodies that specifically bind VHL, Src, PTP1B, HIF and/or CA-IX. In other examples, the chromatographic surface consists essentially of, or consists of, antibodies that specifically VHL, Src, PTP1B, HIF and/or CA-IX. In some examples, the chromatographic surface includes antibodies that bind other molecules, such as housekeeping proteins like β-actin or myosin.

In another example, antibodies are immobilized onto the surface using a bacterial Fc binding support. The chromatographic surface is incubated with a sample, such as a sample of a tumor. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

C. Methods of Treatment

Methods of treating a subject with a RCC that is sensitive to treatment with a Src inhibitor are provided herein. The methods include selecting an individual that has a VHL and Src positive RCC (for example using the methods described above in Section A). Typical subjects intended for treatment with Src inhibitor include humans, as well as nonhuman primates and other animals, such as mice.

After selection, the subject is administered a therapeutically effective amount of one or more Src inhibitors, thereby treating the cellular proliferative disorder. In some examples, the Src inhibitor is provided as a pharmaceutical composition or compositions. Exemplary Src inhibitors are siRNAs, ribozymes, antisense molecules, and small molecule inhibitors, such as saracatinib (AZD0530), Dasatinib (BMS-354825), AP23846, UCS15A, bosutinib (SKI-606), and KX2-391 (KXO1). In some embodiments, a subject is administered one or more small-molecule inhibitors of Src, such as one or more of saracatinib (AZD0530), Dasatinib (BMS-354825), AP23846, UCS15A, bosutinib (SKI-606), and KX2-391 (KXO1).

The administration of the Src inhibitors can be for either a prophylactic or a therapeutic purpose. When provided prophylactically, Src inhibitors are provided in advance of any symptom. The prophylactic administration of the compounds serves to prevent or ameliorate any subsequent disease process. When provided therapeutically, the compounds are provided at (or shortly after) the onset of a symptom of disease.

For prophylactic and therapeutic purposes, Src inhibitors can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition.

Determination of effective dosages is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of Src inhibitors (for example, amounts that are effective to alleviate one or more symptoms of a targeted disease or condition). In alternative embodiments, an effective amount or effective dose of the Src inhibitors may simply inhibit or enhance one or more selected biological activities correlated with a disease or condition.

The actual dosage of Src inhibitors will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the Src inhibitors for eliciting the desired activity or biological response in the subject. Dosage regimens can be adjusted to provide an optimum prophylactic or therapeutic response.

A therapeutically effective amount is also one in which any toxic or detrimental side effects of the compound and/or other biologically active agent is outweighed in clinical terms by therapeutically beneficial effects. A non-limiting range for a therapeutically effective amount of a Src inhibitor within the methods and formulations of the disclosure is about 0.0001 µg/kg body weight to about 10 mg/kg body weight per dose, such as about 0.0001 µg/kg body weight to about 0.001 µg/kg body weight per dose, about 0.001 µg/kg body weight to about 0.01 µg/kg body weight per dose, about 0.01 µg/kg body weight to about 0.1 µg/kg body weight per dose, about 0.1 µg/kg body weight to about 10 µg/kg body weight per dose, about 1 µg/kg body weight to about 100 µg/kg body weight per dose, about 100 µg/kg body weight to about 5 500 µg/kg body weight per dose, about 500 µg/kg body weight per dose to about 1000 µg/kg body weight per dose, or about 1.0 mg/kg body weight to abuut 10 mg/kg body weight per dose.

Dosage can be varied by the attending clinician to maintain a desired concentration at a target site. Higher or lower concentrations can be selected based on the mode of delivery, for example, trans-epidermal, rectal, oral, pulmonary, intranasal delivery, intravenous or subcutaneous delivery. To achieve the same serum concentration level, for example, slow-release particles with a release rate of 5 nanomolar (under standard conditions) would be administered at about twice the dosage of particles with a release rate of 10 nanomolar.

The specific dose level and frequency of dosage for any particular subject may be varied and will depend upon a variety of factors, including the activity of the specific compound, the extent of existing disease activity, the age, body weight, general health, sex, diet, mode and time of administration, rate of excretion, drug combination, and severity of the condition of the host undergoing therapy.

D. Kits

A diagnostic kit may contain reagents such as oligonucleotides configured to perform nucleic acid amplification (including TaqMan® amplification) that specifically quantifies the expression of INHBA. A diagnostic kit may also comprise an array that includes oligonucleotides configured to quantify INHBA expression.

A diagnostic kit may contain reagents, such as antibodies, that specifically bind proteins. Such kits will contain one or more specific antibodies, buffers, and other reagents configured to detect binding of the antibody to the specific epitope. One or more of the antibodies may be labeled with a fluorescent, enzymatic, magnetic, metallic, chemical, or other label that signifies and/or locates the presence of specifically bound antibody. The kit may also contain one or more secondary antibodies that specifically recognize epitopes on other antibodies. These secondary antibodies may also be labeled. The concept of a secondary antibody also encompasses non-antibody ligands that specifically bind an epitope or label of another antibody. For example, streptavidin or avidin may bind to biotin conjugated to another antibody. Such a kit may also contain enzymatic substrates that change color or some other property in the presence of an enzyme that is conjugated to one or more antibodies included in the kit.

A diagnostic kit may also contain an indication of a threshold level of expression of one or more biomarkers that will signify that the subject will benefit from treatment with a Src inhibitor. An indication may be any communication of a threshold level of expression. The indication may further indicate that expression of the biomarker above the threshold level of expression will signify that the subject will benefit from treatment with a src inhibitor or it may indicate that expression of the biomarker below the threshold level of expression will signify that the subject will benefit from treatment with a src inhibitor.

The indication of the threshold level may be provided in multiple stages such in a system that the subject has a high, medium or low likelihood of benefitting from treatment with a src inhibitor. The indication may comprise any number of stages. The indication may indicate the threshold of expression numerically, as in an optical density of an ELISA assay, a protein concentration (such as ng/ml), a percentage of cells expressing the biomarker in a tissue, a numerical intensity of staining determined using image analysis software, or in fold-expression relative to a positive control, negative control, or housekeeping gene. The indication may itself be a positive or negative control that is intended to provide an equivalent level of expression to the threshold level of expression.

The indication may be communicated through any tangible medium of expression. It may be printed the packaging material, a separate piece of paper, or any other substrate and provided with the kit, provided separately from the kit, posted on the Internet, written into a software package. The indication may comprise an image such as a FACS image, a photograph or a photomicrograph, or any copy or other reproduction of these, particularly when biomarker expression is determined through the use of in situ hybridization, FACS analysis, or immunohistochemistry, The diagnostic procedures can be performed "in situ" directly upon blood smears or tissue sections (fixed and/or frozen), tissue biopsies, or other samples. DNA or RNA from such a sample can be isolated using procedures which are well known to those in the art.

EXAMPLES

The following examples are illustrative of disclosed methods. In light of this disclosure, those of skill in the art will recognize that variations of these examples and other examples of the disclosed method would be possible without undue experimentation. The examples disclose, among other things, that immunohistochemistry of 346 human RCC tumors identified a positive correlation between Src and VHL expression while treatment of VHL+ xenografts with dasatinib blocked tumor growth in vivo. Conversely, forced expression of HIF, which phenocopied VHL loss, diminished Src's signaling output by downregulation of PTP1B, thereby conferring resistance to dasatinib.

Example 1

Materials and Methods

This section describes the materials and methods used in Example 2, Example 3, Example 4, and Example 5 below.

Cell Culture: RCC isogenic pairs of VHL WT ACHN and SN12C and counterparts expressing shRNA targeting VHL have already been described (Thomas G V et al, Nat Med 12, 122 (2006), incorporated by reference herein.) ACHN and SN12C cells expressing a VHL-resistant version of HIF-1α or HIF-2α were generated by transducing a retrovirus expressing HIF-1α (P564A) and HIF-2α (P405A; P853A) in which the proline hydroxylation sites are mutated to alanine. Transduction of empty retroviral vector (pBabe) served as a negative control.

To assess the role of Src the following constructs were used: SN12C (i) shRNA mediated knock down of Src using pSuper-Retro-puro system; (ii) c-Src rescued lines resistant to the shRNA targeting using a retroviral expression vector pBabe-hygro encoding the chicken c-Src protein and (iii) a dasatinib resistant line with a mutant form of c-Src (T338I). Procedures were followed as described in Zhang et al, Cancer Cell 16, 67 (2009), which is incorporated by reference herein. In addition, SN12C cells expressing a lower level of PTP1B was developed by viral transduction with PTP1B shRNA (V2SHS_170902; Open Biosystems and TRC 0000002777; Sigma). An SN12C cell line stably transduced with GFP shRNA (Addgene) or with Non-Targeting shRNA Control (Sigma) served as a controls, respectively. SN12C cells overexpressing CSK were generated by stable transfection of pCSK-N1.

All cell lines were routinely grown in monolayer cultures in Dulbecco's Modified Eagle Medium (DMEM) supplemented with 10% FBS and penicillin/streptomycin.

Antibodies: The antibodies used in western blotting and immunohistochemistry staining were as follows: antibodies that bind pY419 Src, pY530 Src, Src, pY576/577 FAK, FAK, pY705 STAT3, CSK (C74C1), ERK1/2, and cleaved caspase-3 (Asp175) were obtained from New England Biolabs; antibodies that bind α-tubulin (TUO2), β-actin, (C4), pY204, and ERK1/2 (E-4) were obtained from Santa Cruz Biotechnology; antibodies that bind Src, VHL, HIF-1α, and PTP1B were obtained from BD Biosciences, antibodies that bind HIF-2α, PTP1B (EP1841Y), and STAT3 (STAAD22A) were obtained from Abcam, an antibody that binds HIF2-a was obtained from Millipore, an antibody that binds CA-IX was obtained from Novus Biologicals; an antibody that binds Ki-67 was obtained from DAKO; and Pimonidazole was obtained from Hypoxyprobe, Inc.

The technical data sheet for VHL monoclonal antibody, BD Pharmingen 556347, clone Ig32 is available at http://www.bdbiosciences.com/external_files/pm/doc/tds/cell_bio/live/we b_enabled/65031A_556347.pdf (last accessed on 23 May 2012) and is incorporated by reference herein.

The technical data sheet for the Src monoclonal antibody, BD Transduction Laboratories 612378, clone 8/SRC-1 is available at http://www.bdbiosciences.com/external_files/pm/doc/tds/tl/live/web_enabled/S26620_612378.pdf (last accessed on 23 May 2012) and is incorporated by reference herein.

The technical data sheet for the HIF-1α monoclonal antibody BD Transduction Laboratories 610959, clone 54/HIF-1α is available at http://www.bdbiosciences.com/external_files/pm/doc/tds/tl/live/web_enabled/H7232 0_610959.pdf (last accessed on 23 May 2012) and is incorporated by reference herein.

The technical data sheet for the PTP1B monoclonal antibody BD Transduction Laboratories 610140, clone 15/PTP1B is available at http://www.bdbiosciences.com/external_files/pm/doc/tds/tl/live/web_enabled/P1802 0_610140.pdf (last accessed on 23 May 12) and is incorporated by reference herein.

The technical data sheet for the CA-IX monoclonal antibody clone 2D3 is available at http://www.novusbio.com/PDFs/NBP1-51691.pdf (last accessed on 23 May 2012) and is incorporated by reference herein.

The technical data sheet for the CA-IX monoclonal antibody 1G7 is available at http://www.novusbio.com/PDFs/NBP1-47688.pdf (last accessed on 23 May 2012) and is incorporated by reference herein.

Cell Proliferation Assay: $5 \times 10^4$ cells were plated and treated with a single dose of 25, 50 or 100 nM dasatinib or vehicle (DMSO). Cells were trypsinized, resuspended in DMEM/10% FBS and counted using the VI-Cell XR automated cell-viability analyzer (Beckmann Coulter) at 96 hours post-treatment, unless otherwise stated. Cell counts were performed in triplicate and experiments were repeated on at least three independent occasions. Cells were split to sustain log phase growth.

Xenografts: $5 \times 10^6$ SN12C and SN12C shVHL cells or $1 \times 10^6$ SN12C and SN12C v-Src cells diluted in 100 µl of matrigel (Collaborative Biomedical) were subcutaneously injected into both flanks of nude or SCID mice, respectively. When tumor volume reached 150 mm$^3$, mice were randomized to daily treatment with vehicle or 10 mg/kg of dasatinib (six animals/group). Nude mice were injected with pimonidazole (Hypoxyprobe, Inc) 1 h prior to sacrifice.

Flow Cytometry: Cells were plated at a density such that they were no more than 70% confluent on the day of analysis. Cells were treated with dasatinib for 48 hours unless otherwise stated. For propidium iodide staining, cells were trypsinized, collected by centrifugation and washed in PBS prior to fixing in 70% v/v ethanol. Ethanol was removed by washing in PBS. Cells were incubated with 100 µg/ml RNase A (Sigma) for 5 minutes and stained with 50 µg/ml PI for 30 minutes. For BrdU analysis, dasatinib -treated cells were incubated for 30 min with 10 µM BrdU (Sigma) prior to harvesting. Cells were stained with fluorescein isothiocyanate (FITC)-conjugated anti-BrdU antibodies (BD Biosciences) according to the manufacturer's instructions. Following multiple washes in blocking solution and PBS, cells were stained with 5 µg/ml PI for 30 minutes. The PI or BrdU/PI-stained samples were analyzed by an LSR® FACS (Becton Dickinson) and the cell cycle profile was analyzed with the FlowJo® software (Tree Star Inc.). Phosphoprotein flow cytometry analysis was performed as previously described in Shah N P et al, Cell 14, 485 (2008), incorporated by reference herein.

Real-Time PCR: Total RNA was extracted from cells with the RNeasy kit (Qiagen) and the reverse transcription performed with 1 µg of RNAs and 200 units of Superscript II® enzyme (Invitrogen). Real time PCR amplifications were performed using the Brilliant II Fast® SYBR Green QPCR Master Mix (Agilent Technologies) with 2 µl of 1/10 cDNA and 300-500 nM of primers.

Reactions proceeded with initial 2 minutes incubation at 95° C. followed by 40 cycles of amplification: 95° C. for 5 seconds and 60° C. for 20 seconds in a Mx3000p® thermal cycler (Agilent Technologies). Fluorescence was measured in real time with the dissociation curves option; the cycle threshold (Ct) values were calculated using the Mx3000p® algorithm (Agilent Technologies). Standard curves were performed on serial dilutions of genomic human DNA or RT-transcripts. Comparative quantitation was performed using the MxPro® QPCR software by comparing the Ct value obtained from the amplification of a given target with that determined for the housekeeping gene RPLP0 (human acidic ribosomal phosphoprotein P0). Relative mRNA abundance was calculated using the $\Delta\Delta$Ct method.

Chromatin Immunoprecipitation: Sheared, formaldehyde crosslinked chromatin derived from $0.5 \times 10^6$ cells was incubated with 1 µl of anti-HIF-1α antibody (Abcam ab2185) or 2 µg of normal rabbit (IgG) antibody (Millipore) to immunoprecipitate DNA overnight at 4° C. A $\frac{1}{100}$ fraction of the chromatin was removed prior to immunoprecipitation as input. Immune complexes were collected with protein A/G (3:1)-magnetic beads (Invitrogen). After extensive washing, immune complexes were released, crosslinks were reversed, and DNA was purified with a mini-elute PCR purification kit (Qiagen) and eluted with 60 ul E buffer.

A putative palindromic HRE sequence, localized at −214 to −224, was found in the PTP1B promoter region using CLCbio Genomics Workbench® software. Primers to amplify the sequence were generated and real-time PCR was performed in triplicate on 2 µl of the immunoprecipitated DNA or 20 of the 1% input. Immunoprecipitated DNA was calculated as "% of input" using the ΔΔCt method.

Western Blot Analysis:

Cells were seeded to have approximately 50% confluence upon lysis. Cells were lysed after 18 hours of exposure to vehicle or dasatinib in EBC lysis buffer (50 mM Tris, pH 8.0, 120 mM NaCl, 0.5% Nonidet P-40) supplemented with complete protease (Roche) and phosphatase inhibitor (Calbiochem) cocktails. Xenograft tumors were lysed in a protein lysis buffer (150 mM NaCl, 1 mM EDTA, 50 mM Tris, 1% v/v Triton X-100, 1 nM NaF, 1 mM NaVO$_3$, 5 µM bpVphen, 1 mM PMSF), supplemented with phosphatase inhibitors I & II, protease inhibitor cocktail and TLCK (Sigma). Protein extracts (40-100 µg) were resolved by SDS-PAGE, transferred on to polyvinylidene fluoride membrane (Millipore) and probed with appropriate antibodies. The primary antibodies were detected using horseradish peroxidase-linked goat anti-mouse or anti-rabbit secondary antibodies (Jackson Laboratories) and visualized by SuperSignal West Pico Chemiluminescent substrate (Thermo Scientific). Images were collected by UVP BioSpectrum AC Chemi HR 410® Imaging System. Blots were analyzed and quantified using UVP VisionWorksLS® Image Acquisition and Analysis software.

In Vitro Src Kinase Assay: Equal number of subconfluent SN12C and SN12C-shVHL cells were harvested is NETN lysis buffer [20 mM Tris (pH 8.0), 150 mM NaCl, 0.5% NP-40, 1 mM EDTA] supplemented with protease inhibitors (0.5 mM phenylmethylsulfonyl fluoride and 0.1 µM each of aprotinin, E-64, and leupeptin), and phosphatase inhibitors (1 mM sodium orthovanadate and 20 mM sodium fluoride). Endogenous Src was immunoprecipitated with anti-Src 327 ascites and captured with Protein G-sepharose 4B (Invitrogen). Immunoprecipitated Src kinase activity from SN12C and SN12C-shVHL cells was measured using a Src Assay Kit from (Millipore #17-131) according to the manufacturer's instructions.

Src immunoprecipitates or control immunoprecipitates (lysates incubated with Protein G in the absence of antibody) were incubated in Src Kinase Reaction Buffer [100 mM Tris (pH 7.2), 125 mM MgCl$_2$, 5 mM MnCl$_2$, 2 mM EGTA, 250 µM sodium orthovanadate, 2 mM dithiothreitol] at 30° C. for 10 minutes with Src substrate peptide, 10 µCi [g-32P] ATP in manganese/ATP buffer [75 mM MnCl$_2$, 500 µM ATP in 75 mM MOPS (pH 7.2), 25 mM b-glycerol phosphate, 5 mM EGTA, 1 mM sodium orthovanadate, 1 mM dithiothreitol] and 50 nM Dasatinib where indicated. Reactions were spotted onto P81 phosphocellulose paper, precipitated with 40% TCA, then washed five times with 0.75% phosphoric acid, once with acetone and transferred to vials containing 5 ml of scintillation fluid (CytoScint®, Fisher #BP458-4) and $^{32}$P-labeled substrate peptide was measured in a Packard 1900TR® Liquid Scintillation Analyzer. Data are presented as the mean CPM±S.D. from three independent experiments assayed in duplicate. Statistical analysis between mean CPM of SN12C and SN12C-shVHL Src kinase activity was performed using a 2-tailed Student's t-test. For the immunoblot analysis, the amount of Src was quantified with NIH Image J and presented numerically as the fold difference between the two lines.

Sample Preparation, Peptide Immunoprecipitation and Mass Spectrometry Analysis: SN12C and SN12C-shVHL cells were maintained in DMEM supplemented with 10% FBS. Cells (40-50% confluence per 10 cm plate) were seeded for 24 hours, washed twice with PBS and then incubated for 24 hours in serum-free media. Cells were stimulated with 10% serum for 10 minutes and harvested in 900 µl/dish 8M Urea. Unstimulated cells were used as controls.

Cells were lysed in 8M urea, subjected to reduction, alkylation and trypsin digestion as previously as described in Huang et al, *Proc Natl Acad Sci USA* 104, 12867 (2007); incorporated by reference herein. Peptides were desalted on a C18 Sep-Pak Plus® cartridge (Waters), eluted with 25% acetonitrile and lyophilized to dryness. Lyophilized peptides were subjected to labeling with the iTRAQ 8-plex® reagent (Applied Biosystems).

Peptide immunoprecipitation was performed as described in Huang et al, supra. Briefly, 30 µg of protein G Plus-agarose beads (Sigma) were incubated with 12 µg of each of the antiphosphotyrosine antibodies (pTyr100 (Cell Signaling Technology), PT66 (Perkin Elmer) and 4G10 (Millipore) in 200 µl of immunoprecipitation buffer (100 mM Tris, 100 mM NaCl, 1% Nonidet P-40, pH 7.4) for 8 hours at 4° C. Beads were washed with rinse buffer (100 mM Tris, 100 mM NaCl, pH 7.4) and retained peptides were eluted from antibody with 70 µl of elution buffer (100 mM glycine, pH 2.5) for 1 hour at room temperature. Immobilized metal affinity chromatography was performed to enrich for phosphorylated peptides, and peptides retained on the column were eluted with 250 mM sodium phosphate (pH 8.0) and analyzed by electrospray ionization liquid chromatography tandem MS on a QqT of (QSTAR Elite®, Applied Biosystems) as described in Huang et al, supra.

Phosphopeptide Sequencing, Quantification and Analysis: MS/MS spectra were extracted, searched, and quantified by using Protein Pilot® (Applied Biosystems). Phosphorylation sites and peptide sequence assignments were validated by manual confirmation of raw MS/MS data. Peak areas of iTRAQ marker ions (m/z 113, 114, 115, 116, 117, 118, 119, and 121) were normalized with values from the iTRAQ® marker ion peak areas of nonphosphorylated peptides in supernatant of the immunoprecipitation. Each condition was normalized against the 113 channel to obtain fold changes across all eight conditions. Table 4 represents the mean and standard deviation of two biological replicate experiments.

Tissue Microarrays: Two separate RCC patient clinical databases were used to construct the TMAs described in the tests. The first TMA comprised of samples from 215 clear cell RCCs. All RCC samples were histologically reviewed. Tumor specific survival data were obtained by reviewing the hospital records and by the cancer registry. The second RCC TMA included 131 nephrectomies performed for kidney cancer. All tumors arrayed from this second dataset were histologically reviewed.

Immunohistochemistry: The first TMA was stained using the ultraView® Universal DAB Detection Kit (Ventana, Tucson, Ariz., USA). A clear cell RCC tumor with strong membranous Src positivity was used as positive control. Negative controls were identical array sections stained in the absence of the primary antibody. Immunohistochemistry can yield false positivity at the margin or edges of tissue (also known as the edge effect) and needs to be considered when scoring tissue microarray (TMA) cores. Therefore, to minimize false positivity, a conservative 5% cutoff, was use. Thus, any tumors with <5% cytoplasmic and/or membranous staining was considered negative and any tumors with >5% cytoplasmic and/or membranous staining was considered positive. Next, positive Src expression was analyzed subjectively based on antibody staining intensity as either having weak or strong cytoplasmic and/or membranous immunoreactivity, VHL immunostaining was similarly scored. The second TMA was processed using EnVision Kits® (DAKO), Super-Sensitive® IHC Detection Systems (BioGenex) or VECTASTAIN ABC® Kit (Vector Labs) according to the manufacturer's instructions (which are incorporated by reference herein.) Negative control slides were used in every run (incubated in DAKO Universal Negative Control Mouse/Rabbit). Diaminobenzidine tetrahydrochloride (DAB) was used as the enzyme substrate for visualization and counterstained with hematoxylin.

Image acquisition, management and automated analysis: The Aperio ScanScope CS® slide scanner (Aperio Technologies) was used to capture whole slide digital images with a 20× objective. Slides were de-arrayed to visualize individual cores, using the TMA Lab® (Aperio). A color deconvolution algorithm (Aperio) was used to develop a quantitative scoring model for measuring cytoplasmic immunoreactivity in TMAs consecutively stained with VHL, Src, CA-IX, PTP1B and pFAK. A nuclear algorithm was used to quantify HIF-2α and Ki-67 nuclear positivity. The algorithm was calibrated to individual staining patterns (range of hues and saturation) and three intensity ranges were generated. For pixels that satisfy the color specification, the algorithm counted the number and intensity-sum in each intensity range, along with three additional quantities: average intensity, ratio of strong/total number, and average intensity of weak positive pixels. The algorithm was calibrated for both cytoplasmic and nuclear expression by constructing receiver operator curves for Hue, Hue width, and color saturation.

A pseudo-color "mark-up" image was generated from the algorithm and verified to ensure that specified inputs were measuring the desired color and intensity ranges. All "mark up" images were inspected by a pathologist to confirm the accuracy of the algorithm. The final automated score was assessed for each core as the product of corrected average intensity and corrected positive pixel percentage. Src is expressed in RCC and correlates with VHL expression.

Statistical Analysis: Contingency table analysis and Chi-square test were used for the analysis of the association between membranous and cytoplasmic Src expression as well as between Src and VHL protein expression. Overall survival rates were determined according to the Kaplan-Meier method and analyzed for statistical differences using a log rank test. Spearman Rho correlation coefficients were used to assess the association between different biomarkers expression and was performed using the GraphPad Prism software. To analyze whether level of a protein can be predicted by other proteins, multiple linear regression was performed in the R statistical programming language (R v 2.10.1). All model variables, both response and explanatory, have been log transformed to improve normality. No model selection was performed. Two models were examined based on previous biological knowledge and the correlation results: Src level as the response variable with VHL and PTP1B as the explanatory variables, and PTP1B level as the response variable with VHL and HIF-2α as the explanatory variables. The statistical significance of differences for the in vitro experiments was determined by 2-tailed Student's t-test (GraphPad statistics software). Any difference with a P-value less than 0.05 was considered significant. The heatmap was generated using Spotfire software. Scatter plots were generated using Statistica software and thresholds gated as stated in figure legend.

Example 2

Src is Expressed in RCC and Correlates with VHL Expression

Figure 1B:
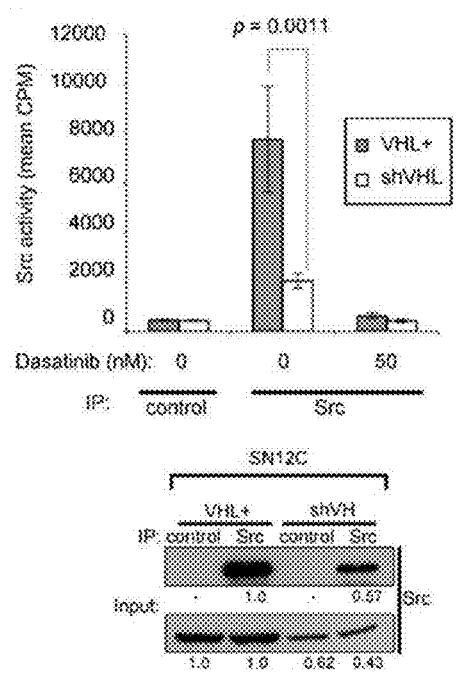

To identify cellular signaling networks differentially regulated in RCC subgroups, quantitative phosphoproteomics was performed on SN12C clear cell carcinoma cells, which retain VHL protein expression, and its isogenic subline, SN12CshVHL, which have reduced VHL by shRNA knockdown. Lysates from parallel cultures of serum-stimulated SN12C and SN12C-shVHL cells were labeled with iTRAQ 8-plex reagent and phosphotyrosine-containing peptides were subjected to immobilized metal affinity chromatography-tandem MS analysis. Quantitative phosphorylation profiles were generated for 22 phosphorylation sites while cluster analysis revealed a>50% reduction of pTyr at numerous phosphorylation sites in SN12C-shVHL lysates (See FIG. 1A and Table 1). Specifically, the proportion of pY419 autophosphorylated Src as well as several Src substrates, including annexin II, paxillin and inositol polyphosphate phosphatase-like 1 (INPPL1) were diminished in SN12C-shVHL lysates. The ability of serum to increase pTyr levels of Src substrates in SN12C cells but not SN12C-shVHL cells indicated VHL expression is a key determinant of Src kinase activity. Consistent with this observation, in vitro kinase assays showed SN12C cells contained approximately twice as much dasatinib-sensitive Src kinase activity as did SN12C-shVHL cells (FIG. 1B). Together, these data indicate VHL can regulate Src kinase activity as well as its downstream signaling.

TABLE 1

Summary of differentially phosphorylated proteins between SN12C an dSN12C shVHL cells

| Accession # | Protein Name | Protein Symbol | pY site |
|---|---|---|---|
| P06733 | Alpha-enolase | ENO1 | Y44 |
| Q96RT1 | ErbB2 interacting protein | Erbin | Y1104 |
| Q86Z02 | Homeodomain-interacting protein kinase 1 | HIPK1 | Y352 |
| Q14654 | Insulin receptor substrate 4 | IRS-4 | Y921 |
| Q86YV5 | Tyrosine-protein kinase SgK223 | SGK223 | Y413 |
| P49840 | Glycogen synthase kinase-3 alpha | GSK3A | Y279 |
| Q16539 | Mitogen-activated protein kinase 14 | p38-alpha | Y182 |
| P27361 | Mitogen-activated protein kinase 3 | ERK1 | Y204 |
| P06493 | Cyclin-dependent kinase 1 | CDK1 | Y15 |
| Q06124 | Protein tyrosine phosphatase, non-receptor type 11 | SHP-2 | Y63 |
| Q13627 | Dual specificity tyrosine-phosphorylation-regulated kinase 1A | DYRK1A | Y321 |
| Q13523 | Serine/threonine-protein kinase PRP4 homolog | PRP4 | Y849 |
| P12931 | Proto-oncogene tyrosine-protein kinase Src | SRC | Y419 |
| O15357 | Phosphatidylinositol-3,4,5-trisphosphate 5-phosphatase 2 | SHIP-2 | Y886 |
| O95297 | Myelin protein zero-like protein 1 | PZR | Y263 |
| P07355 | Annexin A2 | ANXA2 | Y235 |
| P28482 | Mitogen-activated protein kinase 1 | ERK2 | Y187 |
| P49023 | Paxillin | PXN | Y118 |
| P56945 | Breast cancer anti-estrogen resistance protine 1 | P130Cas | Y234 |
| Q00401 | Neural Wiskott-Aldrich syndrome protein | N-WASP | Y256 |
| P29317 | Ephrin type-A receptor 2 | EphA2 | Y772 |
| P16591 | Proto-oncogene tyrosine-protein kinase FER | Fer | Y402 |

Figure 1C:
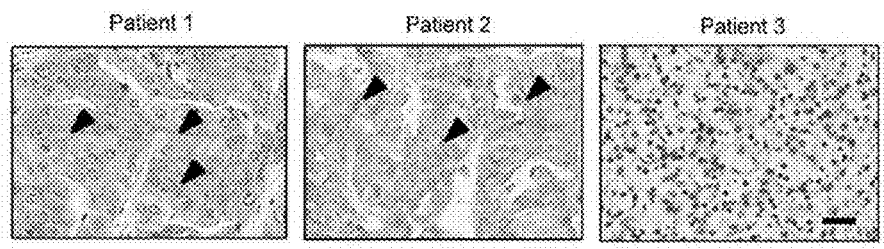
Figure 1D:
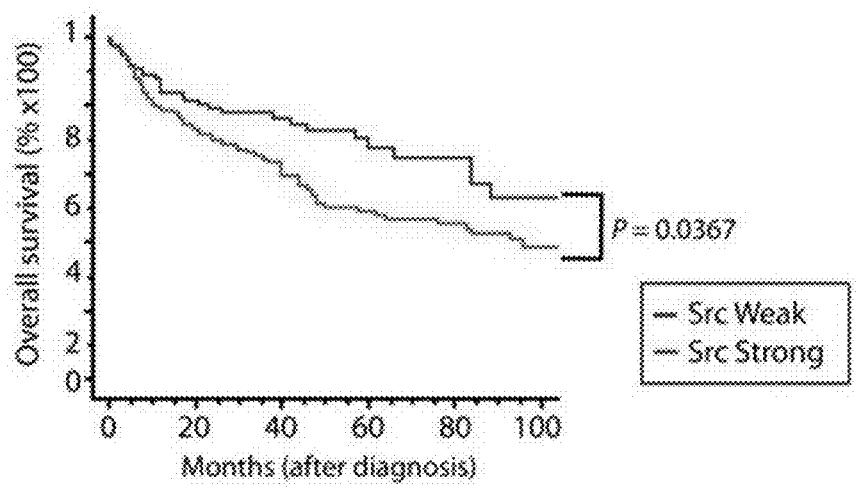

A human RCC tissue microarray was analyzed with samples from 215 patients for Src protein expression by immunohistochemistry (FIG. 1C). A significant positive association was found between total Src protein, which correlates with cytoplasmic staining, and active Src, which correlates with membranous staining (p=0.0185, Table 5). RCC patient samples with strong Src immunostaining had reduced survival when compared to those with weak expression (p=0.0367; FIG. 1D). In addition, multivariate analysis with stage (grouped as organ confined (pT1, 2) or advanced (pT3, 4)) and Fuhrman grade revealed that strong Src levels independently predicted against survival (p=0.02, Table 5). Since VHL loss is a dominant feature in RCC pathogenesis, it was tested whether Src and VHL protein levels were associated. Src positively correlated with the presence of VHL protein (p=0.04; Table 2).

TABLE 2

Clinicopathological correlations for Src in patients with RCC sampled on tissue microarray (cohort 1)

A: Association between membranous and cytoplasmic Src expression.

| Src | cytoplasm neg/weak N (%) | cytoplasm strong N (%) | total | P |
|---|---|---|---|---|
| membrane neg/weak N (%) | 102 (94.4) | 6 (6.6) | 108 (100) | 0.0185 |
| membrane strong N (%) | 94 (84.7) | 17 (15.3) | 111 (100) | |

Contingency table analysis and Chi Square test.
B: Multivariate analysis with tumor stage, Fuhrman grade, Src cytoplasmic and membranous expression (combined).

| Variables | 95% CI for RR | RR | P |
|---|---|---|---|
| Fuhrman grade | 1.228-2.177 | 1.635 | 0.001 |
| Tumor stage (pT1/2 vs pT3/4) | 1.616-4.158 | 2.592 | <0.001 |
| Src cyt/mem (n/n, n/w, w/w, w/n vs n/s, w/s, s/s, s/w, s/n) | 1.083-2.524 | 1.654 | 0.02 |

Cox proportional hazard regression analysis.
CI = Confidence interval; RR = Relative risk
n = negative; w = weak; s = strong expression.
C: Correlation between Src and VHL expression in RCC.

| | VHL | | | |
|---|---|---|---|---|
| Src | Strong N (%) | Weak N (%) | Negative N (%) | |
| Strong | 57 (62) | 53 (52) | 7 (33) | P = 0.04* |
| Weak | 35 (38) | 49 (48) | 14 (67) | |

*Contingency table analysis and Chi-square test.
215 tumor cores from 215 patients Example 3

VHL-WT RCC cells are sensitive to dasatinib

Figure 2A:
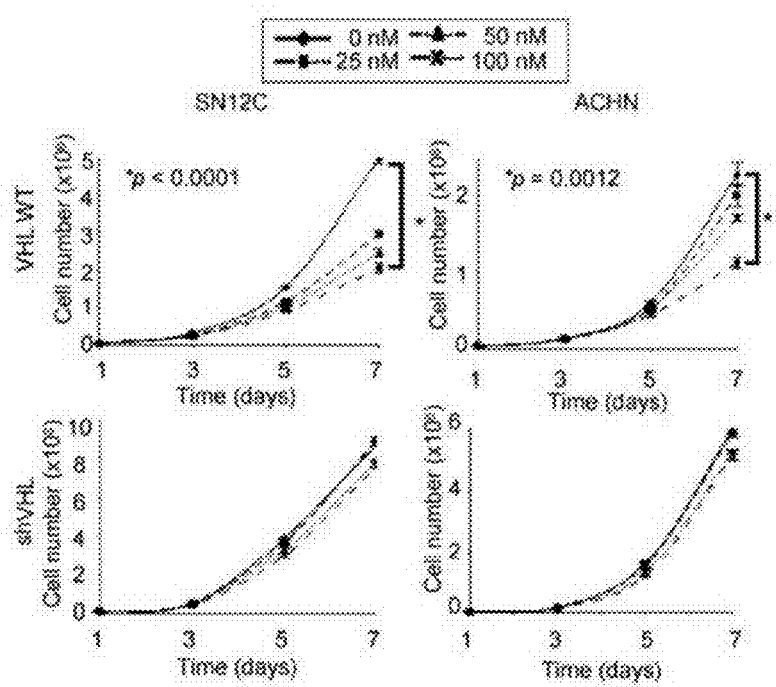

To evaluate whether VHL expression determined sensitivity to Src inhibitors, SN12C and SN12C-shVHL cells as well as ACHN or ACHN-shVHL papillary RCC cells were treated with dasatinib. It was found that dasatinib reduced proliferation of VHL-WT SN12C and ACHN cells but not their shVHL counterparts (FIG. 2A). The inhibition of proliferation by dasatinib correlated with an increase in G1 arrested cells and a corresponding decrease in S-phase cells as determined by propidium iodide (PI) staining (Table 3).

TABLE 3

Cell Cycle Analysis of shVHL lines -
VHL-wild type or shVHL SN12C and ACHN cell lines were treated with the indicated concentration of dasatinib and cell cycle profiles were examined by flow cytometry.
Cell population (%) in each cell cycle phase was quantified.

| | Dasatinib (nM) | | | |
|---|---|---|---|---|
| | 0 | 25 | 50 | 100 |
| SN12C | | | | |
| VHL WT | | | | |
| $G_1$ | 52.4 | 59.5 | 63.6 | 70.0 |
| S | 30.9 | 23.9 | 22.8 | 16.3 |
| $G_2/M$ | 15.4 | 15.0 | 11.7 | 11.7 |
| shVHL | | | | |
| $G_1$ | 45.0 | 45.2 | 45.4 | 46.1 |
| S | 35.6 | 36.9 | 38.5 | 35.3 |
| $G_2/M$ | 19.1 | 17.5 | 15.7 | 18.5 |
| ACHN | | | | |
| VHL WT | | | | |
| $G_1$ | 54.7 | 59.7 | 62.1 | 64.5 |
| S | 26.5 | 25.8 | 17.6 | 15.7 |
| $G_2/M$ | 16.8 | 12.6 | 16.0 | 14.9 |
| shVHL | | | | |
| $G_1$ | 51.4 | 50.2 | 47.6 | 46.1 |
| S | 33.0 | 37.4 | 36.7 | 40.8 |
| $G_2/M$ | 13.9 | 9.8 | 14.2 | 10.9 |

Figure 2B:
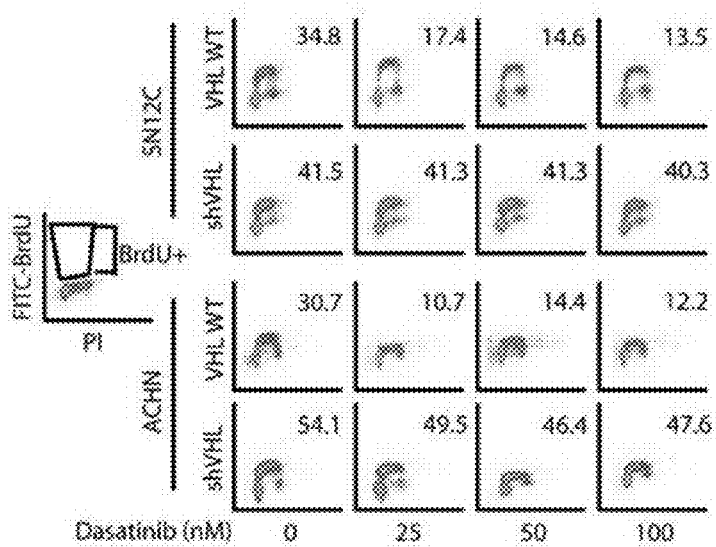
Figure 6A:
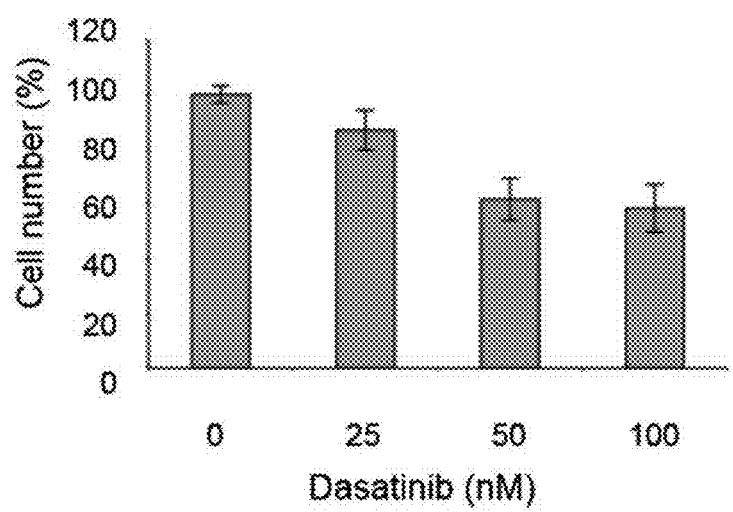
FIG. 6A shows that VHL-WT RXF-393 cells are sensitive to dasatinib. 5×10$^4$ RXF-393 cells were treated with vehicle, 25, 50 or 100 nM dasatinib 24 hours post-seeding. Effect of dasatinib on cell growth was recorded by cell count after 96 hours. Data are presented as the mean±S.D. (n=3).
Figure 6B:
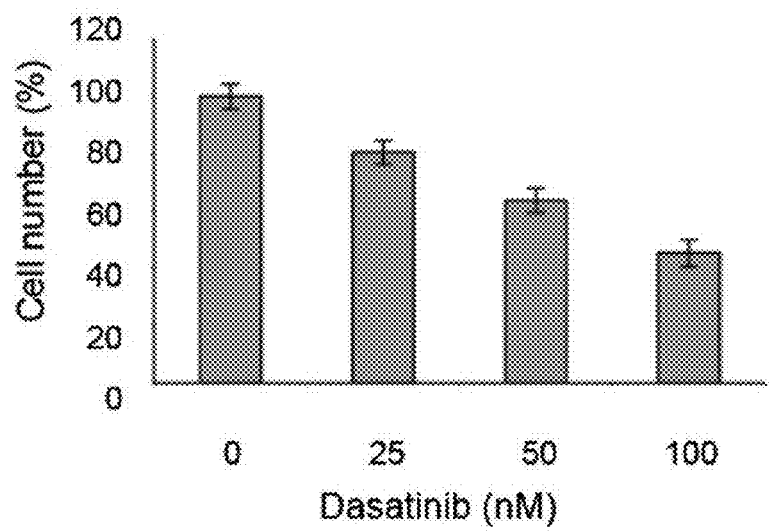
FIG. 6B shows that VHL-WT Caki-1 cells are sensitive to dasatinib. Conditions identical to those used in FIG. 6A described above.
Figure 7A:
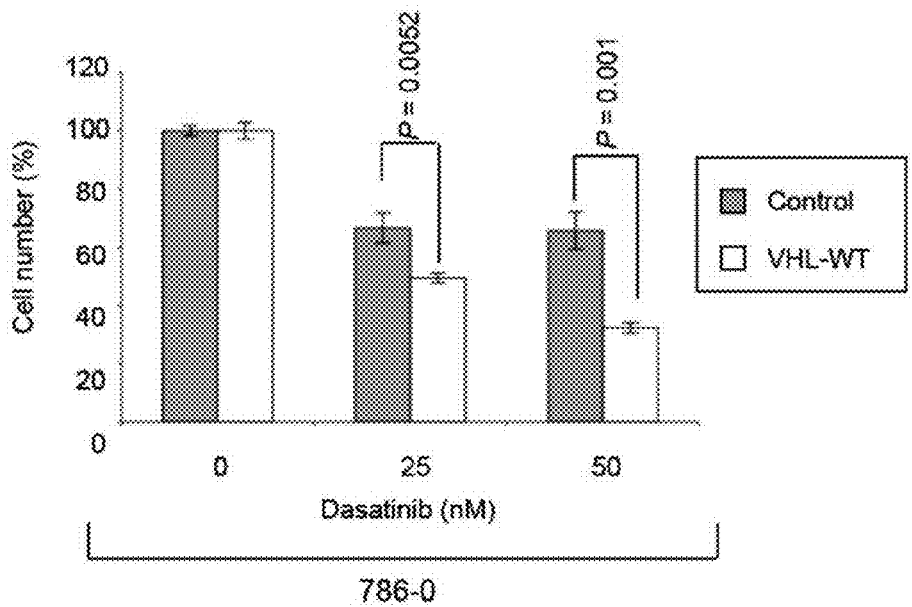
FIGS. 7A and 7B show that reconstitution of VHL enhances sensitivity to dasatinib in VHL-null 786-0 cells. 5×10$^4$ 786-0 control or 786-0 cells expressing VHL (VHL-WT) were treated with vehicle, 25 or 50 nM dasatinib 24 hours post-seeding. Effect of dasatinib on cell proliferation was monitored by cell count after 96 hours. Levels of total and phosphospecific forms of Src and FAK after 24 hours vehicle/dasatinib treatments were determined by immunoblot. α-tubulin, loading control.
Figure 7B:
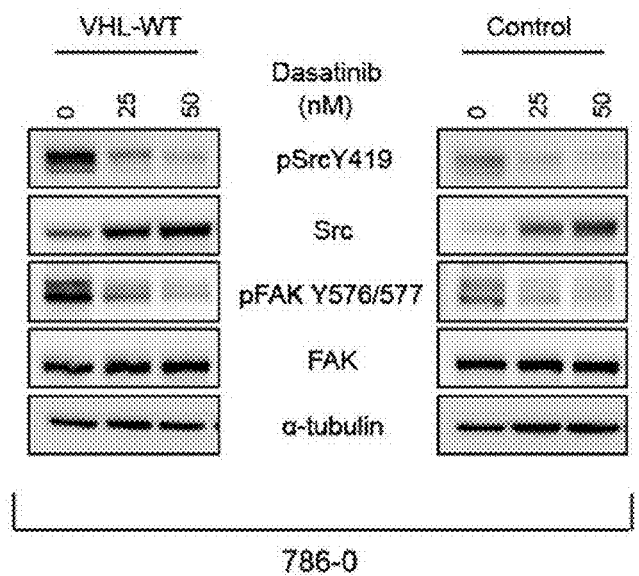

Moreover, BrdU staining showed dasatinib caused a dose-dependent decrease in DNA synthesis in VHL-WT SN12C and ACHN cells but not their shVHL counterparts (FIG. 2B). No accumulation of a sub-G1 population was observed, indicating dasatinib is cytostatic in the cell lines tested. Similar results were obtained using VHL-WT RXF-393 and Caki-1 RCC cells compared to VHL-null 786-0 cells (FIG. 6 and FIG. 7). Correspondingly, ectopic expression of VHL in 786-0 cells conferred increased sensitivity to dasatinib (FIG. 7).

The determination that dasatinib inhibited proliferation of VHL-WT RCC cells prompted testing of whether dasatinib inhibited Src kinase activation and the phosphorylation of Src substrates. Flow cytometric and immunoblot analyses showed dasatinib reduced pY419 Src levels irrespective of VHL status (FIG. 2C). In agreement with the in vitro kinase assay (FIG. 1B), western blot analysis showed pY419 Src levels were higher in VHL-WT SN12C or ACHN cells compared to their shVHL counterparts. Dasatinib also caused total Src protein levels to increase regardless of VHL status (FIG. 2C and FIG. 7). This dasatinib-induced increase in total Src protein has been observed in other tumor types as well as with other classes of Src inhibitors and is consistent with the increased stability of dephosphorylated Src in vivo. In addition to inhibiting pY419 Src, dasatinib inhibited phosphorylation of the Src substrate Fak in VHL-WT cells (FIG. 2C). Surprisingly, the levels of pY576, 577 Fak in VHL knock-down cells were undetectable despite the presence of total Fak protein. These results indicate how dasatinib may selectively inhibit proliferation of VHL-WT cells compared to their VHL-null or VHL-low counterparts.

Figure 2D:
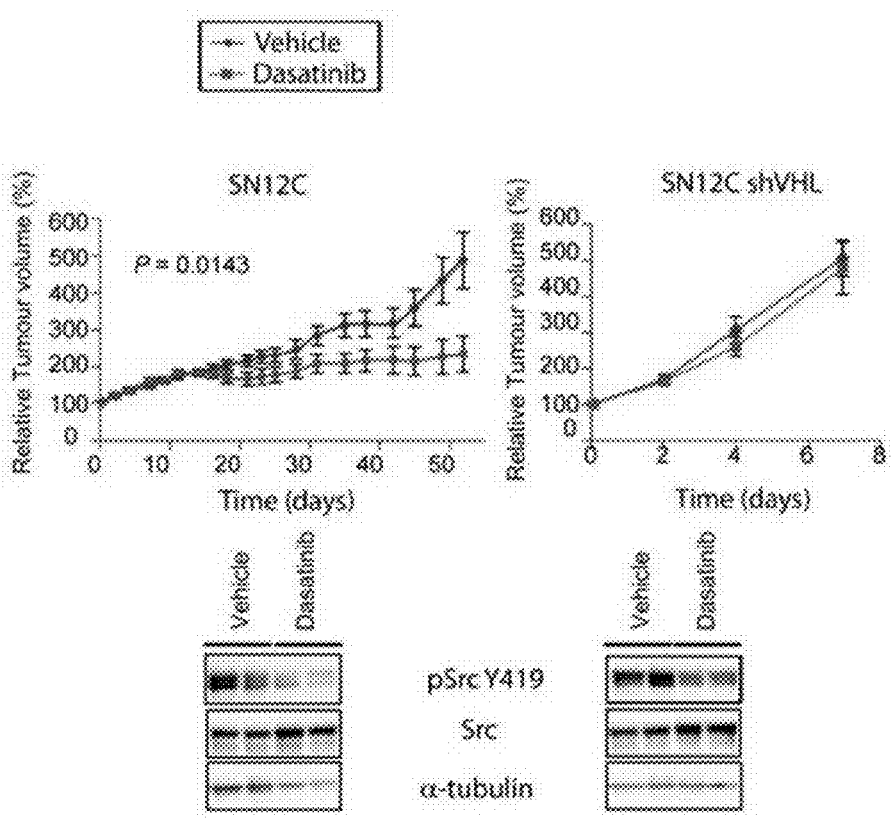
Figure 2E:
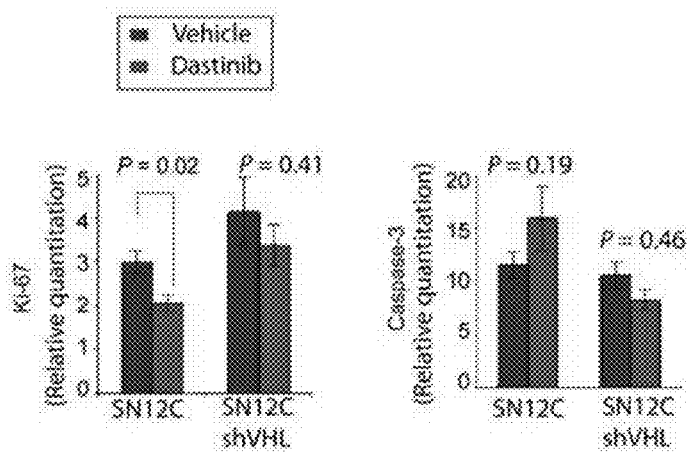

To evaluate the effect of dasatinib on tumor growth in vivo, SN12C and SN12C-shVHL cells were implanted subcutaneously into the flanks of nude mice. Daily treatment with dasatinib significantly reduced the growth of VHL-WT SN12C cells but had no effect on SN12C-shVHL cells, recapitulating the in vitro findings (compare FIGS. 2A and 2D). Dasatinib had no statistically significant effect on apoptosis in the xenograft tumors. Notably, administration of dasatinib resulted in a statistically significant reduction of Ki67 positive proliferating SN12C cells but not SN12C-shVHL cells (FIG. 2E). Together, these results demonstrate that VHL-WT RCC cells are more sensitive than shVHL cells to dasatinib in xenograft tumors as well as in vitro and that this sensitivity is mediated through a blockade on proliferation.

Figure 3A:
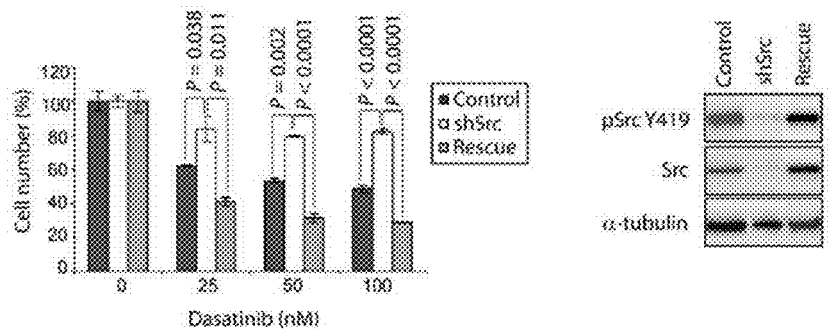
FIGS. 3A-3D show that Src is the relevant target of dasatinib in RCC.
Figure 3B:
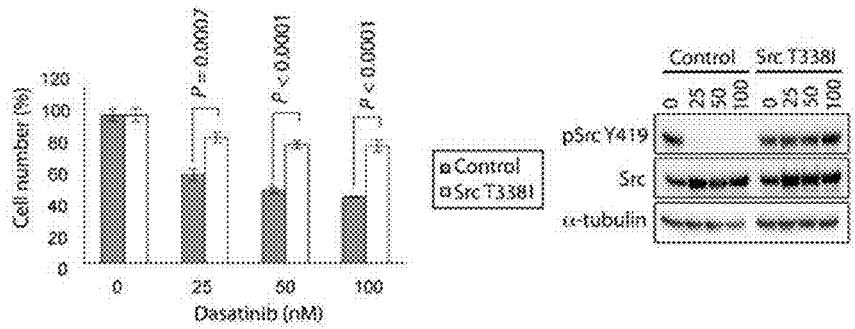
Figure 3C:
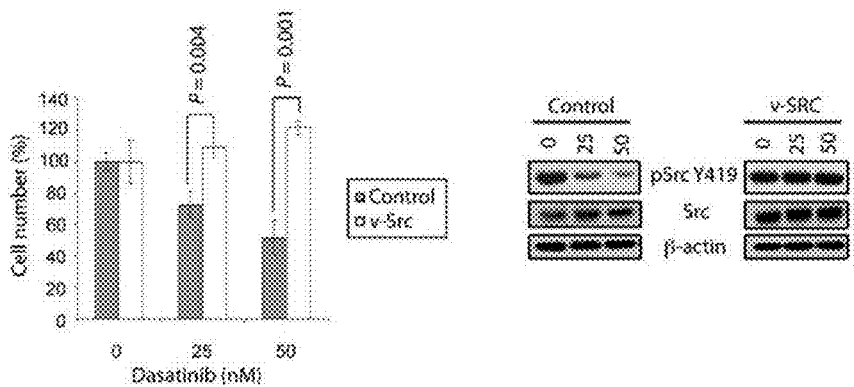
Figure 3D:
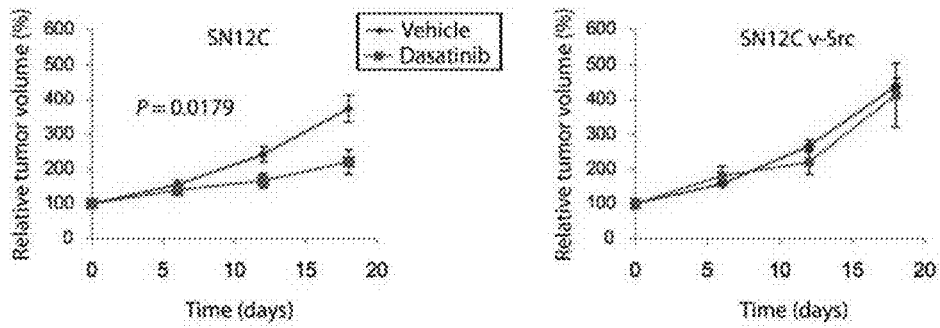
Figure 3D:
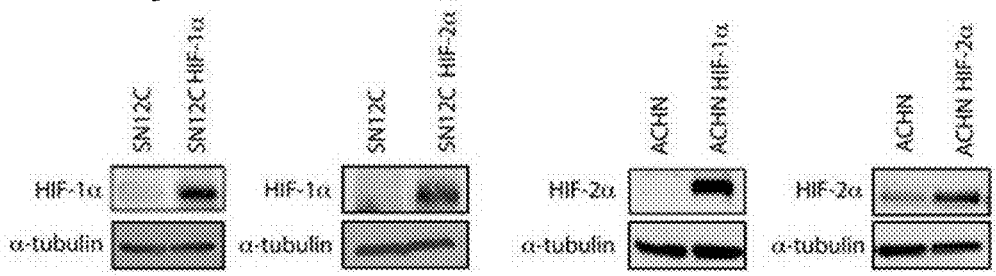
Figure 3D:
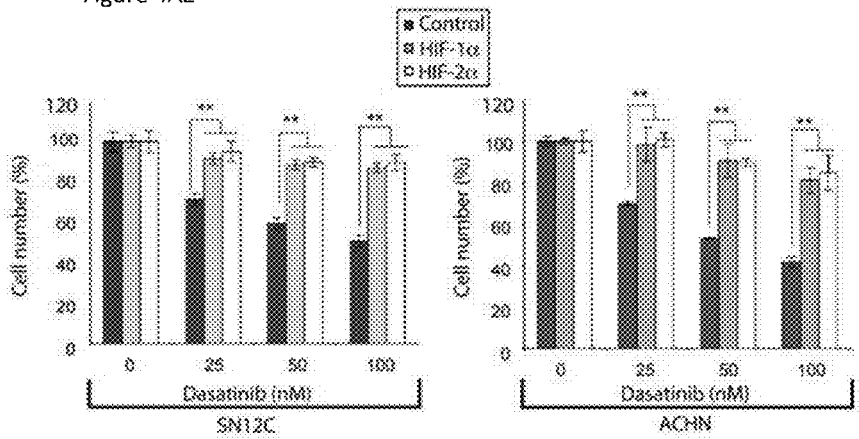
Figure 8:
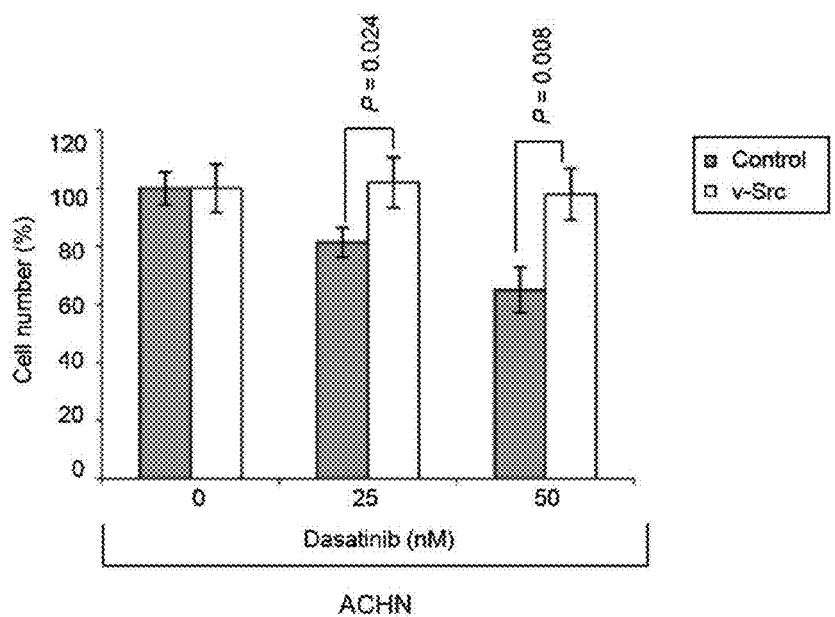
FIG. 8 shows that expression of v-Src renders VHL-WT cells resistant to dasatinib. 5×10$^4$ ACHN cells expressing either a control vector or v-Src were treated with vehicle, 25 or 50 nM dasatinib 24 hours post-seeding. Effect of dasatinib on cell growth was monitored by cell count after 96 hours. Data are presented as the mean±S.D. (n=3).

Next, it was asked whether the dasatinib-induced growth inhibitory effects on VHLWT RCC cells were due to Src inhibition. SN12C cells knocked down for Src (SN12C -shSrc) were resistant to dasatinib treatment (FIG. 3A). By contrast, rescue of SN12C-shSrc cells by expression of chicken Src, which is resistant to the human specific shRNA, restored dasatinib sensitivity. Moreover, stable expression of a dasatinib-resistant Src encoding a T3881 gatekeeper mutation, which prevents access of ATP-competitive inhibitors to the ATP binding pocket in Src, thereby protecting pY419 autophosphorylation, conferred resistance of SN12C cells to dasatinib (FIG. 3B). Similarly, expression of v-Src, which naturally expresses the T→I gatekeeper mutation, rendered VHL-WT SN12C and ACHN cells resistant to dasatinib (FIG. 3C and FIG. 8). Accordingly, SN12C-vSrc xenograft tumors grown in SCID mice were resistant to dasatinib whereas parental SN12C tumors remained dasatinib-sensitive (FIG. 3D).

Figure 9:
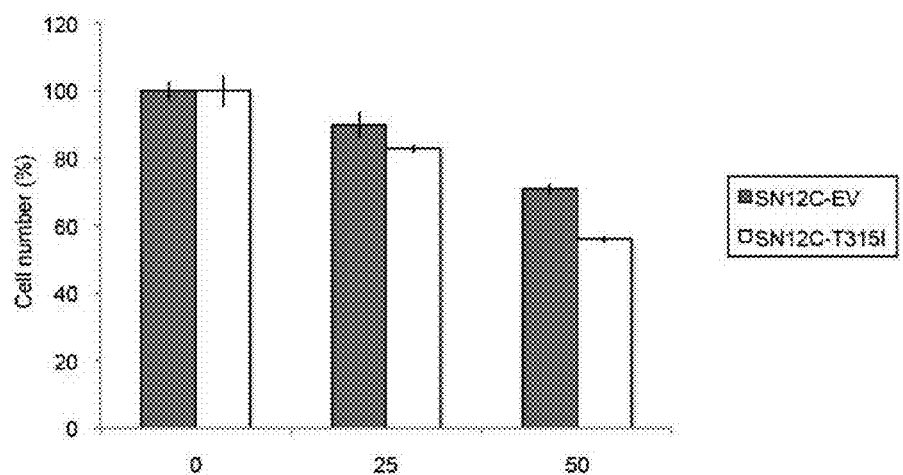
FIG. 9 shows that overexpression of BCR-ABL T315I mutant does not rescue sensitivity to Dasatinib. 5×10$^4$ SN12C cells expressing either a control vector (EV) or BCR-Abl T315I were treated with vehicle, 25 or 50 nM dasatinib 24 hours postseeding. Effect of dasatinib on cell proliferation was monitored by cell count after 96 hours. Data are presented as the mean±S.D. (n=3).
Figure 10A:
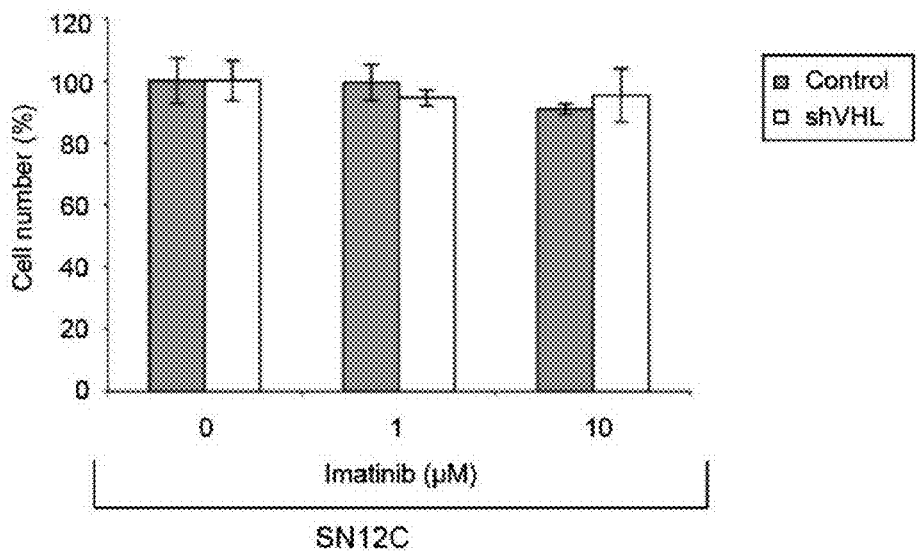
FIGS. 10A and 10B show that growth inhibition of VHL-WT cells by dasatinib is due to Src inhibition. 5×10$^4$ SN12C VHL-WT or shVHL cells were treated with the indicated doses of imatinib (FIG. 10A) or saracatinib (FIG. 10B). Effect of these drugs on cell proliferation was monitored by cell count 96 hours post-treatment. Data are presented as the mean±S.D. (n=3).
Figure 10B:
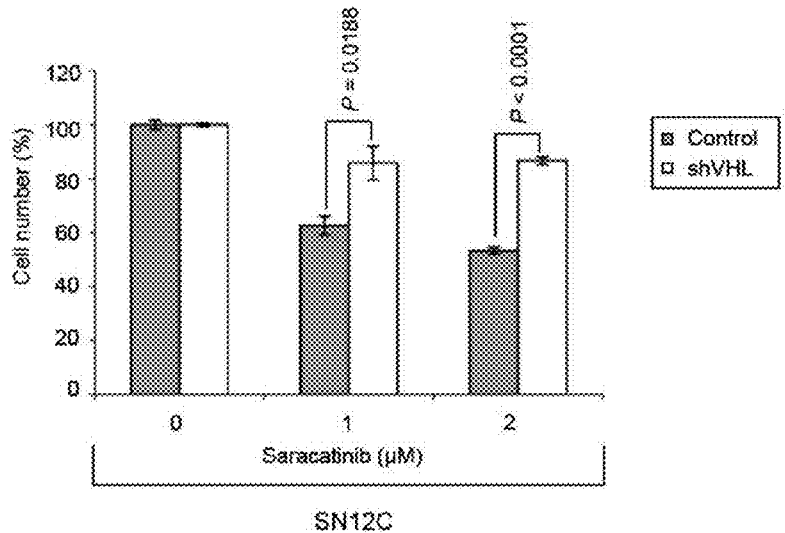
Figure 11:
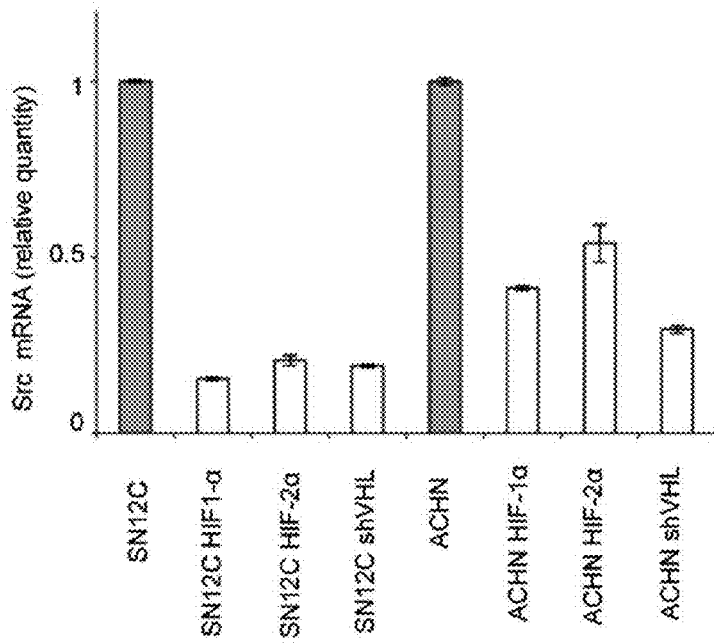
FIG. 11 shows that VHL status modulates Src expression at the transcriptional level. Transcriptional level of Src in SN12C or ACHN parental cells, SN12C or ACHN cells overexpressing constitutively stable HIF-1α-P564A (HIF-1α) or HIF-2α P405A, P853A (HIF-2α) mutants, or isogenic shVHL knockdown cells (n=3). Data are presented as the mean±S.D. Levels of mRNA in the parental cell lines are normalized to 1.

Several controls supported the finding that dasatinib suppressed proliferation in VHL-WT cells by inhibiting Src. First, SN12C cells expressing the BCR-ABL T315I gatekeeper mutant were sensitive to dasatinib, indicating the dasatinib resistance mediated by Src T3881 or v-Src was specific (FIG. 9). Secondly, treatment with imatinib, which inhibits ABL, PDGFR, and c-KIT but not Src, had no effect on the proliferation of SN12C or SN12C-shVHL cells (FIG. 9A). Finally, saracatinib, a structurally unrelated Src inhibitor, repressed proliferation of control SN12C cells but not shVHL cells (FIG. 10B).

Example 4

Constitutively Stabilized HIF Confers Resistance to Dasatinib in VHL-WT Cell

Since the E3 ligase activity of VHL negatively regulates HIF, it was asked whether expression of constitutively stable HIF would phenocopy VHL loss by conferring resistance to dasatinib in VHL-WT RCC cells. Indeed, SN12C and ACHN cells expressing constitutively stable HIF-1α-P564A or HIF-2α-P405A, P853A mutants contained reduced levels of Src mRNA and were resistant to the dasatinib-mediated G1 arrest observed in parental SN12C and ACHN cells (FIGS. 4A-4C, FIG. 11 and Table 4).

TABLE 4

Cell Cycle Analyses of HIF-α mutant cell lines
Cell cycle profiles of SN12C and ACHN cells expressing constitutively stable HIF-1α-P564A (HIF-1α) or HIF-2α-P405A, P853A (HIF-2α) mutants were analyzed by flow cytometry 48 hours post treatment with dasatinib.
Cell population % in each cell cycle phase was quantified.

| | Dasatinib (nM) | | | |
|---|---|---|---|---|
| | 0 | 25 | 50 | 100 |
| SN12C | | | | |
| VHL WT | | | | |
| $G_1$ | 58.3 | 60.1 | 59.2 | 60.4 |
| S | 26.7 | 25.1 | 27.6 | 26.5 |
| $G_2/M$ | 13.3 | 13.3 | 11.4 | 11.1 |
| HIF-2α | | | | |
| $G_1$ | 56.4 | 54.8 | 55.7 | 49.7 |
| S | 20.9 | 23.6 | 21.4 | 27.8 |
| $G_2/M$ | 21.5 | 20.6 | 22.1 | 21.3 |
| ACHN | | | | |
| VHL WT | | | | |
| $G_1$ | 57.3 | 59.2 | 56.4 | 60.1 |
| S | 21.6 | 21.6 | 25.1 | 17.6 |
| $G_2/M$ | 17.7 | 17.1 | 16.0 | 22.0 |
| HIF-2α | | | | |
| $G_1$ | 59.4 | 53.9 | 51.9 | 55.3 |
| S | 20.8 | 27.7 | 27.0 | 24.2 |
| $G_2/M$ | 17.5 | 16.1 | 19.3 | 17.7 |

Figure 4B:
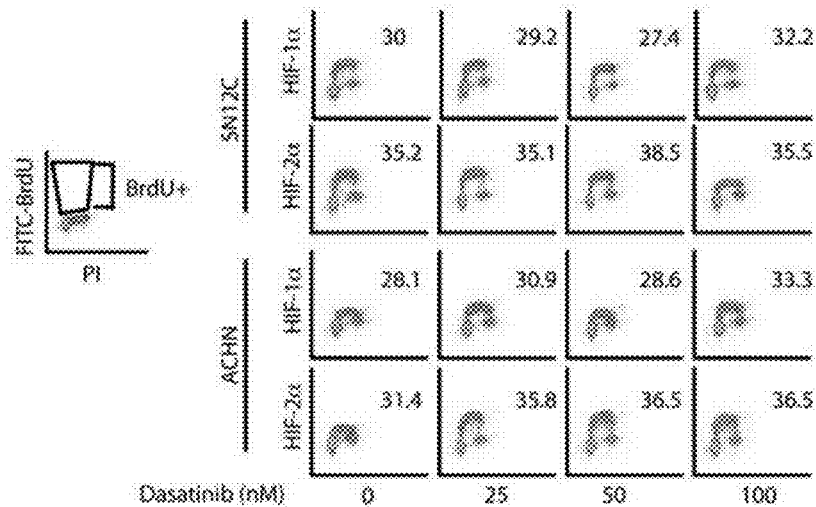
Figure 4C:
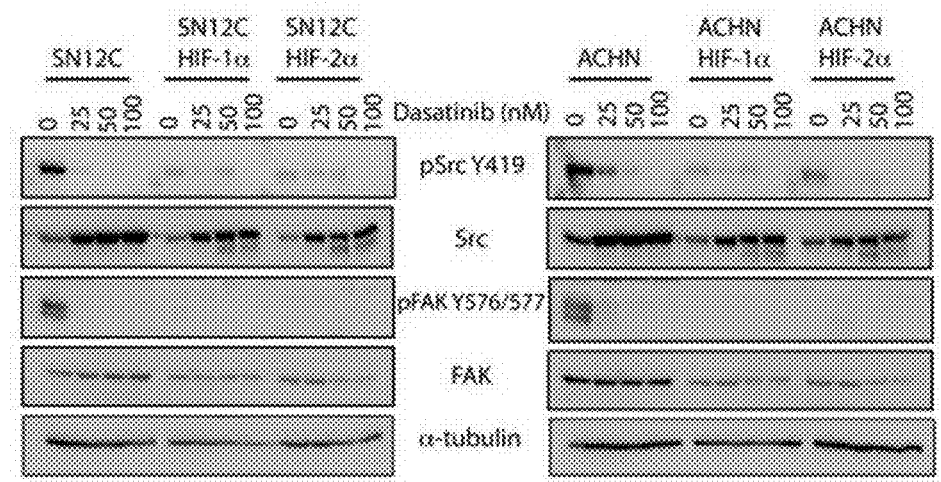
Figure 4D:
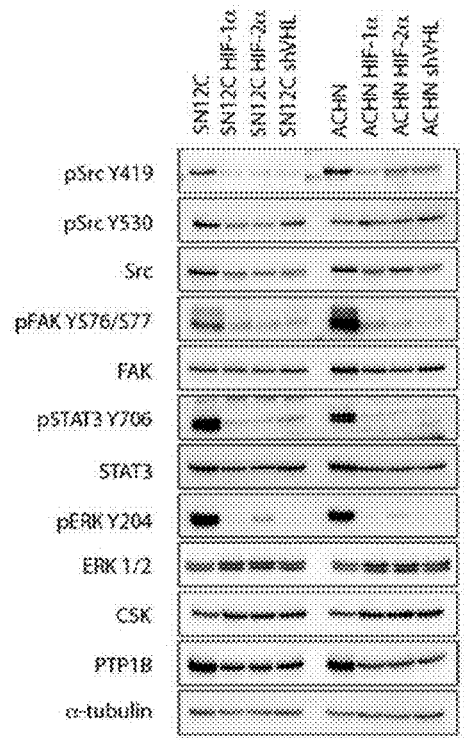
Figure 12:
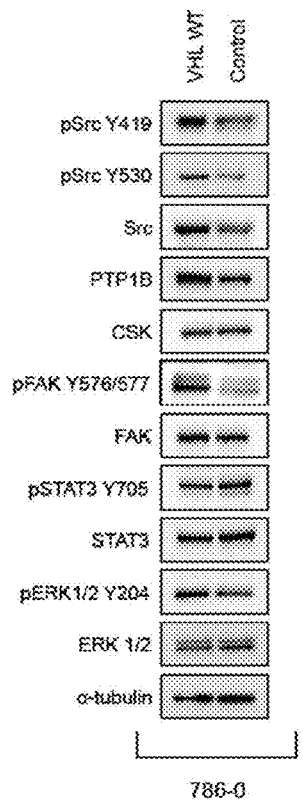
FIG. 12 shows that reconstitution of VHL alters SRC signaling output. Control and VHL-WT expressing cells were analyzed for total and phospho-specific forms of Src, PTP1B, CSK, FAK, STAT3 and ERK1/2 by immunoblot. α-tubulin, loading control.

Correspondingly, constitutively stable HIF-1α and HIF-2α inhibited Src signaling output in VHL-WT RCC cells as determined by immunoblot of pY419 Src and phosphorylated Src substrates, including pY576, 577FAK, pY703STAT3 and pY204ERK (FIG. 4D). Conversely, ectopic expression of VHL in VHL-null 786-0 RCC cells resulted in an increase in both total and pY419 Src as well as the phosphorylation and activation of its downstream targets when compared to the parental cells (FIGS. 12 and 7). Together, these results indicate that HIF represses VHL-mediated Src signaling output.

Figure 4E:
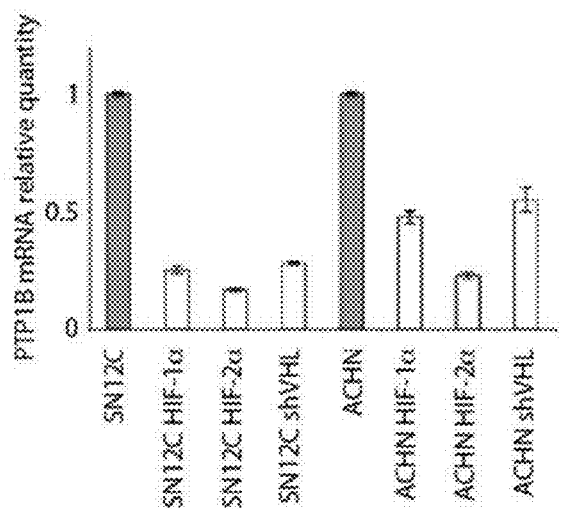
Figure 4F:
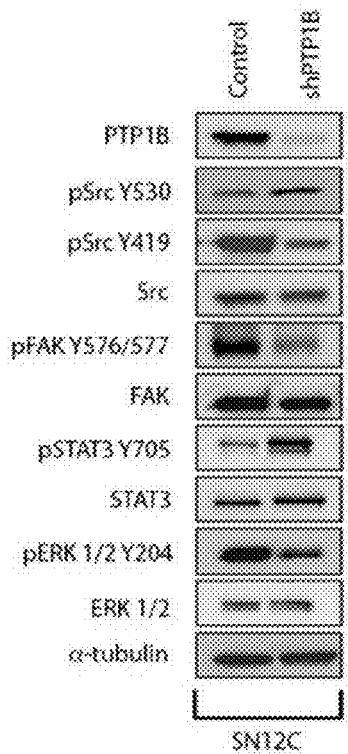
Figure 4G:
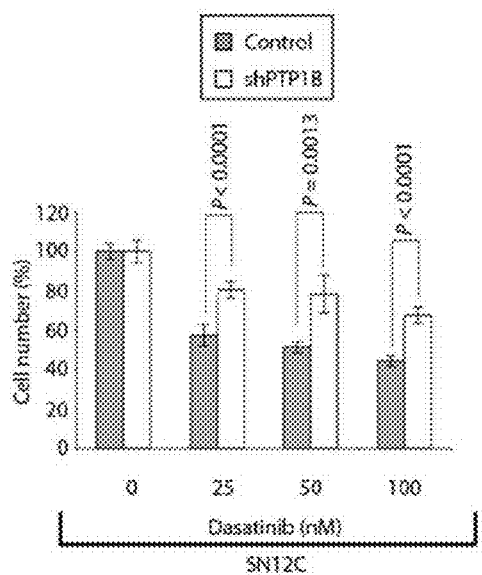
Figure 13A:
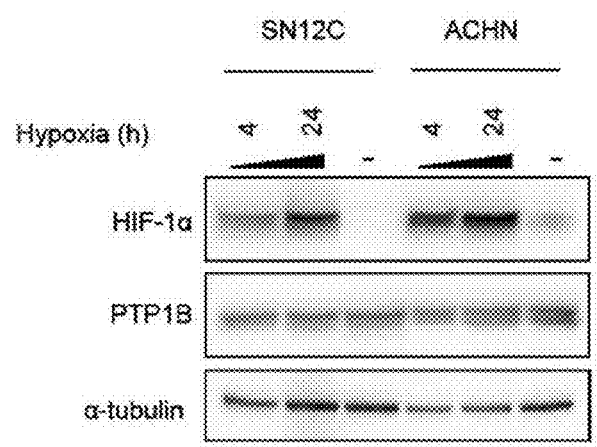
FIGS. 13A and 13B show that PTP1B expression levels are altered in response to hypoxia.
Figure 13B:
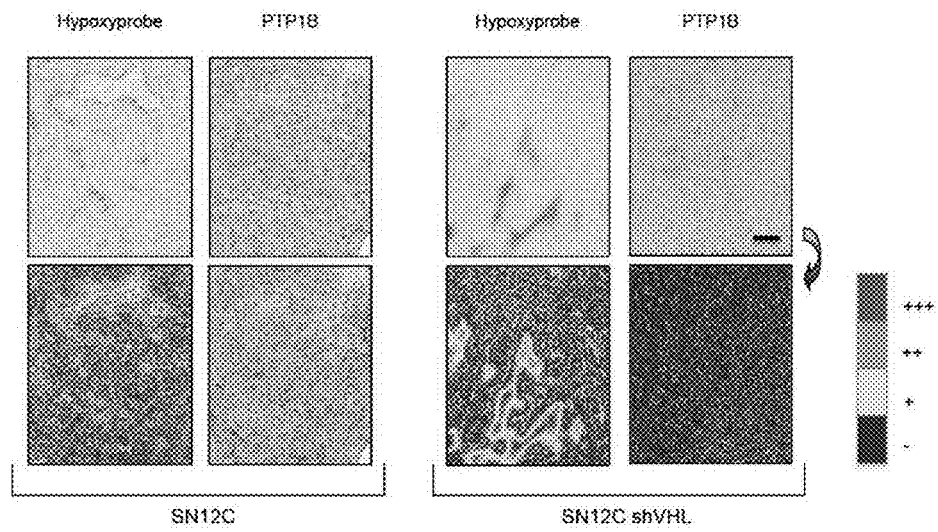

The ability of constitutively stable HIF mutants to promote dasatinib resistance and repress Src signaling output indicated HIF may repress an activator of Src activity. Consistent with this possibility, expression of PTP1B protein and mRNA, which activates Src by dephosphorylation of Y530, was consistently lower in shVHL cells or RCC cells that ectopically express constitutively stable HIF (FIGS. 4D and 4E). Correspondingly, PTP1B protein was decreased in VHL-null 786-0 cells compared to VHL-restored 786-O-VHL cells (FIG. 12). Biochemical analysis of Src signaling output indicated PTP1B knockdown phenocopied expression of constitutively stable HIF in VHL-WT cells. SN12C-shPTP1B cells contained reduced pY419 Src and the levels of phosphorylated Src substrates, including pY576, 577FAK and pY204ERK (FIG. 4F) and were relatively resistant to dasatinib-mediated growth inhibition (FIG. 4G). Only pY703STAT3 was unaffected by PTP1B knockdown, which may result from a PTP1B specific effect on STAT3 and its regulator, JAK. As a control, SN12C cells were exposed to hypoxia in vitro or in xenograft tumors. It was found that HIF was stabilized but PTP1B was unaffected, indicating HIF -regulated PTP1B expression may be different under hypoxic conditions (FIG. 13).

Figure 14:
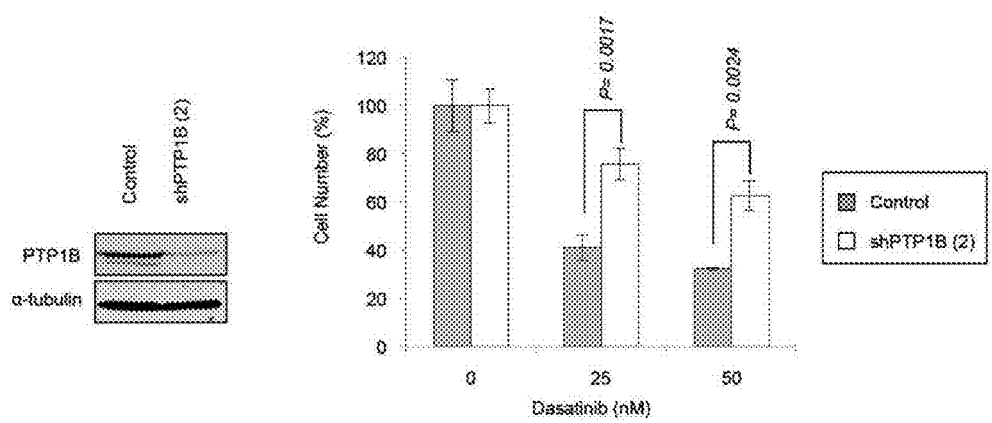
FIG. 14 shows that PTP1B shRNA also rescues sensitivity to dasatinib. SN12C (control) and SN12C-shPTP1B (targeting sequence #2) cells were analyzed for expression of PTP1B by immunoblot. α-tubulin, loading control. Cell proliferation following 96 hours exposure to vehicle alone or to 25 or 50 nM dasatinib was assessed by cell count. Data are presented as the mean±S.D. (n=3).
Figure 15:
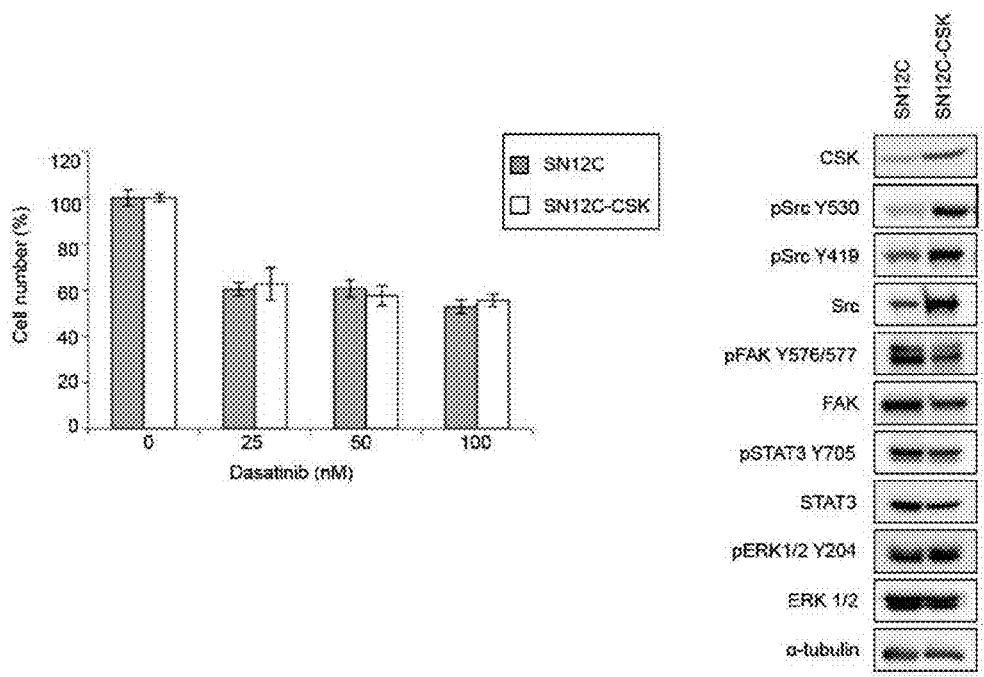
FIG. 15 shows that CSK overexpression does not confer dasatinib-resistance to SN12C. Control SN12C cells or CSK-overexpressing SN12C cells were analyzed by cell count following 96 hours treatment with vehicle, 25, 50 or 100 nM dasatinib. Data are presented as the mean±S.D. (n=3). The levels of CSK, as well as total and phospho-specific forms of Src, FAK, STAT3, and ERK 1/2 were monitored by immunoblot. α-tubulin, loading control.

Consistent with the reduced activation of Src, PTP1B knockdown cells were less sensitive to dasatinib compared to control cells (FIG. 4G and FIG. 14). By contrast, overexpression of the Src regulator Csk in SN12C cells had no effect on dasatinib sensitivity or Src signaling output (FIG. 15), which is consistent with work by others that Csk phosphorylation of Src pY530 is complex. Together, these results indicate that sensitivity to dasatinib appears to correlate with the capacity to inhibit Src's signaling output.

Figure 16:
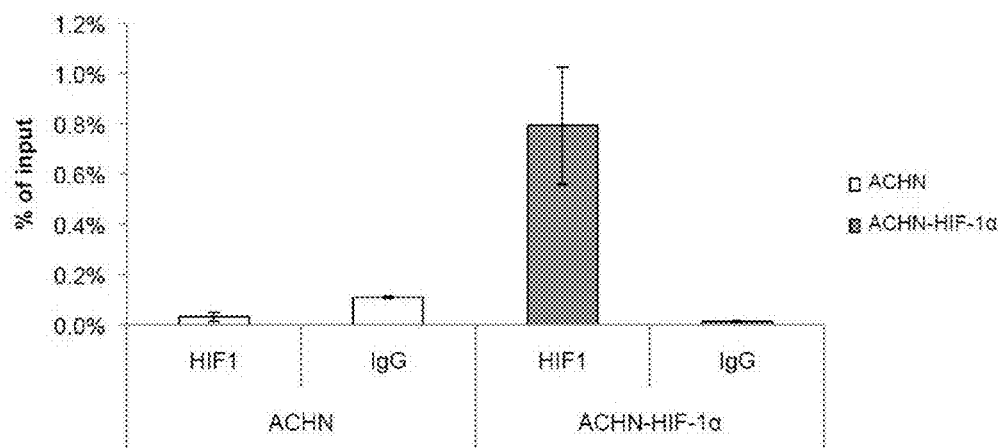
FIG. 16 shows that chromatin Immunoprecipitation analysis at the PTP1B promoter. ChIP analysis using anti-HIF1α or non-specific IgG antibodies was performed on sheared chromatin from ACHN or ACHN-HIF-1α cells. Co-immunoprecipitated DNA containing the PTP1B hypoxia response element (HRE) was quantified using real-time PCR and presented as percent (%) of input.

In addition to repressed levels of PTP1B protein, RCC cells with VHL knockdown or expression of constitutively stable HIF had reduced levels of PTP1B mRNA (FIG. 4E), indicating HIF may repress PTP1B transcription. In support of this finding, chromatin immunoprecipitation (ChIP) revealed that HIF is enriched at a putative hypoxia response element in the PTP1B promoter in ACHN-cells expressing constitutively stable HIF-1α—P564A but not in parental ACHN cells (FIG. 16). This result indicates that HIF mediated transcriptional regulation of the PTP1B gene contributes to the repression of Src signaling output in VHL-null RCC cells.

Example 5

Interaction of VHL, HIF, PTP1B and Src in RCC patients

The identification of a HIF-regulated VHL-PTP1B-Src signaling axis in RCC cell lines provided additional markers to rigorously interrogate the presence of this pathway in RCC patients. A tissue microarray was constructed from a second cohort of 131 patients with RCC and performed immunohistochemistry for VHL, HIF-2α, which is the primary driver in VHL-null RCC, Src and PTP1B. As controls, the HIF transcriptional target, CA-IX was analyzed, as well as the Src substrate pFAK.

Figure 5A:
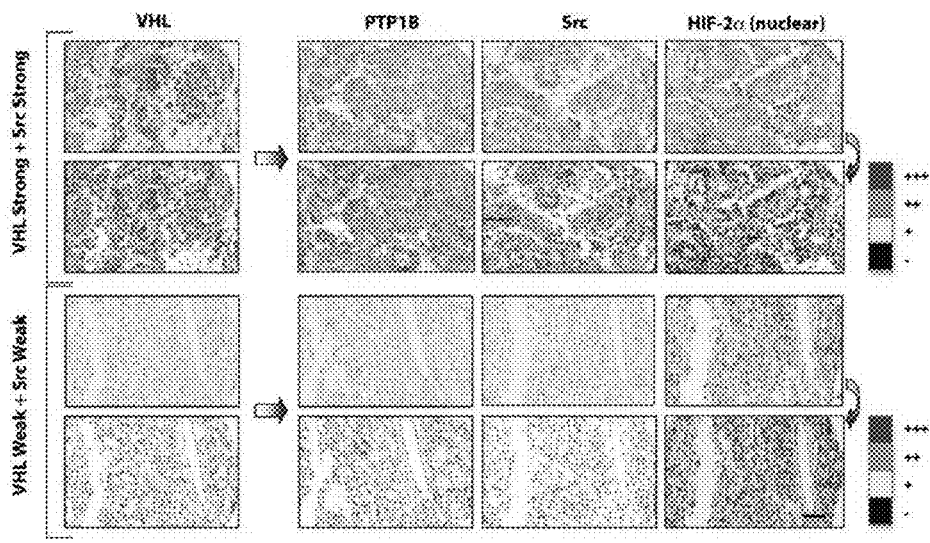
FIGS. 5A-5D demonstrate the inter-relationships between VHL, HIF-α, Src and PTP1B in RCC patients.
Figure 17:
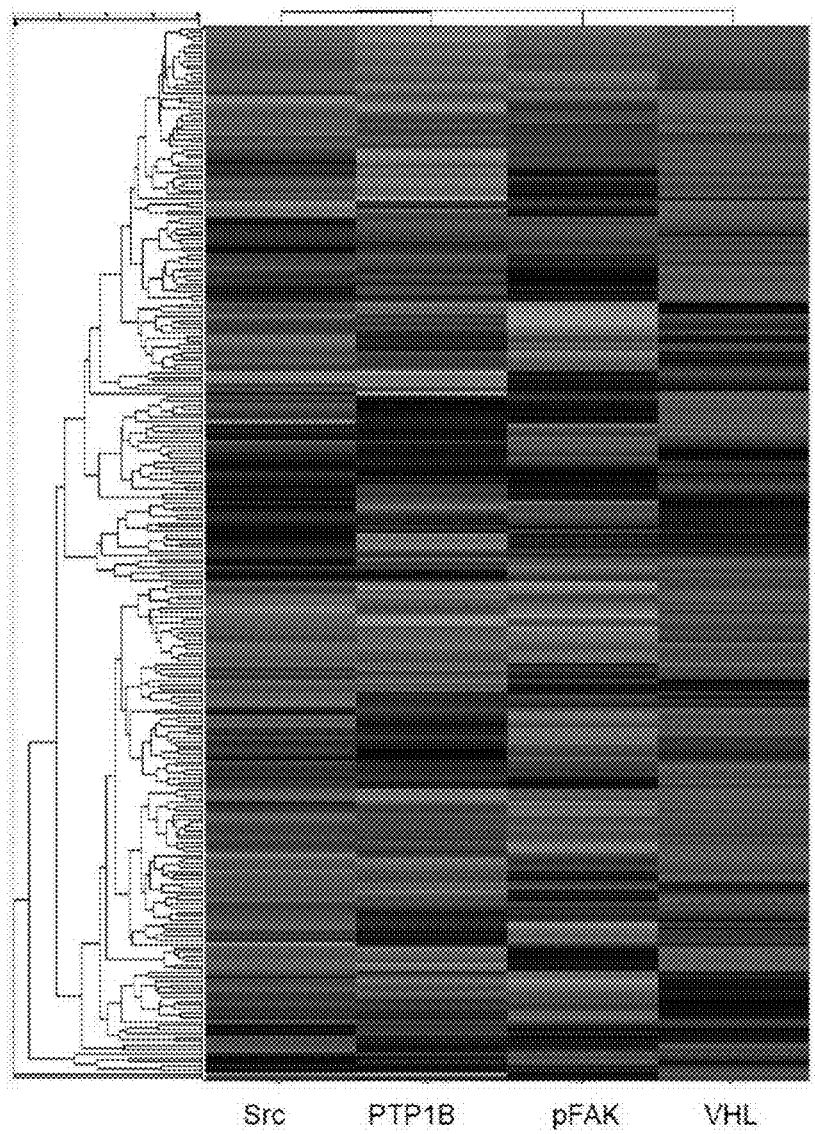
FIG. 17 is a heatmap showing hierarchical clustering of the protein expression data of VHL, Src, pFAK and PTP1B. The data was generated from the cytoplasmic staining intensity scores as measured by quantitative digital image analysis and normalized by centering on the median. HIF-2α immunostaining is not shown, as its reported values were scored by quantifying nuclear positivity. Each row corresponds to a patient sample and each column represents the indicated biomarker (Src, PTP1B, pFAK, VHL). The columns were also clustered as shown by the simple tree at the top of the figure.

Quantification was performed with automated digital image analysis algorithms to rigorously and systematically measure staining intensity (FIG. 5A). An unsupervised hierarchical clustering of the tumors on the basis of the expression of VHL, Src, pFAK and PTP1B was used to generate a heatmap (FIG. 17). VHL, Src and PTP1B showed the most similar expression patterns while pFAK and VHL expression were similar, despite pFAK expression being generally lower than the other markers.

Figure 5B:
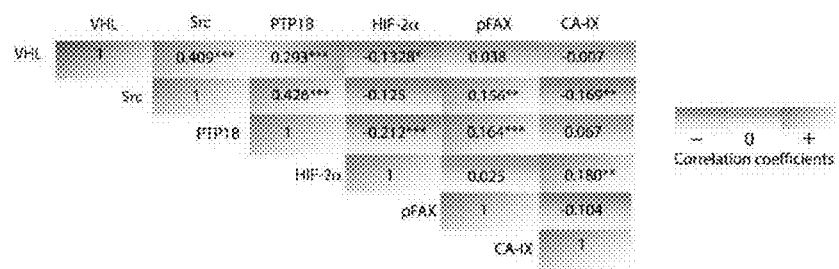
Figure 5C:
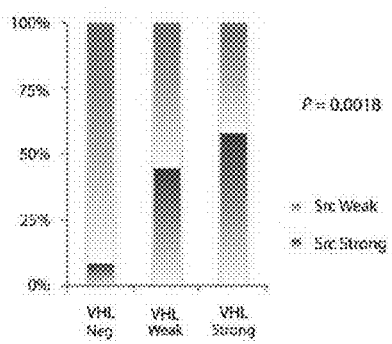

In agreement with the initial RCC clinical dataset (Table 5), a Spearman rank correlation test of the second RCC clinical dataset again revealed a positive correlation between VHL and Src ($r=0.409$; $p<0.001$; FIG. 5B). Using these more stringent analyses, only 8% (1/12) of VHL negative tumors had strong Src expression, while 58% (69/119) of VHL strong tumors had strong Src expression, indicating a highly correlative relationship between VHL and SRC ($p=0.0018$; FIG. 5C and Table 6). Conversely, the relationship between VHL and HIF-2α revealed a significant negative correlation ($r=-0.132$; $p=0.036$). In agreement with the in vitro findings, PTP1B positively correlated with VHL ($r=0.293$; $p<0.001$) but negatively correlated with HIF-2α ($r=-0.212$; $p=0.001$), indicating patient tumors with VHL loss or HIF-2α overexpression may have reduced PTP1B expression. Controls showed positive correlations between HIF-2α and CA-1× and between Src and pFAK as expected (FIG. 5B.) A multiple linear regression showed VHL ($p<0.0001$) and PTP1B ($p<0.0001$) to be predictors of Src expression. Additionally, VHL ($p<0.0001$) and HIF-2a ($p=0.0021$) were independent predictors of PTP1B levels (Table 5).

TABLE 5

Coefficient estimates for two predefined models PTP1B and Src, all variables have been log transformed.

| Outcome and Covariates | Estimated Coefficient | 95% CI | P |
|---|---|---|---|
| Src | | | |
| VHL | 0.146 | 0.096-0.196 | $2.55e^{-8}$ |
| PTP1B | 0.257 | 0.155-0.359 | $1.20e^{-6}$ |
| Intercept | 2.382 | 1.987-2.778 | $<2e^{-16}$ |
| PTP1B | | | |
| VHL | 0.164 | 0.104-0.225 | $2.11e^{-7}$ |
| HIF-2α | -0.228 | (-0.373)-(-0.084) | 0.00211 |
| Intercept | 4.298 | 3.796-4.800 | $<2e^{-16}$ |

Figure 5D:
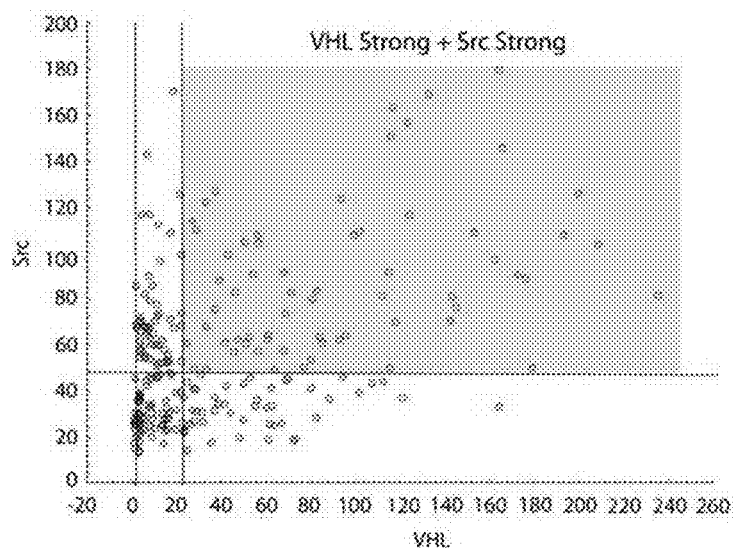

Next, the datapoints were extracted and organized them into a scatter plot representing patient subgroups defined by VHL and Src expression (FIG. 5D). Indeed, 28.6% of the patients were VHL-strong/Src-strong (Table 6).

Figure 18:
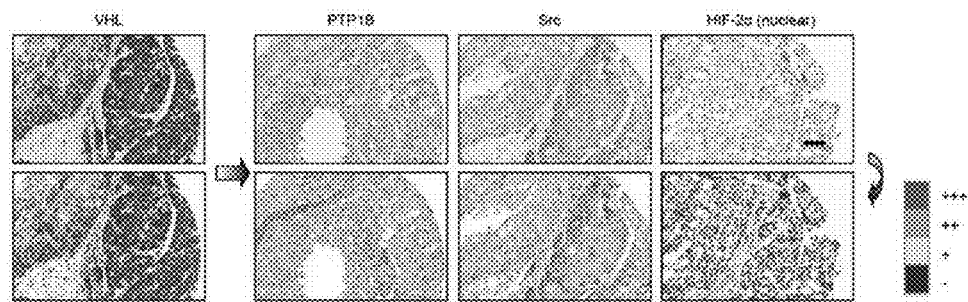
FIG. 18 shows the correlation between the expression levels of VHL, PTP1B, Src and HIF-2α. A tumor from a representative transitional cell carcinoma patient was immunostained with VHL, PTP1B, Src and HIF-2α using DAB based detection method and subsequently counterstained with hematoxylin. The scanned slides were then subjected to quantitative digital image analysis. Corresponding markup images of the color deconvolution algorithm with intensity ranges are shown. For HIF-2α, the algorithm was applied for nuclear immunostaining. Scale bar is 50 µm.

Next, it was tested whether this RCC immunohistochemistry profile could be applied to other cancers to predict sensitivity to dasatinib. Using a clinical dataset of transitional cell carcinomas of the bladder, it was found the same correlations between VHL, Src, HIF-2α and PTP1B (FIG. 18). Taken together, these findings indicate that the immunophenotype of the VHL-PTP1B-Src signaling axis comprises a biomarker signature that not only defines a biologically distinct subgroup of RCC that benefit from dasatinib or similar Src inhibitors but also points to a wider clinical applicability for these predictive biomarkers in identifying sensitivity to Src inhibitors.

TABLE 6

Correlation between Src and VHL expression in patients with RCC sampled on tissue microarray (cohort 2).

| | VHL | | | |
|---|---|---|---|---|
| Src | Strong N (%) | Weak N (%) | Negative N (%) | |
| Strong | 69 (58) | 49 (45) | 1 (8) | P = 0.0018 |
| Weak | 50 (42) | 61 (55) | 11 (92) | |

*Contingency table analysis and Chi-square test.
262 tumor cores from 131 patients
Numbers may not add up to 262 because of missing cores

TABLE 7

Spearman Rho correlations between the biomarkers immunostaining in transitional cell carcinoma of the bladder.

| | Correlation Coefficient | P |
|---|---|---|
| VHL | | |
| SRC | 0.493 | 0.027 |
| PTP1B | 0.477 | 0.034 |
| HIF-2α | -0.408 | 0.07 |
| HIF-2α | | |
| PTP1B | -0.582 | 0.007 |

Figure 19:
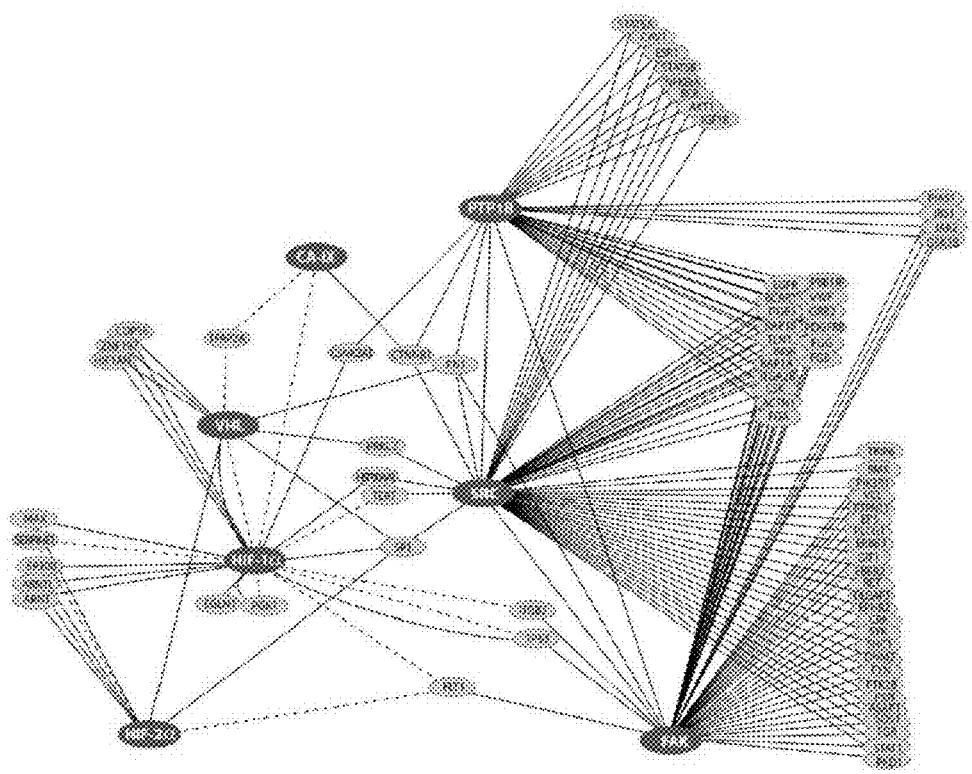
FIG. 19 shows the analysis of inter-relationships between VHL, HIF-a, Src and PTP1B in RCC Patients. ROCK-BCFG network interaction map: Nodes indicate the markers experimentally analyzed in vitro and in vivo. Solid lines denote physical interactions and dotted lines denote transcriptional regulation events.

The cooperating events involved in mediating sensitivity to dasatinib were then explored by applying a systems-based approach to map the potential protein-protein interactions, transcriptional information and the signaling networks they impact by using the ROCK-BCFG database. The interaction network searches were seeded with targets identified in the experiments and defined a protein interaction network containing 82 nodes that indicate an underlying signaling network involving Src, PTP1B, CA-IX, FAK and VHL together with the transcriptional regulators HIF-1α, HIF2-α and Sp1 (FIG. 19).

Despite playing a central role in multiple tumorigenic signaling networks, Src itself is rarely mutated in cancers. The data indicate that one mechanism by which tumor cells amplify Src kinase activity is by utilizing gene-autonomous drivers such as PTP1B to dephosphorylate the kinase autoinhibitory domain. The ability of PTP1B knockdown to confer resistance to dasatinib (FIG. 4G and FIG. 14) indicates PTP1B may augment Src signaling in RCC cells by channeling inputs from upstream oncogenes, including Ras. Unlike PTP1B knockdown, overexpression of Csk did not alter Src pY419 status (FIG. 15), indicating the regulation of Src activation by Csk is complex. These findings are consistent with reports that Csk phosphorylation of Src Y530 requires interaction of Csk with Csk binding protein (Cbp) in lipid rafts, indicating that analysis of Src pY419 or pY530 levels by immunoblot is insufficient to detect minute or compartment-specific changes in Src activation. The finding that hypoxia-induced stabilization of HIF failed to affect PTP1B expression is in agreement with the HIF dependent but hypoxia-independent regulation of Ror2 (FIG. 13), and is consistent with the model that HIF-mediated inhibition of PTP1B requires that HIF be constitutively stabilized by VHL loss and not by fluctuating $O_2$ levels present in VHLWT tumors.

Successful implementation of targeted therapies in molecularly heterogeneous cancers requires robust predictive biomarkers. The development of EGFR mutation analysis for stratification of patients with non-small cell lung cancer to EGFR inhibitors supports the feasibility of this approach. Therefore, the initial examination of VHL and Src on routinely processed human RCC samples assessed the clinical significance of Src expression. Indeed, RCC patient samples with strong Src expression had a statistically significant reduced overall survival when compared to those with weak expression. This analysis also revealed a positive correlation between VHL and Src using a semiquantitative scoring protocol that biased toward sensitivity relative to specificity. The VHL-Src relationship was more rigorously interrogated with enhanced specificity by analyzing VHL, Src, as well as their downstream effector molecules in a second cohort of human RCC tumors. This analysis used unbiased digital image analysis algorithms to objectively quantify staining intensities and to determine correlations between these molecules. Indeed, the VHL-Src relationship was one of the strongest correlations found.

In addition, the relationships among VHL, Src, HIF, PTP1B, pFAK and CA-IX were strongly reflected in patient tumors, consistent with the in vitro results. The presence of these associations in clinical samples reveals the strength of the molecular networks identified and supports the testing of these markers in future clinical trials. Inactivation of the VHL tumor suppressor gene is the most prevalent driver mutation in RCC, accounting for approximately 60% of all tumors. Thus, despite the fact that approximately 40% of RCC patients have VHL-positive cancer, they are treated as VHL-negative cancers. Unfortunately, the absence of biomarker-driven treatment protocols in RCC together with the fact that VHL-positive patients are excluded from many registration trials precludes meaningful understanding of the mechanisms of response or resistance. Thus, the singular approach currently used to treat RCC underscores the need for rational treatment strategies for VHL-positive RCC. These findings indicate that Src inhibition represent a likely rational treatment option in renal cancers that have retained VHL protein expression. Additionally, analyzing functional readouts of VHL and Src activity by HIF, CA-IX and pFAK expression would enhance specificity since functional VHL would confer low HIF and CA-IX expression while elevated Src signaling output would correlate with increased pFAK levels.

Indeed, since Src inhibitors such as dasatinib and saracatinib have been clinically tested, the data indicate that these biomarker analyses may be rapidly translated to a clinical trial in patients with metastatic RCC. Collectively, the results indicate a fundamental change in RCC treatment is warranted. Specifically, patients should be selected upfront based on the presence of a molecular phenotype. The simplicity of this approach lies in two elements: using immunohistochemical-based assays on routinely processed clinical samples and the targeting of a well-characterized oncogene for which there already exists clinically active drugs.

Example 6

A Diagnostic Test for VHL $^+$ Cancer

This example describes a diagnostic test, for example in a clinical setting, for detecting VHL$^+$ cancer, such as VHL$^+$ RCC in a subject. However, one skilled in the art will appreciate that methods that deviate from these specific methods can also be used to successfully detect VHL$^+$ cancer, such as VHL$^+$ RCC in a subject.

In some embodiments, expression of at least VHL is assessed. In some embodiments, expression of at least VHL and Src is tested. In some embodiments, at least VHL, Src and one of PTP1B, HIF or CA-IX is tested. In some embodiments, at least VHL, Src, PTP1B, HIF and CA-IX are tested. In some embodiments VHL, Src and a combination of PTP1B, HIF and CA-IX are tested. The results of the test are provided to a user (such as a clinician or other health care worker, laboratory personnel, or patient) in a perceivable output that provides information about the results of the test. In some examples, the output can be a paper output (for example, a written or printed output), a display on a screen, a graphical output (for example, a graph, chart, voltametric trace, or other diagram), or an audible output.

In other examples, the output is a numerical value, such as an expression level of VHL, Src, PTP1B, HIF and/or CA-IX expression in the sample or a relative amount of VHL, Src, PTP1B, HIF and/or CA-IX expression in the sample as compared to a threshold level of expression. In additional examples, the output is a graphical representation, for example, a graph that indicates the level of VHL, Src, PTP1B, HIF and/or CA-IX expression in the sample from the subject on a standard curve. In a particular example, the output (such as a graphical output) shows the threshold level of expression that indicates that the cancer is sensitive to a Src inhibitor.

The output can provide quantitative information (for example, an amount of VHL, Src, PTP1B, HIF and/or CA-IX expression or an amount of VHL, Src, PTP1B, HIF and/or CA-IX expression relative to a control sample or value) or can provide qualitative information (for example, a diagnosis of RCC sensitive to Src inhibitors, a diagnosis of RCC resistant to Src inhibitors, or the risk of relapse free survival). In additional examples, the output can provide qualitative information regarding the expression levels of VHL, Src, PTP1B, HIF and/or CA-IX expression in the sample.

In some examples, the output is accompanied by guidelines for interpreting the data, for example, numerical or other limits that indicate whether or not a tumor is sensitive to a Src inhibitor. The guidelines need not specify whether or not to administer a Src inhibitor to the patient, although it may include such a recommendation. The indicia in the output can, for example, include one or more threshold levels of expression of one or more of VHL, Src, PTP1B, HIF and/or CA-IX which the recipient of the output may then use to interpret the results, for example, to arrive at a diagnosis, prognosis, or treatment plan. In other examples, the output can provide a recommended therapeutic regimen.

In some examples, the test may include determination of other clinical information (such as determining the amount of one or more additional cancer biomarkers in the sample). In some examples, the test includes an array, such as an antibody array or an electrochemical immunosensor array and the output of the test includes quantitative or qualitative information about VHL, Src, PTP1B, HIF and/or CA-IX expression (such as the amount of VHL, Src, PTP1B, HIF and/or CA-IX expression or an amount of change of VHL, Src, PTP1B, HIF and/or CA-IX expression relative to a control, or a relative increase or decrease of VHL, Src, PTP1B, HIF and/or CA-IX expression compared to the control), as well as quantitative or qualitative information about one or more additional proteins.

Example 7

Treatment of RCC

This example describes methods of treating RCC.

Based upon the teaching disclosed herein, VHL+RCC can be reduced or inhibited by administering a therapeutically effective amount of a composition, wherein the composition includes one or more agents that decrease the activity or expression of Src that is up-regulated in VHL+ RCC, thereby treating RCC in the subject.

In an example, a subject who has been diagnosed with RCC is identified by any of the methods disclosed herein. Following subject selection, a therapeutic effective dose of the composition including one or more therapeutic agents is administered to the subject. The amount of the composition administered to prevent, reduce, inhibit, and/or treat RCC or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., RCC) in a subject without causing a substantial cytotoxic effect in the subject.

In particular examples, the method includes screening a subject having or thought to have a RCC treatable by administration of a Src inhibitor. Subjects of an unknown disease status or condition can be examined, for example by determining if the subject has VLH+ RCC with overexpression of Src. Subjects found to (or known to) have VLH+ RCC, and thereby treatable are selected to receive a Src inhibitor.

The subject can be administered a therapeutic amount of a Src inhibitor. The Src inhibitor can be administered at doses of 0.0001 µg/kg body weight to about 10 mg/kg body weight per dose, such as 0.0001 µg/kg body weight—0.001 µg/kg body weight per dose, 0.001 µg/kg body weight—0.01 µg/kg body weight per dose, 0.01 µg/kg body weight—0.1 µg/kg body weight per dose, 0.1 µg/kg body weight—10 µg/kg body weight per dose, 1 µg/kg body weight—100 µg/kg body weight per dose, 100 µg/kg body weight—500 µg/kg body weight per dose, 500 µg/kg body weight per dose—1000 µg/kg body weight per dose, or 1.0 mg/kg body weight per dose—10 mg/kg body weight per dose. However, the particular dose can be determined by a skilled clinician. The Src inhibitor can be administered in several doses, for example continuously, daily, weekly, or monthly. The administration can concurrent or sequential.

The mode of administration can be any used in the art. The amount of the Src inhibitor administered to the subject can be determined by a clinician, and may depend on the particular subject treated. Specific exemplary amounts are provided herein (but the disclosure is not limited to such doses).

---

The invention claimed is:

1. A method of treating a cancer in a subject, the method comprising:

determining a first threshold level of expression of a first protein of SEQ ID NO: 7 by determining the expression level of the first protein by immunohistochemistry of a tissue section or cell line known to express SEQ ID NO: 7 and known to be sensitive to a Src inhibitor;

obtaining a sample from the subject, the sample comprising a cancer cell;

determining the expression level of the first protein in the sample by immunohistochemistry;

identifying the subject as likely to benefit from treatment with a Src inhibitor on the basis of the expression level of the first protein in the sample exceeding the first threshold level of expression; and treating the subject with a Src inhibitor.

2. The method of claim 1 further comprising:

determining a second threshold level of expression of a second protein of SEQ ID NO: 8 or SEQ ID NO: 10 by determining the expression level of the second protein by immunohistochemistry of a tissue section or cell line known to express SEQ ID NO: 8 or SEQ ID NO: 10 and known to be sensitive to a Src inhibitor;

determining the expression level of the second protein in the sample by immunohistochemistry; and identifying the subject as likely to benefit from treatment with the Src inhibitor on the basis of the expression level of the second protein exceeding a the second threshold level of expression.

3. The method of claim 1 further comprising:

determining a third threshold level of expression of a third protein of SEQ ID NO: 9 or SEQ ID NO: 11 by determining the expression level of the third protein by immunohistochemistry in a tissue section or cell line known not to express SEQ ID NO: 9 or SEQ ID NO: 11 and known to be sensitive to a Src inhibitor:

determining the expression level of the third protein by immunohistochemistry; and identifying the subject as likely to benefit from treatment with the Src inhibitor on the basis of the expression level of the third protein being less than the third threshold level of expression.

4. The method of claim 1 wherein the Src inhibitor is dasatinib.

5. The method of claim 1 wherein the cancer is renal cell carcinoma or transitional cell carcinoma.

6. The method of claim 3 wherein the tissue section or cell line known to express SEQ ID NO: 7 is also known to express SEQ ID NO: 8 or SEQ ID NO: 10 and also known not to express SEQ ID NO: 9 or SEQ ID NO: 11.

7. The method of claim 1 wherein the tissue section is part of a tissue microarray.

8. The method of claim 7 wherein the threshold level of expression is determined using more than one tissue section in the microarray.

* * * * *

SEQUENCE LISTING

<160> NUMBER OF SEQ ID NOS: 12

<210> SEQ ID NO 1
<211> LENGTH: 642
<212> TYPE: DNA
<213> ORGANISM: Homo sapiens

<400> SEQUENCE: 1

```
atgccccgga gggcggagaa ctgggacgag gccgaggtag gcgcggagga ggcaggcgtc      60
gaagagtacg gccctgaaga agacggcggg gaggagtcgg gcgccgagga gtccggcccg     120
gaagagtccg gccggagga actgggcgcc gaggaggaga tggaggccgg gcggccgcgg     180
cccgtgctgc gctcggtgaa ctcgcgcgag ccctcccagg tcatcttctg caatcgcagt     240
ccgcgcgtcg tgctgcccgt atggctcaac ttcgacggcg agccgcagcc ctacccaacg     300
ctgccgcctg gcacgggccg ccgcatccac agctaccgag gtcacctttg gctcttcaga     360
gatgcaggga cacacgatgg gcttctggtt aaccaaactg aattatttgt gccatctctc     420
aatgttgacg gacagcctat ttttgccaat atcacactgc cagtgtatac tctgaaagag     480
cgatgcctcc aggttgtccg gagcctagtc aagcctgaga attacaggag actggacatc     540
gtcaggtcgc tctacgaaga tctggaagac cacccaaatg tgcagaaaga cctggagcgg     600
ctgacacagg agcgcattgc acatcaacgg atgggagatt ga                         642
```

<210> SEQ ID NO 2
<211> LENGTH: 1308
<212> TYPE: DNA
<213> ORGANISM: Homo sapiens

<400> SEQUENCE: 2

```
atggagatgg aaaaggagtt cgagcagatc gacaagtccg ggagctgggc ggccatttac      60
caggatatcc gacatgaagc cagtgacttc ccatgtagag tggccaagct tcctaagaac     120
aaaaaccgaa ataggtacag agacgtcagt cccttttgacc atagtcggat taaactacat     180
caagaagata tgactatat caacgctagt ttgataaaaa tggaagaagc ccaaaggagt     240
tacattctta cccagggccc tttgcctaac acatgcggtc acttttggga gatggtgtgg     300
gagcagaaaa gcaggggtgt cgtcatgctc aacagagtga tggagaaagg ttcgttaaaa     360
tgcgcacaat actggccaca aaaagaagaa aaagagatga tctttgaaga cacaaatttg     420
aaattaacat tgatctctga agatatcaag tcatattata cagtgcgaca gctagaattg     480
gaaaacctta acccaagaa actcgagag atcttacatt ccactatac cacatggcct     540
gactttggag tccctgaatc accagcctca ttcttgaact ttcttttcaa agtccgagag     600
tcagggtcac tcagcccgga gcacgggccc gttgtggtgc actgcagtgc aggcatcggc     660
aggtctggaa ccttctgtct ggctgatacc tgcctcttgc tgatggacaa gaggaaagac     720
ccttcttccg ttgatatcaa gaaagtgctg ttagaaatga ggaagtttcg gatggggctg     780
atccagacag ccgaccagct gcgcttctcc tacctggctg tgatcgaagg tgccaaattc     840
atcatggggg actcttccgt gcaggatcag tggaaggagc tttcccacga ggacctggag     900
cccccacccg agcatatccc ccacctccc cggccaccca acgaatcct ggagccacac     960
aatgggaaat gcagggagtt cttcccaaat caccagtggg tgaaggaaga gacccaggag    1020
gataaagact gccccatcaa ggaagaaaaa ggaagcccct aaatgccgc accctacggc    1080
atcgaaagca tgagtcaaga cactgaagtt agaagtcggg tcgtgggggg aagtcttcga    1140
ggtgccaggg ctgcctcccc agccaaaggg gagccgtcac tgcccgagaa ggacgaggac    1200
catgcactga gttactggaa gcccttcctg gtcaacatgt gcgtggctac ggtcctcacg    1260
gccggcgctt acctctgcta caggttcctg ttcaacagca acacatag                 1308
```

<210> SEQ ID NO 3
<211> LENGTH: 2481
<212> TYPE: DNA
<213> ORGANISM: Homo sapiens

<400> SEQUENCE: 3

```
atggagggcg ccggcggcgc gaacgacaag aaaaagataa gttctgaacg tcgaaaagaa      60
aagtctcgag atgcagccag atctcggcga agtaaagaat ctgaagtttt ttatgagctt     120
gctcatcagt tgccacttcc acataatgtg agttcgcatc ttgataaggc ctctgtgatg     180
aggcttacca tcagctattt gcgtgtgagg aaacttctgg atgctggtga tttggatatt     240
gaagatgaca tgaaagcaca gatgaattgc tttatttga aagccttgga tggttttgtt     300
atggttctca cagatgatgg tgacatgatt tacatttctg ataatgtgaa caaatacatg     360
ggattaactc agtttgaact aactggacac agtgtgtttg attttactca tccatgtgac     420
catgaggaaa tgagagaaat gcttacacac agaaatggcc ttgtgaaaaa gggtaaagaa     480
caaaacacac agcgaagctt ttttctcaga atgaagtgta ccctaactag ccgaggaaga     540
```

-continued

| | |
|---|---|
| actatgaaca taaagtctgc aacatggaag gtattgcact gcacaggcca cattcacgta | 600 |
| tatgatacca acagtaacca acctcagtgt gggtataaga aaccacctat gacctgcttg | 660 |
| gtgctgattt gtgaacccat tcctcaccca tcaaatattg aaattccttt agatagcaag | 720 |
| actttcctca gtcgacacag cctggatatg aaattttctt attgtgatga aagaattacc | 780 |
| gaattgatgg gatatgagcc agaagaactt ttaggccgct caatttatga atattatcat | 840 |
| gctttggact ctgatcatct gaccaaaact catcatgata tgtttactaa aggacaagtc | 900 |
| accacaggac agtacaggat gcttgccaaa agaggtggat atgtctgggt tgaaactcaa | 960 |
| gcaactgtca tatataacac caagaattct caaccacagt gcattgtatg tgtgaattac | 1020 |
| gttgtgagtg gtattattca gcacgacttg attttctccc ttcaacaaac agaatgtgtc | 1080 |
| cttaaaccgg ttgaatcttc agatatgaaa atgactcagc tattcaccaa agttgaatca | 1140 |
| gaagatacaa gtagcctctt tgacaaactt aagaaggaac ctgatgcttt aactttgctg | 1200 |
| gccccagccg ctggagacac aatcatatct ttagattttg gcagcaacga cacagaaact | 1260 |
| gatgaccagc aacttgagga agtaccatta tataatgatg taatgctccc ctcacccaac | 1320 |
| gaaaaattac agaatataaa tttggcaatg tctccattac ccaccgctga aacgccaaag | 1380 |
| ccacttcgaa gtagtgctga ccctgcactc aatcaagaag ttgcattaaa attagaacca | 1440 |
| aatccagagt cactggaact ttcttttacc atgccccaga ttcaggatca gacacctagt | 1500 |
| ccttccgatg gaagcactag acaaagttca cctgagccta atagtcccag tgaatattgt | 1560 |
| ttttatgtgg atagtgatat ggtcaatgaa ttcaagttgg aattggtaga aaaacttttt | 1620 |
| gctgaagaca cagaagcaaa gaacccattt tctactcagg acacagattt agacttggag | 1680 |
| atgttagctc cctatatccc aatggatgat gacttccagt tacgttcctt cgatcagttg | 1740 |
| tcaccattag aaagcagttc cgcaagcccc gaaagcgcaa gtcctcaaag cacagttaca | 1800 |
| gtattccagc agactcaaat acaagaacct actgctaatg ccaccactac cactgccacc | 1860 |
| actgatgaat taaaaacagt gacaaaagac cgtatggaag acattaaaat attgattgca | 1920 |
| tctccatctc ctacccacat acataaagaa actactagtg ccacatcatc accatataga | 1980 |
| gatactcaaa gtcggacagc ctcaccaaac agagcaggaa aaggagtcat agaacagaca | 2040 |
| gaaaaatctc atccaagaag ccctaacgtg ttatctgtcg ctttgagtca agaactaca | 2100 |
| gttcctgagg aagaactaaa tccaaagata ctagctttgc agaatgctca gagaaagcga | 2160 |
| aaaatggaac atgatggttc actttttcaa gcagtaggaa ttggaacatt attacagcag | 2220 |
| ccagacgatc atgcagctac tacatcactt tcttggaaac gtgtaaaagg atgcaaatct | 2280 |
| agtgaacaga atggaatgga gcaaaagaca attatttaa taccctctga tttagcatgt | 2340 |
| agactgctgg ggcaatcaat ggatgaaagt ggattaccac agctgaccag ttatgattgt | 2400 |
| gaagttaatg ctcctataca aggcagcaga aacctactgc agggtgaaga attactcaga | 2460 |
| gctttggatc aagttaactg a | 2481 |

<210> SEQ ID NO 4
<211> LENGTH: 3159
<212> TYPE: DNA
<213> ORGANISM: Homo sapiens

<400> SEQUENCE: 4

| | |
|---|---|
| atggcagctg cttaccttga ccccaacttg aatcacacac caaattcgag tactaagact | 60 |
| cacctgggta ctggtatgga acgttctcct ggtgcaatgg agcgagtatt aaaggtcttt | 120 |
| cattattttg aaagcaatag tgagccaacc acctgggcca gtattatcag gcatggagat | 180 |

```
gctactgatg tcaggggcat cattcagaag atagtggaca gtcacaaagt aaagcatgtg    240
gcctgctatg gattccgcct cagtcacctg cggtcagagg aggttcactg gcttcacgtg    300
gatatgggcg tctccagtgt gagggagaag tatgagcttg ctcacccacc agaggagtgg    360
aaatatgaat tgagaattcg ttatttgcca aaaggatttc taaaccagtt tactgaagat    420
aagccaactt tgaatttctt ctatcaacag gtgaagagcg attatatgtt agagatagct    480
gatcaagtgg accaggaaat tgctttgaag ttgggttgtc tagaaatacg gcgatcatac    540
tgggagatgc ggggcaatgc actagaaaag aagtctaact atgaagtatt agaaaaagat    600
gttggtttaa agcgattttt tcctaagagt ttactggatt ctgtcaaggc caaaacacta    660
agaaaactga tccaacaaac atttagacaa tttgccaacc ttaatagaga agaaagtatt    720
ctgaaattct ttgagatcct gtctccagtc tacagatttg ataaggaatg cttcaagtgt    780
gctcttggtt caagctggat tatttcagtg gaactggcaa tcggcccaga gaaggaatc    840 agttacctaa cggacaaggg ctgcaatccc acacatcttg ctgacttcac tcaagtgcaa    900
accattcagt attcaaacag tgaagacaag gacagaaaag gaatgctaca actaaaaata    960
gcaggtgcac ccgagcctct gacagtgacg gcaccatccc taaccattgc ggagaatatg   1020
gctgacctaa tagatgggta ctgccggctg gtgaatggaa cctcgcagtc atttatcatc   1080
agacctcaga agaaggtga acgggctttg ccatcaatac aaagttggc caacagcgaa   1140 aagcaaggca tgcggacaca cgccgtctct gtgtcagaaa cagatgatta tgctgagatt   1200
atagatgaag aagatactta caccatgccc tcaaccaggg attatgagat tcaaagagaa   1260
agaatagaac ttggacgatg tattggagaa ggccaatttg gagatgtaca tcaaggcatt   1320
tatatgagtc cagagaatcc agctttggcg gttgcaatta aaacatgtaa aaactgtact   1380
tcggacagcg tgagagagaa atttcttcaa gaagccttaa caatgcgtca gtttgaccat   1440
cctcatattg tgaagctgat tggagtcatc acagagaatc ctgtctggat aatcatggag   1500
ctgtgcacac ttgagagct gaggtcattt ttgcaagtaa ggaaatacag tttggatcta   1560
gcatctttga tcctgtatgc ctatcagctt agtacagctc ttgcatatct agagagcaaa   1620
agatttgtac acagggacat tgctgctcgg aatgttctgg tgtcctcaaa tgattgtgta   1680
aaattaggag actttggatt atcccgatat atggaagata gtacttacta caaagcttcc   1740
aaaggaaaat tgcctattaa atggatggct ccagagtcaa tcaattttcg acgttttacc   1800
tcagctagtg acgtatggat gtttggtgtg tgtatgtggg agatactgat gcatggtgtg   1860
aagccttttc aaggagtgaa gaacaatgat gtaatcggtc gaattgaaaa tgggaaaga   1920 ttaccaatgc ctccaaattg tcctcctacc ctctacagcc ttatgacgaa atgctgggcc   1980
tatgacccca gcaggcggcc caggtttact gaacttaaag ctcagctcag cacaatcctg   2040
gaggaagaga aggctcagca agaagagcgc atgaggatgg agtccagaag acaggccaca   2100
gtgtcctggg actccggagg gtctgatgaa gcaccgccca gcccagcag accgggttat   2160 cccagtccga ggtccagcga aggatttat cccagcccac agcacatggt acaaaccaat   2220
cattaccagg tttctggcta ccctggttca catggaatca cagccatggc tgcagcatc   2280 tatccaggtc aggcatctct tttgaccaa acagattcat ggaatcatag acctcaggag   2340
atagcaatgt ggcagcccaa tgtggaggac tctacagtat tggacctgcg agggattggg   2400
caagtgttgc caacccatct gatggaagag cgtctaatcc gacagcaaca ggaaatggaa   2460
gaagatcagc gctggctgga aaagaggaa agatttctga aacctgatgt gagactctct   2520
```

-continued

| | |
|---|---|
| cgaggcagta ttgacaggga ggatggaagt cttcagggtc cgattggaaa ccaacatata | 2580 |
| tatcagcctg tgggtaaacc agatcctgca gctccaccaa agaaaccgcc tcgccctgga | 2640 |
| gctcccggtc atctgggaag ccttgccagc tcagcagcc ctgctgacag ctacaacgag | 2700 |
| ggtgtcaagc ttcagcccca ggaaatcagc cccctccta ctgccaacct ggaccggtcg | 2760 |
| aatgataagg tgtacgagaa tgtgacgggc ctggtgaaag ctgtcatcga gatgtccagt | 2820 |
| aaaatccagc cagccccacc agaggagtat gtccctatgg tgaaggaagt cggcttggcc | 2880 |
| ctgaggacat tattggccac tgtggatgag accattcccc tcctaccagc cagcacccac | 2940 |
| cgagagattg agatggcaca gaagctattg aactctgacc tgggtgagct catcaacaag | 3000 |
| atgaaactgg cccagcagta tgtcatgacc agcctccagc aagagtacaa aaagcaaatg | 3060 |
| ctgactgctg ctcacgccct ggctgtggat gccaaaaact tactcgatgt cattgaccaa | 3120 |
| gcaagactga aaatgcttgg gcagacgaga ccacactga | 3159 |

<210> SEQ ID NO 5
<211> LENGTH: 1380
<212> TYPE: DNA
<213> ORGANISM: Homo sapiens

<400> SEQUENCE: 5

| | |
|---|---|
| atggctcccc tgtgccccag cccctggctc cctctgttga tcccggcccc tgctccaggc | 60 |
| ctcactgtgc aactgctgct gtcactgctg cttctggtgc ctgtccatcc ccagaggttg | 120 |
| ccccggatgc aggaggattc ccccttggga ggaggctctt ctggggaaga tgacccactg | 180 |
| ggcgaggagg atctgcccag tgaagaggat tcacccagag aggaggatcc accggagag | 240 |
| gaggatctac ctggagagga ggatctacct ggagaggagg atctacctga agttaagcct | 300 |
| aaatcagaag aagagggctc cctgaagtta gaggatctac ctactgttga ggctcctgga | 360 |
| gatcctcaag aaccccagaa taatgcccac agggacaaag aaggggatga ccagagtcat | 420 |
| tggcgctatg gagcgacccc gcctggccc gggtgtccc cagcctgcgc gggccgcttc | 480 |
| cagtccccgg tggatatccg ccccagctc gccgccttct gccggcccct cgccccctg | 540 |
| gaactcctgg gcttccagct cccgccgctc ccagaactgc gcctgcgcaa caatggccac | 600 |
| agtgtgcaac tgaccctgcc tcctgggcta gagatggctc tgggtcccgg gcgggagtac | 660 |
| cgggctctgc agctgcatct gcactggggg gctgcaggtc gtccgggctc ggagcacact | 720 |
| gtggaaggcc accgtttccc tgccgagatc cacgtggttc acctcagcac cgcctttgcc | 780 |
| agagttgacg aggccttggg gcgccccgga ggcctggccg tgttggccgc ctttctggag | 840 |
| gagggcccgg aagaaaacag tgcctatgag cagttgctgt ctcgcttgga agaaatcgct | 900 |
| gaggaaggct cagagactca ggtcccagga ctggacatat ctgcactcct gccctctgac | 960 |
| ttcagccgct acttccaata tgaggggtct ctgactacac cgccctgtgc ccagggtgtc | 1020 |
| atctggactg tgtttaacca gacagtgatg ctgagtgcta agcagctcca caccctctct | 1080 |
| gacaccctgt ggggacctgg tgactctcgg ctacagctga acttccgagc gacgcagcct | 1140 |
| ttgaatgggc gagtgattga ggcctccttc cctgctggag tggacagcag tcctcgggct | 1200 |
| gctgagccag tccagctgaa ttcctgcctg gctgctggtg acatcctagc cctggttttt | 1260 |
| ggcctccttt ttgctgtcac cagcgtcgcg ttccttgtgc agatgagaag gcagcacaga | 1320 |
| aggggaacca aagggggtgt gagctaccgc ccagcagagg tagccgagac tggagcctag | 1380 |

<210> SEQ ID NO 6
<211> LENGTH: 1611

<212> TYPE: DNA
<213> ORGANISM: Homo sapiens

<400> SEQUENCE: 6

```
atgggtagca acaagagcaa gcccaaggat gccagccagc ggcgccgcag cctggagccc      60
gccgagaacg tgcacggcgc tggcggggc gcttccccg cctcgcagac ccccagcaag     120
ccagcctcgg ccgacggcca ccgcggcccc agcgcggcct tcgccccgc ggccgccgag     180
cccaagctgt tcggaggctt caactcctcg gacaccgtca cctccccgca gagggcgggc     240
ccgctggccg gtggagtgac caccttttgtg gccctctatg actatgagtc taggacggag     300
acagacctgt ccttcaagaa aggcgagcgg ctccagattg tcaacaacac agagggagac     360
tggtggctgg cccactcgct cagcacagga cagacaggct acatccccag caactacgtg     420
gcgccctccg actccatcca ggctgaggag tggtattttg caagatcac cagacgggag     480
tcagagcggt tactgctcaa tgcagagaac ccgagaggga ccttcctcgt gcgagaaagt     540
gagaccacga aggtgccta ctgcctctca gtgtctgact cgacaacgc caagggcctc     600
aacgtgaagc actacaagat ccgcaagctg acagcggcg gcttctacat cacctcccgc     660
acccagttca cagcctgca gcagctggtg gcctactact ccaaacacgc cgatggcctg     720
tgccaccgcc tcaccaccgt gtgcccacg tccaagccgc agactcaggg cctggccaag     780
gatgcctggg agatccctcg ggagtcgctg cggctgagg tcaagctggg ccagggctgc     840
tttggcgagg tgtggatggg gacctggaac ggtaccacca gggtggccat caaaaccctg     900
aagcctggca gatgtctcc agaggccttc ctgcaggagg cccaggtcat gaagaagctg     960
aggcatgaga agctggtgca gttgtatgct gtggttcag aggagcccat ttacatcgtc    1020
acggagtaca tgagcaaggg gagtttgctg gactttctca aggggggagac aggcaagtac    1080
ctgcggctgc ctcagctggt ggacatggct gctcagatcg cctcaggcat ggcgtacgtg    1140
gagcggatga actacgtcca ccgggaccctt cgtgcagcca acatcctggt gggagagaac    1200
ctggtgtgca aagtggccga ctttgggctg gctcggctca ttgaagacaa tgagtacacg    1260
gcgcggcaag gtgccaaatt ccccatcaag tggacggctc cagaagctgc cctctatggc    1320
cgcttcacca tcaagtcgga cgtgtggtcc ttcgggatcc tgctgactga gctcaccaca    1380
aagggacggg tgcccacc tgggatggtg aaccgcgagg tgctggacca ggtggagcgg    1440
ggctaccgga tgcctgccc gccggagtgt cccgagtccc tgcacgacct catgtgccag    1500
tgctggcgga aggagcctga ggagcggccc accttcgagt acctgcaggc cttcctggag    1560
gactacttca cgtccaccga gccccagtac cagcccgggg agaacctcta g            1611
```

<210> SEQ ID NO 7
<211> LENGTH: 213
<212> TYPE: PRT
<213> ORGANISM: Homo sapiens

<400> SEQUENCE: 7

```
Met Pro Arg Arg Ala Glu Asn Trp Asp Glu Ala Glu Val Gly Ala Glu
1               5                   10                  15
Glu Ala Gly Val Glu Glu Tyr Gly Pro Glu Glu Asp Gly Gly Glu Glu
            20                  25                  30
Ser Gly Ala Glu Glu Ser Gly Pro Glu Glu Ser Gly Pro Glu Glu Leu
        35                  40                  45
Gly Ala Glu Glu Glu Met Glu Ala Gly Arg Pro Arg Pro Val Leu Arg
    50                  55                  60
```

```
Ser Val Asn Ser Arg Glu Pro Ser Gln Val Ile Phe Cys Asn Arg Ser
 65                  70                  75                  80

Pro Arg Val Val Leu Pro Val Trp Leu Asn Phe Asp Gly Glu Pro Gln
                 85                  90                  95

Pro Tyr Pro Thr Leu Pro Pro Gly Thr Gly Arg Arg Ile His Ser Tyr
            100                 105                 110

Arg Gly His Leu Trp Leu Phe Arg Asp Ala Gly Thr His Asp Gly Leu
        115                 120                 125

Leu Val Asn Gln Thr Glu Leu Phe Val Pro Ser Leu Asn Val Asp Gly
    130                 135                 140

Gln Pro Ile Phe Ala Asn Ile Thr Leu Pro Val Tyr Thr Leu Lys Glu
145                 150                 155                 160

Arg Cys Leu Gln Val Val Arg Ser Leu Val Lys Pro Glu Asn Tyr Arg
                165                 170                 175

Arg Leu Asp Ile Val Arg Ser Leu Tyr Glu Asp Leu Glu Asp His Pro
            180                 185                 190

Asn Val Gln Lys Asp Leu Glu Arg Leu Thr Gln Glu Arg Ile Ala His
        195                 200                 205

Gln Arg Met Gly Asp
    210

<210> SEQ ID NO 8
<211> LENGTH: 435
<212> TYPE: PRT
<213> ORGANISM: Homo sapiens

<400> SEQUENCE: 8

Met Glu Met Glu Lys Glu Phe Glu Gln Ile Asp Lys Ser Gly Ser Trp
  1               5                  10                  15

Ala Ala Ile Tyr Gln Asp Ile Arg His Glu Ala Ser Asp Phe Pro Cys
                 20                  25                  30

Arg Val Ala Lys Leu Pro Lys Asn Lys Asn Arg Asn Arg Tyr Arg Asp
             35                  40                  45

Val Ser Pro Phe Asp His Ser Arg Ile Lys Leu His Gln Glu Asp Asn
 50                  55                  60

Asp Tyr Ile Asn Ala Ser Leu Ile Lys Met Glu Glu Ala Gln Arg Ser
 65                  70                  75                  80

Tyr Ile Leu Thr Gln Gly Pro Leu Pro Asn Thr Cys Gly His Phe Trp
                 85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val Val His Cys Ser Ala Gly Ile Gly Arg Ser Gly Thr
    210                 215                 220
```

-continued

```
Phe Cys Leu Ala Asp Thr Cys Leu Leu Met Asp Lys Arg Lys Asp
225                 230                 235                 240

Pro Ser Ser Val Asp Ile Lys Lys Val Leu Glu Met Arg Lys Phe
            245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
            275                 280                 285

Asp Gln Trp Lys Glu Leu Ser His Glu Asp Leu Glu Pro Pro Glu
            290                 295                 300

His Ile Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
            325                 330                 335

Glu Thr Gln Glu Asp Lys Asp Cys Pro Ile Lys Glu Lys Gly Ser
            340                 345                 350

Pro Leu Asn Ala Ala Pro Tyr Gly Ile Glu Ser Met Ser Gln Asp Thr
            355                 360                 365

Glu Val Arg Ser Arg Val Val Gly Gly Ser Leu Arg Gly Ala Gln Ala
            370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                405                 410                 415

Thr Val Leu Thr Ala Gly Ala Tyr Leu Cys Tyr Arg Phe Leu Phe Asn
            420                 425                 430

Ser Asn Thr
        435

<210> SEQ ID NO 9
<211> LENGTH: 826
<212> TYPE: PRT
<213> ORGANISM: Homo sapiens

<400> SEQUENCE: 9

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
```

```
              145                 150                 155                 160
Gln Asn Thr Gln Arg Ser Phe Phe Leu Arg Met Lys Cys Thr Leu Thr
                    165                 170                 175
Ser Arg Gly Arg Thr Met Asn Ile Lys Ser Ala Thr Trp Lys Val Leu
                    180                 185                 190
His Cys Thr Gly His Ile His Val Tyr Asp Thr Asn Ser Asn Gln Pro
                    195                 200                 205
Gln Cys Gly Tyr Lys Lys Pro Pro Met Thr Cys Leu Val Leu Ile Cys
                    210                 215                 220
Glu Pro Ile Pro His Pro Ser Asn Ile Glu Ile Pro Leu Asp Ser Lys
225                 230                 235                 240
Thr Phe Leu Ser Arg His Ser Leu Asp Met Lys Phe Ser Tyr Cys Asp
                    245                 250                 255
Glu Arg Ile Thr Glu Leu Met Gly Tyr Glu Pro Glu Glu Leu Leu Gly
                    260                 265                 270
Arg Ser Ile Tyr Glu Tyr Tyr His Ala Leu Asp Ser Asp His Leu Thr
                    275                 280                 285
Lys Thr His His Asp Met Phe Thr Lys Gly Gln Val Thr Thr Gly Gln
                    290                 295                 300
Tyr Arg Met Leu Ala Lys Arg Gly Gly Tyr Val Trp Val Glu Thr Gln
305                 310                 315                 320
Ala Thr Val Ile Tyr Asn Thr Lys Asn Ser Gln Pro Gln Cys Ile Val
                    325                 330                 335
Cys Val Asn Tyr Val Val Ser Gly Ile Ile Gln His Asp Leu Ile Phe
                    340                 345                 350
Ser Leu Gln Gln Thr Glu Cys Val Leu Lys Pro Val Glu Ser Ser Asp
                    355                 360                 365
Met Lys Met Thr Gln Leu Phe Thr Lys Val Glu Ser Glu Asp Thr Ser
                    370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
                    405                 410                 415
Asp Thr Glu Thr Asp Asp Gln Gln Leu Glu Glu Val Pro Leu Tyr Asn
                    420                 425                 430
Asp Val Met Leu Pro Ser Pro Asn Glu Lys Leu Gln Asn Ile Asn Leu
                    435                 440                 445
Ala Met Ser Pro Leu Pro Thr Ala Glu Thr Pro Lys Pro Leu Arg Ser
450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
                    485                 490                 495
Gln Thr Pro Ser Pro Ser Asp Gly Ser Thr Arg Gln Ser Ser Pro Glu
                    500                 505                 510
Pro Asn Ser Pro Ser Glu Tyr Cys Phe Tyr Val Asp Ser Asp Met Val
                    515                 520                 525
Asn Glu Phe Lys Leu Glu Leu Val Glu Lys Leu Phe Ala Glu Asp Thr
                    530                 535                 540
Glu Ala Lys Asn Pro Phe Ser Thr Gln Asp Thr Asp Leu Asp Leu Glu
545                 550                 555                 560
Met Leu Ala Pro Tyr Ile Pro Met Asp Asp Asp Phe Gln Leu Arg Ser
                    565                 570                 575
```

Phe Asp Gln Leu Ser Pro Leu Glu Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
                660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
        690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 10
<211> LENGTH: 1074
<212> TYPE: PRT
<213> ORGANISM: Homo sapiens

<400> SEQUENCE: 10

Met Ile Ser Ala Asp Cys Asn Leu Cys Leu Pro Glu Tyr Asp Arg Tyr
1               5                   10                  15

Leu Ala Ser Ser Lys Ile Met Ala Ala Ala Tyr Leu Asp Pro Asn Leu
            20                  25                  30

Asn His Thr Pro Asn Ser Ser Thr Lys Thr His Leu Gly Thr Gly Met
        35                  40                  45

Glu Arg Ser Pro Gly Ala Met Glu Arg Val Leu Lys Val Phe His Tyr
    50                  55                  60

Phe Glu Ser Asn Ser Glu Pro Thr Thr Trp Ala Ser Ile Ile Arg His
65                  70                  75                  80

Gly Asp Ala Thr Asp Val Arg Gly Ile Ile Gln Lys Ile Val Asp Ser
                85                  90                  95

His Lys Val Lys His Val Ala Cys Tyr Gly Phe Arg Leu Ser His Leu
            100                 105                 110

Arg Ser Glu Glu Val His Trp Leu His Val Asp Met Gly Val Ser Ser

-continued

```
            115                 120                 125
Val Arg Glu Lys Tyr Glu Leu Ala His Pro Glu Glu Trp Lys Tyr
130                 135                 140
Glu Leu Arg Ile Arg Tyr Leu Pro Lys Gly Phe Leu Asn Gln Phe Thr
145                 150                 155                 160
Glu Asp Lys Pro Thr Leu Asn Phe Phe Tyr Gln Gln Val Lys Ser Asp
                165                 170                 175
Tyr Met Leu Glu Ile Ala Asp Gln Val Asp Gln Glu Ile Ala Leu Lys
            180                 185                 190
Leu Gly Cys Leu Glu Ile Arg Arg Ser Tyr Trp Glu Met Arg Gly Asn
            195                 200                 205
Ala Leu Glu Lys Lys Ser Asn Tyr Glu Val Leu Glu Lys Asp Val Gly
            210                 215                 220
Leu Lys Arg Phe Phe Pro Lys Ser Leu Leu Asp Ser Val Lys Ala Lys
225                 230                 235                 240
Thr Leu Arg Lys Leu Ile Gln Gln Thr Phe Arg Gln Phe Ala Asn Leu
                245                 250                 255
Asn Arg Glu Glu Ser Ile Leu Lys Phe Phe Glu Ile Leu Ser Pro Val
            260                 265                 270
Tyr Arg Phe Asp Lys Glu Cys Phe Lys Cys Ala Leu Gly Ser Ser Trp
            275                 280                 285
Ile Ile Ser Val Glu Leu Ala Ile Gly Pro Glu Glu Gly Ile Ser Tyr
            290                 295                 300
Leu Thr Asp Lys Gly Cys Asn Pro Thr His Leu Ala Asp Phe Thr Gln
305                 310                 315                 320
Val Gln Thr Ile Gln Tyr Ser Asn Ser Glu Asp Lys Asp Arg Lys Gly
                325                 330                 335
Met Leu Gln Leu Lys Ile Ala Gly Ala Pro Glu Pro Leu Thr Val Thr
            340                 345                 350
Ala Pro Ser Leu Thr Ile Ala Glu Asn Met Ala Asp Leu Ile Asp Gly
            355                 360                 365
Tyr Cys Arg Leu Val Asn Gly Thr Ser Gln Ser Phe Ile Ile Arg Pro
            370                 375                 380
Gln Lys Glu Gly Glu Arg Ala Leu Pro Ser Ile Pro Lys Leu Ala Asn
385                 390                 395                 400
Ser Glu Lys Gln Gly Met Arg Thr His Ala Val Ser Val Ser Glu Thr
                405                 410                 415
Asp Asp Tyr Ala Glu Ile Ile Asp Glu Glu Asp Thr Tyr Thr Met Pro
            420                 425                 430
Ser Thr Arg Asp Tyr Glu Ile Gln Arg Glu Arg Ile Glu Leu Gly Arg
            435                 440                 445
Cys Ile Gly Glu Gly Gln Phe Gly Asp Val His Gln Gly Ile Tyr Met
            450                 455                 460
Ser Pro Glu Asn Pro Ala Leu Ala Val Ala Ile Lys Thr Cys Lys Asn
465                 470                 475                 480
Cys Thr Ser Asp Ser Val Arg Glu Lys Phe Leu Gln Glu Ala Leu Thr
                485                 490                 495
Met Arg Gln Phe Asp His Pro His Ile Val Lys Leu Ile Gly Val Ile
            500                 505                 510
Thr Glu Asn Pro Val Trp Ile Ile Met Glu Leu Cys Thr Leu Gly Glu
            515                 520                 525
Leu Arg Ser Phe Leu Gln Val Arg Lys Tyr Ser Leu Asp Leu Ala Ser
            530                 535                 540
```

```
Leu Ile Leu Tyr Ala Tyr Gln Leu Ser Thr Ala Leu Ala Tyr Leu Glu
545                 550                 555                 560

Ser Lys Arg Phe Val His Arg Asp Ile Ala Ala Arg Asn Val Leu Val
                565                 570                 575

Ser Ser Asn Asp Cys Val Lys Leu Gly Asp Phe Gly Leu Ser Arg Tyr
            580                 585                 590

Met Glu Asp Ser Thr Tyr Tyr Lys Ala Ser Lys Gly Lys Leu Pro Ile
        595                 600                 605

Lys Trp Met Ala Pro Glu Ser Ile Asn Phe Arg Arg Phe Thr Ser Ala
610                 615                 620

Ser Asp Val Trp Met Phe Gly Val Cys Met Trp Glu Ile Leu Met His
625                 630                 635                 640

Gly Val Lys Pro Phe Gln Gly Val Lys Asn Asn Asp Val Ile Gly Arg
                645                 650                 655

Ile Glu Asn Gly Glu Arg Leu Pro Met Pro Asn Cys Pro Pro Thr
            660                 665                 670

Leu Tyr Ser Leu Met Thr Lys Cys Trp Ala Tyr Asp Pro Ser Arg Arg
        675                 680                 685

Pro Arg Phe Thr Glu Leu Lys Ala Gln Leu Ser Thr Ile Leu Glu Glu
    690                 695                 700

Glu Lys Ala Gln Gln Glu Arg Met Arg Met Glu Ser Arg Arg Gln
705                 710                 715                 720

Ala Thr Val Ser Trp Asp Ser Gly Gly Ser Asp Glu Ala Pro Pro Lys
                725                 730                 735

Pro Ser Arg Pro Gly Tyr Pro Ser Pro Arg Ser Ser Glu Gly Phe Tyr
            740                 745                 750

Pro Ser Pro Gln His Met Val Gln Thr Asn His Tyr Gln Val Ser Gly
        755                 760                 765

Tyr Pro Gly Ser His Gly Ile Thr Ala Met Ala Gly Ser Ile Tyr Pro
    770                 775                 780

Gly Gln Ala Ser Leu Leu Asp Gln Thr Asp Ser Trp Asn His Arg Pro
785                 790                 795                 800

Gln Glu Ile Ala Met Trp Gln Pro Asn Val Glu Asp Ser Thr Val Leu
                805                 810                 815

Asp Leu Arg Gly Ile Gly Gln Val Leu Pro Thr His Leu Met Glu Glu
            820                 825                 830

Arg Leu Ile Arg Gln Gln Gln Glu Met Glu Asp Gln Arg Trp Leu
        835                 840                 845

Glu Lys Glu Glu Arg Phe Leu Lys Pro Asp Val Arg Leu Ser Arg Gly
    850                 855                 860

Ser Ile Asp Arg Glu Asp Gly Ser Leu Gln Gly Pro Ile Gly Asn Gln
865                 870                 875                 880

His Ile Tyr Gln Pro Val Gly Lys Pro Asp Pro Ala Ala Pro Pro Lys
                885                 890                 895

Lys Pro Pro Arg Pro Gly Ala Pro Gly His Leu Gly Ser Leu Ala Ser
            900                 905                 910

Leu Ser Ser Pro Ala Asp Ser Tyr Asn Glu Gly Val Lys Leu Gln Pro
        915                 920                 925

Gln Glu Ile Ser Pro Pro Thr Ala Asn Leu Asp Arg Ser Asn Asp
    930                 935                 940

Lys Val Tyr Glu Asn Val Thr Gly Leu Val Lys Ala Val Ile Glu Met
945                 950                 955                 960
```

Ser Ser Lys Ile Gln Pro Ala Pro Glu Glu Tyr Val Pro Met Val
                965                 970                 975

Lys Glu Val Gly Leu Ala Leu Arg Thr Leu Leu Ala Thr Val Asp Glu
            980                 985                 990

Thr Ile Pro Leu Leu Pro Ala Ser Thr His Arg Glu Ile Glu Met Ala
        995                 1000                1005

Gln Lys Leu Leu Asn Ser Asp Leu Gly Glu Leu Ile Asn Lys Met
    1010                1015                1020

Lys Leu Ala Gln Gln Tyr Val Met Thr Ser Leu Gln Gln Glu Tyr
    1025                1030                1035

Lys Lys Gln Met Leu Thr Ala Ala His Ala Leu Ala Val Asp Ala
    1040                1045                1050

Lys Asn Leu Leu Asp Val Ile Asp Gln Ala Arg Leu Lys Met Leu
    1055                1060                1065

Gly Gln Thr Arg Pro His
    1070

<210> SEQ ID NO 11
<211> LENGTH: 459
<212> TYPE: PRT
<213> ORGANISM: Homo sapiens

<400> SEQUENCE: 11

Met Ala Pro Leu Cys Pro Ser Pro Trp Leu Pro Leu Leu Ile Pro Ala
1               5                   10                  15

Pro Ala Pro Gly Leu Thr Val Gln Leu Leu Ser Leu Leu Leu Leu
            20                  25                  30

Val Pro Val His Pro Gln Arg Leu Pro Arg Met Gln Glu Asp Ser Pro
        35                  40                  45

Leu Gly Gly Gly Ser Ser Gly Glu Asp Asp Pro Leu Gly Glu Glu Asp
    50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Gly Ser Leu Lys Leu Glu Asp
            100                 105                 110

Leu Pro Thr Val Glu Ala Pro Gly Asp Pro Gln Glu Pro Gln Asn Asn
        115                 120                 125

Ala His Arg Asp Lys Glu Gly Asp Asp Gln Ser His Trp Arg Tyr Gly
    130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
        195                 200                 205

Gly Leu Glu Met Ala Leu Gly Pro Gly Arg Glu Tyr Arg Ala Leu Gln
    210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

```
            Thr Ala Phe Ala Arg Val Asp Glu Ala Leu Gly Arg Pro Gly Gly Leu
                        260                 265                 270

Ala Val Leu Ala Ala Phe Leu Glu Glu Gly Pro Glu Glu Asn Ser Ala
                    275                 280                 285

Tyr Glu Gln Leu Leu Ser Arg Leu Glu Glu Ile Ala Glu Glu Gly Ser
                290                 295                 300

Glu Thr Gln Val Pro Gly Leu Asp Ile Ser Ala Leu Leu Pro Ser Asp
            305                 310                 315                 320

Phe Ser Arg Tyr Phe Gln Tyr Glu Gly Ser Leu Thr Thr Pro Pro Cys
                            325                 330                 335

Ala Gln Gly Val Ile Trp Thr Val Phe Asn Gln Thr Val Met Leu Ser
                        340                 345                 350

Ala Lys Gln Leu His Thr Leu Ser Asp Thr Leu Trp Gly Pro Gly Asp
                    355                 360                 365

Ser Arg Leu Gln Leu Asn Phe Arg Ala Thr Gln Pro Leu Asn Gly Arg
                370                 375                 380

Val Ile Glu Ala Ser Phe Pro Ala Gly Val Asp Ser Ser Pro Arg Ala
            385                 390                 395                 400

Ala Glu Pro Val Gln Leu Asn Ser Cys Leu Ala Ala Gly Asp Ile Leu
                            405                 410                 415

Ala Leu Val Phe Gly Leu Leu Phe Ala Val Thr Ser Val Ala Phe Leu
                        420                 425                 430

Val Gln Met Arg Arg Gln His Arg Arg Gly Thr Lys Gly Gly Val Ser
                    435                 440                 445

Tyr Arg Pro Ala Glu Val Ala Glu Thr Gly Ala
                450                 455

<210> SEQ ID NO 12
<211> LENGTH: 536
<212> TYPE: PRT
<213> ORGANISM: Homo sapiens

<400> SEQUENCE: 12

Met Gly Ser Asn Lys Ser Lys Pro Lys Asp Ala Ser Gln Arg Arg Arg
            1               5                   10                  15

Ser Leu Glu Pro Ala Glu Asn Val His Gly Ala Gly Gly Gly Ala Phe
                            20                  25                  30

Pro Ala Ser Gln Thr Pro Ser Lys Pro Ala Ser Ala Asp Gly His Arg
                        35                  40                  45

Gly Pro Ser Ala Ala Phe Ala Pro Ala Ala Glu Pro Lys Leu Phe
                    50                  55                  60

Gly Gly Phe Asn Ser Ser Asp Thr Val Thr Ser Pro Gln Arg Ala Gly
            65                  70                  75                  80

Pro Leu Ala Gly Gly Val Thr Thr Phe Val Ala Leu Tyr Asp Tyr Glu
                            85                  90                  95

Ser Arg Thr Glu Thr Asp Leu Ser Phe Lys Lys Gly Glu Arg Leu Gln
                        100                 105                 110

Ile Val Asn Asn Thr Glu Gly Asp Trp Trp Leu Ala His Ser Leu Ser
                    115                 120                 125

Thr Gly Gln Thr Gly Tyr Ile Pro Ser Asn Tyr Val Ala Pro Ser Asp
                130                 135                 140

Ser Ile Gln Ala Glu Glu Trp Tyr Phe Gly Lys Ile Thr Arg Arg Glu
            145                 150                 155                 160

Ser Glu Arg Leu Leu Leu Asn Ala Glu Asn Pro Arg Gly Thr Phe Leu
```

-continued

```
                165                 170                 175
Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
            195                 200                 205

Lys Leu Asp Ser Gly Gly Phe Tyr Ile Thr Ser Arg Thr Gln Phe Asn
            210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
            275                 280                 285

Trp Asn Gly Thr Thr Arg Val Ala Ile Lys Thr Leu Lys Pro Gly Thr
            290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
            340                 345                 350

Leu Lys Gly Glu Thr Gly Lys Tyr Leu Arg Leu Pro Gln Leu Val Asp
            355                 360                 365

Met Ala Ala Gln Ile Ala Ser Gly Met Ala Tyr Val Glu Arg Met Asn
            370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
            435                 440                 445

Trp Ser Phe Gly Ile Leu Leu Thr Glu Leu Thr Thr Lys Gly Arg Val
            450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
            500                 505                 510

Glu Tyr Leu Gln Ala Phe Leu Glu Asp Tyr Phe Thr Ser Thr Glu Pro
            515                 520                 525

Gln Tyr Gln Pro Gly Glu Asn Leu
530                 535
```